(12) United States Patent
Beier

(10) Patent No.: US 10,961,579 B2
(45) Date of Patent: Mar. 30, 2021

(54) MIRNAS AS NON-INVASIVE BIOMARKERS FOR PARKINSON'S DISEASE

(71) Applicant: Hummingbird Diagnostics GmbH, Heidelberg (DE)

(72) Inventor: Markus Beier, Weinheim (DE)

(73) Assignee: HUMMINGBIRD DIAGNOSTICS GMBH, Heidelberg (DE)

( * ) Notice: Subject to any disclaimer, the term of this patent is extended or adjusted under 35 U.S.C. 154(b) by 0 days.

(21) Appl. No.: 15/105,728

(22) PCT Filed: Dec. 19, 2014

(86) PCT No.: PCT/EP2014/078623
§ 371 (c)(1),
(2) Date: Jun. 17, 2016

(87) PCT Pub. No.: WO2015/091892
PCT Pub. Date: Jun. 25, 2015

(65) Prior Publication Data
US 2016/0326588 A1 Nov. 10, 2016

(30) Foreign Application Priority Data
Dec. 19, 2013 (EP) .................... 13198606

(51) Int. Cl.
*C12Q 1/68* (2018.01)
*C12P 19/34* (2006.01)
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
CPC ............ C12Q 1/6883; C12Q 2600/158; C12Q 2600/178
See application file for complete search history.

(56) References Cited

U.S. PATENT DOCUMENTS

2012/0108462 A1* 5/2012 Keller ................. C12Q 1/6809 506/9
2013/0157883 A1* 6/2013 Keller ................. C12Q 1/6883 506/9

FOREIGN PATENT DOCUMENTS

WO 2011/029903 3/2011
WO 2013/036936 3/2013
WO 2013/124816 8/2013

OTHER PUBLICATIONS

Martins, M. et al. PLoS One. 2011; 6(10): e25443, printed pp. 1-11.*
Benes, V. et al. "Expression profiling of microRNA using real-time quantitative PCR, how to use it and what is available". Methods 50 (2010) 244-249. (Year: 2010).*
TaqMan® miRNA ABC Purification Kit User Guide, from tools.thermofisher.com, Sep. 4, 2012 (Year: 2012).*
Martins et al., "Convergence of rniRNA Expression Profiling, a-Synuclein Interacton and GWAS in Parkinson's Disease", PLOS ONE, 6(10): 1-11 (2011).
International Search Report, dated Mar. 27, 2015 in corresponding International Patent Application No. PCT/EP2014/078623.

* cited by examiner

Primary Examiner — Stephen T Kapushoc
(74) Attorney, Agent, or Firm — Wenderoth, Lind & Ponack, L.L.P.

(57) ABSTRACT

The present invention relates to methods, kits and means for diagnosing Parkinson's disease in a blood sample from a subject. Further, the present invention relates to a set of polynucleotides for detecting sets of miRNAs for diagnosing Parkinson's disease in a blood sample from a subject.

15 Claims, 16 Drawing Sheets
Specification includes a Sequence Listing.

Figure 1

| Seq ID NO: | miRNA | Parkinson, median g1 | Healhty Control, median g2 | log2FC | ttest rawp | ttest adjp | AUC | limma rawp | limma adjp |
|---|---|---|---|---|---|---|---|---|---|
| 1 | hsa-miR-23a | 4144 | 1786 | 1.21 | 8.57E-02 | 3.49E-01 | 0.34 | 4.91E-02 | 2.96E-01 |
| 2 | hsa-miR-1228 | 310 | 696 | -1.17 | 1.21E-04 | 1.18E-02 | 0.86 | 1.64E-06 | 1.39E-03 |
| 3 | hsa-miR-150 | 1439 | 715 | 1.01 | 4.07E-01 | 6.49E-01 | 0.42 | 3.69E-01 | 6.45E-01 |
| 4 | hsa-miR-24 | 1925 | 1014 | 0.92 | 2.11E-03 | 4.71E-02 | 0.29 | 1.53E-02 | 1.71E-01 |
| 5 | hsa-miR-106a | 6699 | 3530 | 0.92 | 7.33E-02 | 3.21E-01 | 0.34 | 4.04E-02 | 2.71E-01 |
| 6 | hsa-miR-361-5p | 456 | 847 | -0.89 | 5.05E-03 | 7.46E-02 | 0.76 | 2.88E-03 | 8.18E-02 |
| 7 | hsa-miR-20a | 3282 | 1803 | 0.86 | 1.18E-01 | 3.97E-01 | 0.36 | 9.01E-02 | 3.91E-01 |
| 8 | hsa-miR-126 | 1673 | 927 | 0.85 | 9.76E-02 | 3.66E-01 | 0.36 | 7.06E-02 | 3.61E-01 |
| 9 | hsa-miR-574-5p | 757 | 1364 | -0.85 | 3.58E-03 | 6.32E-02 | 0.74 | 4.35E-03 | 9.50E-02 |
| 10 | hsa-miR-664 | 349 | 199 | 0.81 | 3.07E-01 | 5.64E-01 | 0.40 | 1.92E-01 | 5.00E-01 |
| 11 | hsa-miR-185 | 23521 | 13447 | 0.81 | 2.20E-01 | 4.94E-01 | 0.38 | 2.78E-01 | 5.63E-01 |
| 12 | hsa-miR-451 | 1225 | 725 | 0.76 | 7.36E-02 | 3.21E-01 | 0.35 | 6.58E-02 | 3.43E-01 |
| 13 | hsa-miR-93 | 3947 | 2341 | 0.75 | 2.95E-01 | 5.53E-01 | 0.40 | 3.47E-01 | 6.31E-01 |
| 14 | hsa-miR-660 | 549 | 326 | 0.75 | 9.10E-02 | 3.58E-01 | 0.35 | 8.57E-02 | 3.86E-01 |
| 15 | hsa-miR-320b | 2369 | 1421 | 0.74 | 1.71E-01 | 4.44E-01 | 0.37 | 1.70E-01 | 4.90E-01 |
| 16 | hsa-miR-486-5p | 35047 | 21075 | 0.73 | 5.70E-02 | 3.04E-01 | 0.34 | 3.00E-02 | 2.40E-01 |
| 17 | hsa-miR-103 | 8526 | 5225 | 0.71 | 1.28E-02 | 1.29E-01 | 0.27 | 3.57E-03 | 8.90E-02 |
| 18 | hsa-miR-423-5p | 2629 | 4274 | -0.70 | 7.04E-04 | 3.14E-02 | 0.74 | 5.49E-03 | 1.08E-01 |
| 19 | hsa-miR-187* | 219 | 355 | -0.70 | 3.71E-06 | 1.05E-03 | 0.87 | 5.54E-06 | 1.79E-03 |
| 20 | hsa-miR-9* | 170 | 274 | -0.69 | 1.49E-02 | 1.41E-01 | 0.74 | 1.54E-03 | 6.23E-02 |
| 21 | hsa-miR-142-5p | 747 | 468 | 0.67 | 1.17E-01 | 3.97E-01 | 0.36 | 9.34E-02 | 3.98E-01 |
| 22 | hsa-miR-891b | 168 | 106 | 0.67 | 1.29E-03 | 3.77E-02 | 0.18 | 4.90E-05 | 8.25E-03 |
| 23 | hsa-miR-18b | 267 | 423 | -0.66 | 1.32E-01 | 4.01E-01 | 0.66 | 8.68E-02 | 3.86E-01 |
| 24 | hsa-miR-374b | 639 | 407 | 0.65 | 6.50E-02 | 3.08E-01 | 0.34 | 5.31E-02 | 3.05E-01 |
| 25 | hsa-miR-23b | 3214 | 2050 | 0.65 | 2.74E-01 | 5.46E-01 | 0.38 | 2.59E-01 | 5.50E-01 |
| 26 | hsa-miR-19b | 10555 | 6734 | 0.65 | 5.20E-01 | 7.34E-01 | 0.44 | 4.75E-01 | 7.20E-01 |
| 27 | hsa-miR-629 | 171 | 109 | 0.64 | 5.15E-01 | 7.29E-01 | 0.42 | 5.42E-01 | 7.68E-01 |
| 28 | hsa-miR-30c | 1902 | 1224 | 0.64 | 9.45E-01 | 9.67E-01 | 0.49 | 9.45E-01 | 9.74E-01 |
| 29 | hsa-miR-1228* | 1081 | 1680 | -0.64 | 9.01E-02 | 3.57E-01 | 0.62 | 1.07E-01 | 4.17E-01 |
| 30 | hsa-miR-93* | 984 | 1512 | -0.62 | 5.12E-02 | 2.92E-01 | 0.69 | 2.64E-02 | 2.28E-01 |
| 31 | hsa-miR-324-3p | 693 | 1060 | -0.61 | 1.48E-02 | 1.41E-01 | 0.72 | 1.05E-02 | 1.44E-01 |
| 32 | hsa-miR-363 | 3999 | 2616 | 0.61 | 8.36E-02 | 3.42E-01 | 0.35 | 8.07E-02 | 3.74E-01 |
| 33 | hsa-miR-296-5p | 329 | 501 | -0.61 | 6.10E-04 | 3.14E-02 | 0.74 | 4.68E-03 | 9.67E-02 |
| 34 | hsa-miR-106b | 10505 | 6910 | 0.60 | 5.24E-02 | 2.92E-01 | 0.32 | 4.76E-02 | 2.92E-01 |
| 35 | hsa-miR-144 | 2349 | 1565 | 0.59 | 4.16E-01 | 6.56E-01 | 0.44 | 3.21E-01 | 6.09E-01 |
| 36 | hsa-let-7c | 449 | 534 | -0.25 | 6.94E-01 | 8.38E-01 | 0.53 | 7.14E-01 | 8.69E-01 |
| 37 | hsa-let-7d | 2067 | 2530 | -0.29 | 3.05E-01 | 5.63E-01 | 0.57 | 4.26E-01 | 6.92E-01 |
| 38 | hsa-miR-320a | 13017 | 15140 | -0.22 | 3.83E-01 | 6.28E-01 | 0.58 | 3.40E-01 | 6.23E-01 |

Figure 1 con't

| 39 | hsa-miR-149* | 616 | 735 | -0.26 | 3.29E-01 | 5.89E-01 | 0.59 | 2.84E-01 | 5.69E-01 |
|---|---|---|---|---|---|---|---|---|---|
| 40 | hsa-miR-320d | 739 | 756 | -0.03 | 6.71E-01 | 8.22E-01 | 0.52 | 6.61E-01 | 8.40E-01 |
| 41 | hsa-miR-222 | 518 | 553 | -0.09 | 6.43E-01 | 8.14E-01 | 0.48 | 6.59E-01 | 8.40E-01 |
| 42 | hsa-miR-16-2* | 178 | 163 | 0.13 | 8.30E-01 | 9.19E-01 | 0.45 | 8.13E-01 | 9.19E-01 |
| 43 | hsa-miR-1470 | 248 | 293 | -0.24 | 4.08E-02 | 2.52E-01 | 0.68 | 1.51E-02 | 1.71E-01 |
| 44 | hsa-miR-1280 | 3247 | 3150 | 0.04 | 3.17E-01 | 5.75E-01 | 0.43 | 3.79E-01 | 6.50E-01 |
| 45 | hsa-miR-1908 | 972 | 1206 | -0.31 | 3.03E-02 | 2.11E-01 | 0.65 | 4.59E-02 | 2.90E-01 |
| 46 | hsa-miR-1288 | 151 | 166 | -0.14 | 5.30E-02 | 2.92E-01 | 0.64 | 7.72E-02 | 3.64E-01 |
| 47 | hsa-miR-125a-5p | 274 | 353 | -0.37 | 4.83E-02 | 2.80E-01 | 0.68 | 2.07E-02 | 2.04E-01 |
| 48 | hsa-miR-584 | 177 | 233 | -0.39 | 1.49E-01 | 4.22E-01 | 0.61 | 2.31E-01 | 5.24E-01 |
| 49 | hsa-miR-24-2* | 232 | 268 | -0.21 | 2.97E-02 | 2.08E-01 | 0.66 | 1.80E-01 | 4.96E-01 |
| 50 | hsa-miR-633 | 149 | 132 | 0.18 | 2.27E-01 | 5.02E-01 | 0.42 | 3.57E-01 | 6.37E-01 |
| 51 | hsa-miR-1285 | 337 | 353 | -0.07 | 8.02E-01 | 9.07E-01 | 0.51 | 8.13E-01 | 9.19E-01 |

Figure 2

| Signature | SEQ-ID NO: | miRNA-identifiers | Acc | Spec | Sens | bal. Acc |
|---|---|---|---|---|---|---|
| SHP-1 | 19, 22 | hsa-miR-187*, hsa-miR-891b | 89% | 88% | 94% | 91% |
| SHP-2 | 1, 2 | hsa-miR-23a, hsa-miR-1228 | 86% | 86% | 86% | 86% |
| SHP-3 | 2, 3 | hsa-miR-1228, hsa-miR-150 | 77% | 74% | 96% | 85% |
| SHP-4 | 20, 22 | hsa-miR-9*, hsa-miR-891b | 84% | 84% | 85% | 84% |
| SHP-5 | 19, 2 | hsa-miR-187*, hsa-miR-1228 | 85% | 86% | 83% | 84% |
| SHP-6 | 19, 6 | hsa-miR-187*, hsa-miR-361-5p | 82% | 82% | 84% | 83% |
| SHP-7 | 18, 4 | hsa-miR-423-5p, hsa-miR-24 | 73% | 69% | 93% | 81% |
| SHP-8 | 47, 1 | hsa-miR-125a-5p, hsa-miR-23a | 73% | 69% | 92% | 80% |
| SHP-9 | 20, 31 | hsa-miR-9*, hsa-miR-324-3p | 78% | 77% | 83% | 80% |
| SHP-10 | 17, 19 | hsa-miR-103, hsa-miR-187* | 80% | 80% | 80% | 80% |
| SHP-11 | 18, 20 | hsa-miR-423-5p, hsa-miR-9* | 78% | 77% | 83% | 80% |
| SHP-12 | 33, 20 | hsa-miR-296-5p, hsa-miR-9* | 74% | 72% | 87% | 79% |
| SHP-13 | 2, 4 | hsa-miR-1228, hsa-miR-24 | 82% | 83% | 75% | 79% |
| SHP-14 | 16, 19 | hsa-miR-486-5p, hsa-miR-187* | 76% | 75% | 83% | 79% |
| SHP-15 | 6, 20 | hsa-miR-361-5p, hsa-miR-9* | 73% | 71% | 86% | 78% |
| SHP-16 | 2, 9 | hsa-miR-1228, hsa-miR-574-5p | 88% | 93% | 64% | 78% |
| SHP-17 | 19, 21 | hsa-miR-187*, hsa-miR-142-5p | 73% | 71% | 84% | 77% |
| SHP-18 | 17, 31 | hsa-miR-103, hsa-miR-324-3p | 75% | 74% | 80% | 77% |
| SHP-19 | 18, 19 | hsa-miR-423-5p, hsa-miR-187* | 77% | 77% | 77% | 77% |
| SHP-20 | 47, 16 | hsa-miR-125a-5p, hsa-miR-486-5p | 72% | 70% | 83% | 77% |
| SHP-21 | 4, 43 | hsa-miR-24, hsa-miR-1470 | 70% | 67% | 85% | 76% |
| SHP-22 | 22, 9 | hsa-miR-891b, hsa-miR-574-5p | 79% | 81% | 72% | 76% |
| SHP-23 | 2, 22 | hsa-miR-1228, hsa-miR-891b | 84% | 88% | 63% | 76% |
| SHP-24 | 22, 25 | hsa-miR-891b, hsa-miR-23b | 80% | 82% | 68% | 75% |
| SHP-25 | 17, 20 | hsa-miR-103, hsa-miR-9* | 75% | 75% | 76% | 75% |
| SHP-26 | 2, 6 | hsa-miR-1228, hsa-miR-361-5p | 84% | 89% | 62% | 75% |
| SHP-27 | 15, 18 | hsa-miR-320b, hsa-miR-423-5p | 77% | 77% | 72% | 75% |
| SHP-28 | 19, 20 | hsa-miR-187*, hsa-miR-9* | 75% | 75% | 74% | 75% |
| SHP-29 | 33, 17 | hsa-miR-296-5p, hsa-miR-103 | 67% | 63% | 86% | 74% |
| SHP-30 | 3, 6 | hsa-miR-150, hsa-miR-361-5p | 68% | 65% | 82% | 74% |
| SHP-31 | 21, 22 | hsa-miR-142-5p, hsa-miR-891b | 83% | 87% | 60% | 73% |
| SHP-32 | 31, 4 | hsa-miR-324-3p, hsa-miR-24 | 74% | 75% | 72% | 73% |
| SHP-33 | 2, 5 | hsa-miR-1228, hsa-miR-106a | 79% | 82% | 65% | 73% |
| SHP-34 | 22, 33 | hsa-miR-891b, hsa-miR-296-5p | 77% | 79% | 67% | 73% |
| SHP-35 | 5, 6 | hsa-miR-106a, hsa-miR-361-5p | 75% | 76% | 70% | 73% |
| SHP-36 | 45, 12 | hsa-miR-1908, hsa-miR-451 | 62% | 57% | 88% | 73% |
| SHP-37 | 22, 23 | hsa-miR-891b, hsa-miR-18b | 76% | 77% | 67% | 72% |
| SHP-38 | 4, 6 | hsa-miR-24, hsa-miR-361-5p | 79% | 82% | 62% | 72% |
| SHP-39 | 18, 25 | hsa-miR-423-5p, hsa-miR-23b | 69% | 68% | 74% | 71% |
| SHP-40 | 6, 8 | hsa-miR-361-5p, hsa-miR-126 | 74% | 76% | 67% | 71% |
| SHP-41 | 22, 6 | hsa-miR-891b, hsa-miR-361-5p | 78% | 82% | 61% | 71% |

Figure 2 con't

| SHP-42 | 6, 7 | hsa-miR-361-5p, hsa-miR-20a | 73% | 73% | 69% | 71% |
|---|---|---|---|---|---|---|
| SHP-43 | 9, 18 | hsa-miR-574-5p, hsa-miR-423-5p | 66% | 64% | 76% | 70% |
| SHP-44 | 5, 23 | hsa-miR-106a, hsa-miR-18b | 74% | 76% | 64% | 70% |
| SHP-45 | 16, 18 | hsa-miR-486-5p, hsa-miR-423-5p | 67% | 65% | 75% | 70% |
| SHP-46 | 22, 24 | hsa-miR-891b, hsa-miR-374b | 81% | 86% | 55% | 70% |
| SHP-47 | 20, 21 | hsa-miR-9*, hsa-miR-142-5p | 78% | 82% | 57% | 70% |
| SHP-48 | 9, 20 | hsa-miR-574-5p, hsa-miR-9* | 68% | 67% | 72% | 70% |
| SHP-49 | 18, 21 | hsa-miR-423-5p, hsa-miR-142-5p | 74% | 76% | 63% | 70% |
| SHP-50 | 12, 18 | hsa-miR-451, hsa-miR-423-5p | 67% | 66% | 73% | 70% |
| SHP-51 | 49, 45 | hsa-miR-24-2*, hsa-miR-1908 | 65% | 63% | 76% | 69% |
| SHP-52 | 24, 45 | hsa-miR-374b, hsa-miR-1908 | 57% | 51% | 87% | 69% |
| SHP-53 | 17, 18 | hsa-miR-103, hsa-miR-423-5p | 66% | 65% | 72% | 68% |
| SHP-54 | 45, 32 | hsa-miR-1908, hsa-miR-363 | 56% | 49% | 87% | 68% |
| SHP-55 | 18, 28 | hsa-miR-423-5p, hsa-miR-30c | 63% | 61% | 75% | 68% |
| SHP-56 | 7, 9 | hsa-miR-20a, hsa-miR-574-5p | 78% | 83% | 53% | 68% |
| SHP-57 | 13, 18 | hsa-miR-93, hsa-miR-423-5p | 68% | 68% | 68% | 68% |
| SHP-58 | 9, 33 | hsa-miR-574-5p, hsa-miR-296-5p | 70% | 71% | 64% | 68% |
| SHP-59 | 45, 14 | hsa-miR-1908, hsa-miR-660 | 57% | 52% | 83% | 68% |
| SHP-60 | 9, 11 | hsa-miR-574-5p, hsa-miR-185 | 67% | 67% | 68% | 67% |
| SHP-61 | 6, 33 | hsa-miR-361-5p, hsa-miR-296-5p | 64% | 62% | 72% | 67% |
| SHP-62 | 17, 4 | hsa-miR-103, hsa-miR-24 | 58% | 53% | 80% | 67% |
| SHP-63 | 34, 47 | hsa-miR-106b, hsa-miR-125a-5p | 72% | 75% | 59% | 67% |
| SHP-64 | 49, 14 | hsa-miR-24-2*, hsa-miR-660 | 59% | 55% | 79% | 67% |
| SHP-65 | 33, 18 | hsa-miR-296-5p, hsa-miR-423-5p | 61% | 59% | 75% | 67% |
| SHP-66 | 47, 5 | hsa-miR-125a-5p, hsa-miR-106a | 58% | 55% | 78% | 66% |
| SHP-67 | 6, 9 | hsa-miR-361-5p, hsa-miR-574-5p | 64% | 63% | 70% | 66% |
| SHP-68 | 20, 23 | hsa-miR-9*, hsa-miR-18b | 70% | 72% | 60% | 66% |
| SHP-69 | 30, 47 | hsa-miR-93*, hsa-miR-125a-5p | 75% | 80% | 51% | 66% |
| SHP-70 | 12, 17 | hsa-miR-451, hsa-miR-103 | 63% | 62% | 70% | 66% |
| SHP-71 | 9, 12 | hsa-miR-574-5p, hsa-miR-451 | 59% | 56% | 75% | 65% |
| SHP-72 | 25, 37 | hsa-miR-23b, hsa-let-7d | 56% | 51% | 80% | 65% |
| SHP-73 | 1, 4 | hsa-miR-23a, hsa-miR-24 | 60% | 58% | 72% | 65% |
| SHP-74 | 11, 17 | hsa-miR-185, hsa-miR-103 | 64% | 64% | 65% | 65% |
| SHP-75 | 30, 34 | hsa-miR-93*, hsa-miR-106b | 72% | 76% | 53% | 65% |
| SHP-76 | 16, 17 | hsa-miR-486-5p, hsa-miR-103 | 66% | 66% | 62% | 64% |
| SHP-77 | 23, 49 | hsa-miR-18b, hsa-miR-24-2* | 59% | 56% | 72% | 64% |
| SHP-78 | 8, 9 | hsa-miR-126, hsa-miR-574-5p | 64% | 63% | 64% | 64% |
| SHP-79 | 16, 24 | hsa-miR-486-5p, hsa-miR-374b | 71% | 75% | 53% | 64% |
| SHP-80 | 17, 30 | hsa-miR-103, hsa-miR-93* | 70% | 74% | 54% | 64% |
| SHP-81 | 3, 4 | hsa-miR-150, hsa-miR-24 | 60% | 58% | 69% | 64% |
| SHP-82 | 43, 47 | hsa-miR-1470, hsa-miR-125a-5p | 59% | 57% | 70% | 64% |
| SHP-83 | 1, 23 | hsa-miR-23a, hsa-miR-18b | 66% | 67% | 60% | 64% |
| SHP-84 | 49, 12 | hsa-miR-24-2*, hsa-miR-451 | 52% | 47% | 80% | 64% |

Figure 2 con't

| SHP-85 | 4, 30 | hsa-miR-24, hsa-miR-93* | 71% | 75% | 52% | 63% |
|---|---|---|---|---|---|---|
| SHP-86 | 12, 14 | hsa-miR-451, hsa-miR-660 | 64% | 65% | 61% | 63% |
| SHP-87 | 17, 21 | hsa-miR-103, hsa-miR-142-5p | 67% | 69% | 57% | 63% |
| SHP-88 | 7, 46 | hsa-miR-20a, hsa-miR-1288 | 65% | 65% | 61% | 63% |
| SHP-89 | 4, 34 | hsa-miR-24, hsa-miR-106b | 61% | 60% | 66% | 63% |
| SHP-90 | 5, 11 | hsa-miR-106a, hsa-miR-185 | 63% | 63% | 64% | 63% |
| SHP-91 | 9, 10 | hsa-miR-574-5p, hsa-miR-664 | 54% | 50% | 76% | 63% |
| SHP-92 | 16, 5 | hsa-miR-486-5p, hsa-miR-106a | 69% | 71% | 55% | 63% |
| SHP-93 | 30, 43 | hsa-miR-93*, hsa-miR-1470 | 68% | 70% | 56% | 63% |
| SHP-94 | 4, 5 | hsa-miR-24, hsa-miR-106a | 63% | 62% | 63% | 63% |
| SHP-95 | 43, 34 | hsa-miR-1470, hsa-miR-106b | 62% | 61% | 64% | 63% |
| SHP-96 | 43, 16 | hsa-miR-1470, hsa-miR-486-5p | 75% | 80% | 44% | 62% |
| SHP-97 | 4, 8 | hsa-miR-24, hsa-miR-126 | 59% | 58% | 66% | 62% |
| SHP-98 | 16, 1 | hsa-miR-486-5p, hsa-miR-23a | 67% | 69% | 55% | 62% |
| SHP-99 | 34, 37 | hsa-miR-106b, hsa-let-7d | 64% | 65% | 59% | 62% |
| SHP-100 | 23, 24 | hsa-miR-18b, hsa-miR-374b | 64% | 65% | 57% | 61% |
| SHP-101 | 32, 46 | hsa-miR-363, hsa-miR-1288 | 55% | 51% | 71% | 61% |
| SHP-102 | 17, 25 | hsa-miR-103, hsa-miR-23b | 62% | 62% | 60% | 61% |
| SHP-103 | 21, 46 | hsa-miR-142-5p, hsa-miR-1288 | 54% | 50% | 72% | 61% |
| SHP-104 | 5, 49 | hsa-miR-106a, hsa-miR-24-2* | 60% | 59% | 62% | 61% |
| SHP-105 | 1, 24 | hsa-miR-23a, hsa-miR-374b | 65% | 67% | 54% | 61% |
| SHP-106 | 18, 31 | hsa-miR-423-5p, hsa-miR-324-3p | 59% | 58% | 63% | 61% |
| SHP-107 | 14, 17 | hsa-miR-660, hsa-miR-103 | 60% | 59% | 61% | 60% |
| SHP-108 | 1, 3 | hsa-miR-23a, hsa-miR-150 | 59% | 59% | 62% | 60% |
| SHP-109 | 21, 28 | hsa-miR-142-5p, hsa-miR-30c | 61% | 62% | 59% | 60% |
| SHP-110 | 31, 30 | hsa-miR-324-3p, hsa-miR-93* | 71% | 76% | 45% | 60% |
| SHP-111 | 10, 12 | hsa-miR-664, hsa-miR-451 | 56% | 54% | 66% | 60% |
| SHP-112 | 5, 24 | hsa-miR-106a, hsa-miR-374b | 64% | 66% | 54% | 60% |
| SHP-113 | 37, 44 | hsa-let-7d, hsa-miR-1280 | 38% | 28% | 92% | 60% |
| SHP-114 | 14, 21 | hsa-miR-660, hsa-miR-142-5p | 66% | 69% | 51% | 60% |
| SHP-115 | 23, 12 | hsa-miR-18b, hsa-miR-451 | 62% | 63% | 56% | 60% |
| SHP-116 | 25, 28 | hsa-miR-23b, hsa-miR-30c | 49% | 44% | 75% | 60% |
| SHP-117 | 11, 12 | hsa-miR-185, hsa-miR-451 | 66% | 69% | 50% | 59% |
| SHP-118 | 11, 14 | hsa-miR-185, hsa-miR-660 | 59% | 59% | 59% | 59% |
| SHP-119 | 38, 44 | hsa-miR-320a, hsa-miR-1280 | 44% | 37% | 81% | 59% |
| SHP-120 | 14, 7 | hsa-miR-660, hsa-miR-20a | 57% | 57% | 61% | 59% |
| SHP-121 | 14, 16 | hsa-miR-660, hsa-miR-486-5p | 67% | 71% | 47% | 59% |
| SHP-122 | 32, 21 | hsa-miR-363, hsa-miR-142-5p | 56% | 55% | 63% | 59% |
| SHP-123 | 15, 17 | hsa-miR-320b, hsa-miR-103 | 64% | 67% | 50% | 59% |
| SHP-124 | 12, 32 | hsa-miR-451, hsa-miR-363 | 62% | 63% | 54% | 58% |
| SHP-125 | 13, 17 | hsa-miR-93, hsa-miR-103 | 67% | 70% | 46% | 58% |
| SHP-126 | 7, 21 | hsa-miR-20a, hsa-miR-142-5p | 58% | 58% | 59% | 58% |
| SHP-127 | 4, 7 | hsa-miR-24, hsa-miR-20a | 60% | 61% | 56% | 58% |

Figure 2 con't

| SHP-128 | 5, 8 | hsa-miR-106a, hsa-miR-126 | 62% | 64% | 52% | 58% |
|---|---|---|---|---|---|---|
| SHP-129 | 31, 43 | hsa-miR-324-3p, hsa-miR-1470 | 62% | 63% | 53% | 58% |
| SHP-130 | 8, 11 | hsa-miR-126, hsa-miR-185 | 54% | 52% | 64% | 58% |
| SHP-131 | 34, 1 | hsa-miR-106b, hsa-miR-23a | 68% | 73% | 43% | 58% |
| SHP-132 | 1, 7 | hsa-miR-23a, hsa-miR-20a | 65% | 69% | 47% | 58% |
| SHP-133 | 21, 24 | hsa-miR-142-5p, hsa-miR-374b | 62% | 64% | 52% | 58% |
| SHP-134 | 23, 25 | hsa-miR-18b, hsa-miR-23b | 53% | 51% | 65% | 58% |
| SHP-135 | 14, 32 | hsa-miR-660, hsa-miR-363 | 61% | 63% | 52% | 58% |
| SHP-136 | 24, 49 | hsa-miR-374b, hsa-miR-24-2* | 52% | 50% | 65% | 57% |
| SHP-137 | 21, 34 | hsa-miR-142-5p, hsa-miR-106b | 60% | 62% | 53% | 57% |
| SHP-138 | 13, 16 | hsa-miR-93, hsa-miR-486-5p | 64% | 67% | 48% | 57% |
| SHP-139 | 1, 5 | hsa-miR-23a, hsa-miR-106a | 68% | 73% | 42% | 57% |
| SHP-140 | 13, 14 | hsa-miR-93, hsa-miR-660 | 52% | 49% | 65% | 57% |
| SHP-141 | 32, 7 | hsa-miR-363, hsa-miR-20a | 59% | 60% | 54% | 57% |
| SHP-142 | 21, 23 | hsa-miR-142-5p, hsa-miR-18b | 61% | 63% | 51% | 57% |
| SHP-143 | 5, 7 | hsa-miR-106a, hsa-miR-20a | 63% | 66% | 48% | 57% |
| SHP-144 | 28, 34 | hsa-miR-30c, hsa-miR-106b | 59% | 59% | 54% | 57% |
| SHP-145 | 12, 7 | hsa-miR-451, hsa-miR-20a | 62% | 64% | 49% | 57% |
| SHP-146 | 34, 44 | hsa-miR-106b, hsa-miR-1280 | 57% | 58% | 55% | 56% |
| SHP-147 | 7, 10 | hsa-miR-20a, hsa-miR-664 | 67% | 72% | 40% | 56% |
| SHP-148 | 8, 12 | hsa-miR-126, hsa-miR-451 | 58% | 59% | 53% | 56% |
| SHP-149 | 34, 16 | hsa-miR-106b, hsa-miR-486-5p | 63% | 67% | 44% | 56% |
| SHP-150 | 7, 11 | hsa-miR-20a, hsa-miR-185 | 59% | 61% | 50% | 56% |
| SHP-151 | 8, 10 | hsa-miR-126, hsa-miR-664 | 54% | 54% | 56% | 55% |
| SHP-152 | 24, 25 | hsa-miR-374b, hsa-miR-23b | 55% | 55% | 55% | 55% |
| SHP-153 | 12, 15 | hsa-miR-451, hsa-miR-320b | 56% | 57% | 53% | 55% |
| SHP-154 | 3, 5 | hsa-miR-150, hsa-miR-106a | 64% | 68% | 41% | 55% |
| SHP-155 | 14, 15 | hsa-miR-660, hsa-miR-320b | 53% | 53% | 57% | 55% |
| SHP-156 | 12, 13 | hsa-miR-451, hsa-miR-93 | 57% | 59% | 51% | 55% |
| SHP-157 | 7, 8 | hsa-miR-20a, hsa-miR-126 | 60% | 62% | 47% | 55% |
| SHP-158 | 34, 38 | hsa-miR-106b, hsa-miR-320a | 61% | 65% | 44% | 55% |
| SHP-159 | 23, 45 | hsa-miR-18b, hsa-miR-1908 | 59% | 60% | 48% | 54% |
| SHP-160 | 21, 25 | hsa-miR-142-5p, hsa-miR-23b | 58% | 60% | 48% | 54% |
| SHP-161 | 24, 27 | hsa-miR-374b, hsa-miR-629 | 54% | 54% | 53% | 54% |
| SHP-162 | 13, 21 | hsa-miR-93, hsa-miR-142-5p | 48% | 46% | 61% | 53% |
| SHP-163 | 15, 16 | hsa-miR-320b, hsa-miR-486-5p | 61% | 65% | 42% | 53% |
| SHP-164 | 25, 27 | hsa-miR-23b, hsa-miR-629 | 51% | 51% | 55% | 53% |
| SHP-165 | 26, 27 | hsa-miR-19b, hsa-miR-629 | 45% | 41% | 64% | 53% |
| SHP-166 | 25, 34 | hsa-miR-23b, hsa-miR-106b | 58% | 60% | 44% | 52% |
| SHP-167 | 10, 11 | hsa-miR-664, hsa-miR-185 | 66% | 72% | 32% | 52% |
| SHP-168 | 24, 26 | hsa-miR-374b, hsa-miR-19b | 54% | 55% | 49% | 52% |
| SHP-169 | 28, 37 | hsa-miR-30c, hsa-let-7d | 27% | 15% | 89% | 52% |
| SHP-170 | 23, 26 | hsa-miR-18b, hsa-miR-19b | 45% | 41% | 62% | 52% |

Figure 2 con't

| SHP-171 | 26, 28 | hsa-miR-19b, hsa-miR-30c | 44% | 40% | 64% | 52% |
|---|---|---|---|---|---|---|
| SHP-172 | 27, 28 | hsa-miR-629, hsa-miR-30c | 27% | 15% | 87% | 51% |
| SHP-173 | 8, 13 | hsa-miR-126, hsa-miR-93 | 53% | 54% | 48% | 51% |
| SHP-174 | 11, 13 | hsa-miR-185, hsa-miR-93 | 46% | 44% | 56% | 50% |
| SHP-175 | 25, 26 | hsa-miR-23b, hsa-miR-19b | 51% | 52% | 47% | 50% |
| SHP-176 | 10, 13 | hsa-miR-664, hsa-miR-93 | 49% | 50% | 46% | 48% |
| SHP-177 | 28, 38 | hsa-miR-30c, hsa-miR-320a | 35% | 30% | 64% | 47% |
| SHP-178 | 37, 38 | hsa-let-7d, hsa-miR-320a | 29% | 21% | 71% | 46% |
| SHP-179 | 13, 15 | hsa-miR-93, hsa-miR-320b | 47% | 48% | 41% | 44% |

Figure 3

| SEQ ID NO: | miRNA | Parkinson, median g1 | Healhty Control, median g2 | Platelet, RBC | Level, Blood cells (Parkinson) | Level, Blood cells (Healthy Control) | Level, Platelets (Healthy control) | Level, Red Blood Cells (Healthy control) |
|---|---|---|---|---|---|---|---|---|
| 2 | hsa-miR-1228 | 310 | 696 | P | T | T | T | |
| 12 | hsa-miR-451 | 1225 | 725 | P | T | T | T | |
| 13 | hsa-miR-93 | 3947 | 2341 | P | T | T | T | |
| 24 | hsa-miR-374b | 639 | 407 | P | T | T | H | |
| 44 | hsa-miR-1280 | 3247 | 3150 | P | T | T | T | |
| 19 | hsa-miR-187* | 219 | 355 | P | T | T | L | |
| 39 | hsa-miR-149* | 616 | 735 | P | T | T | L | |
| 40 | hsa-miR-320d | 739 | 756 | P | T | T | H | |
| 9 | hsa-miR-574-5p | 757 | 1364 | P | T | T | M | |
| 29 | hsa-miR-1228* | 1081 | 1680 | P | T | T | M | |
| 42 | hsa-miR-16-2* | 178 | 163 | P | H | H | M | |
| 43 | hsa-miR-1470 | 248 | 293 | P | T | T | M | |
| 45 | hsa-miR-1908 | 972 | 1206 | P | T | T | M | |
| 4 | hsa-miR-24 | 1925 | 1014 | PR | T | T | T | T |
| 5 | hsa-miR-106a | 6699 | 3530 | PR | T | T | T | T |
| 7 | hsa-miR-20a | 3282 | 1803 | PR | T | T | T | T |
| 8 | hsa-miR-126 | 1673 | 927 | PR | T | T | T | T |
| 11 | hsa-miR-185 | 23521 | 13447 | PR | T | T | T | T |
| 16 | hsa-miR-486-5p | 35047 | 21075 | PR | T | T | H | T |
| 17 | hsa-miR-103 | 8526 | 5225 | PR | T | T | T | T |
| 18 | hsa-miR-423-5p | 2629 | 4274 | PR | T | T | T | H |
| 21 | hsa-miR-142-5p | 747 | 468 | PR | T | T | T | H |
| 23 | hsa-miR-18b | 267 | 423 | PR | T | T | H | H |
| 26 | hsa-miR-19b | 10555 | 6734 | PR | T | T | T | T |
| 28 | hsa-miR-30c | 1902 | 1224 | PR | T | T | T | T |
| 32 | hsa-miR-363 | 3999 | 2616 | PR | T | T | H | H |
| 34 | hsa-miR-106b | 10505 | 6910 | PR | T | T | T | T |
| 35 | hsa-miR-144 | 2349 | 1565 | PR | T | T | H | H |
| 37 | hsa-let-7d | 2067 | 2530 | PR | T | T | T | T |
| 38 | hsa-miR-320a | 13017 | 15140 | PR | T | T | T | T |
| 25 | hsa-miR-23b | 3214 | 2050 | PR | T | T | T | L |
| 1 | hsa-miR-23a | 4144 | 1786 | PR | T | T | T | M |
| 14 | hsa-miR-660 | 549 | 326 | PR | T | T | L | T |
| 31 | hsa-miR-324-3p | 693 | 1060 | PR | T | T | L | T |
| 27 | hsa-miR-629 | 171 | 109 | PR | H | L | L | L |
| 10 | hsa-miR-664 | 349 | 199 | PR | T | H | M | H |
| 15 | hsa-miR-320b | 2369 | 1421 | PR | T | T | H | T |

Figure 3 con't

| 30 | hsa-miR-93* | 984 | 1512 | PR | T | T | M | T |
|---|---|---|---|---|---|---|---|---|
| 41 | hsa-miR-222 | 518 | 553 | PR | T | T | H | T |
| 49 | hsa-miR-24-2* | 232 | 268 | PR | T | T | M | L |
| 6 | hsa-miR-361-5p | 456 | 847 | PR | T | T | H | M |
| 33 | hsa-miR-296-5p | 329 | 501 | PR | T | T | M | M |
| 36 | hsa-let-7c | 449 | 534 | PR | T | T | H | M |
| 47 | hsa-miR-125a-5p | 274 | 353 | PR | T | T | H | M |
| 48 | hsa-miR-584 | 177 | 233 | PR | H | T | M | M |
| 51 | hsa-miR-1285 | 337 | 353 | PR | T | T | M | M |
| 3 | hsa-miR-150 | 1439 | 715 | R | T | T |  | H |
| 20 | hsa-miR-9* | 170 | 274 | R | H | T |  | L |

Figure 4

| Seq ID NO: | Stem-Loop Reverse Transcription Primer | Forward Primer | Reverse Primer | Dual-Labeled Probe |
|---|---|---|---|---|
| 1 | X-GGAAATCC | Y-ATCACATTGCCAGGG (SEQ ID NO: 52) | Z | 56-FAM-P-GGAAATCC-3IABLFQ |
| 2 | X-GGGGGGCG | Y-TCACACCTGCCTCG (SEQ ID NO: 53) | Z | 56-FAM-P-GGGGGGCG-3IABLFQ |
| 3 | X-CACTGGTA | Y-TCTCCCAACCCTTGTA (SEQ ID NO: 54) | Z | 56-FAM-P-CACTGGTA-3IABLFQ |
| 4 | X-CTGTTCCT | Y-TGGCTCAGTTCAGCAG (SEQ ID NO: 55) | Z | 56-FAM-P-CTGTTCCT-3IABLFQ |
| 5 | X-CTACCTGC | Y-AAAAGTGCTTACAGTGC (SEQ ID NO: 56) | Z | 56-FAM-P-CTACCTGC-3IABLFQ |
| 6 | X-GTACCCCT | Y-TTATCAGAATCTCCAG (SEQ ID NO: 57) | Z | 56-FAM-P-GTACCCCT-3IABLFQ |
| 7 | X-CTACCTGC | Y-TAAAGTGCTTATAGTGC (SEQ ID NO: 58) | Z | 56-FAM-P-CTACCTGC-3IABLFQ |
| 8 | X-CGCATTAT | Y-TCGTACCGTGAGTAAT (SEQ ID NO: 59) | Z | 56-FAM-P-CGCATTAT-3IABLFQ |
| 9 | X-ACACACTC | Y-TGAGTGTGTGTGTGTGA (SEQ ID NO: 60) | Z | 56-FAM-P-ACACACTC-3IABLFQ |
| 10 | X-TGTAGGCT | Y-TATTCATTTATCCCCAG (SEQ ID NO: 61) | Z | 56-FAM-P-TGTAGGCT-3IABLFQ |
| 11 | X-TCAGGAAC | Y-TGGAGAGAAAGGCAGT (SEQ ID NO: 62) | Z | 56-FAM-P-TCAGGAAC-3IABLFQ |
| 12 | X-AACTCAGT | Y-AAACCGTTACCATTAC (SEQ ID NO: 63) | Z | 56-FAM-P-AACTCAGT-3IABLFQ |
| 13 | X-CTACCTGC | Y-CAAAGTGCTGTTCGTGC (SEQ ID NO: 64) | Z | 56-FAM-P-CTACCTGC-3IABLFQ |
| 14 | X-CAACTCCG | Y-TACCCATTGCATATCG (SEQ ID NO: 65) | Z | 56-FAM-P-CAACTCCG-3IABLFQ |
| 15 | X-TTGCCCTC | Y-AAAAGCTGGGTTGAGA (SEQ ID NO: 66) | Z | 56-FAM-P-TTGCCCTC-3IABLFQ |
| 16 | X-CTCGGGGC | Y-TCCTGTACTGAGCTGC (SEQ ID NO: 67) | Z | 56-FAM-P-CTCGGGGC-3IABLFQ |
| 17 | X-TCATAGCC | Y-AGCAGCATTGTACAGGG (SEQ ID NO: 68) | Z | 56-FAM-P-TCATAGCC-3IABLFQ |
| 18 | X-AAAGTCTC | Y-TGAGGGGCAGAGAGAGCGA (SEQ ID NO: 69) | Z | 56-FAM-P-AAAGTCTC-3IABLFQ |
| 19 | X-GCCCGGT | Y-GGCTACAACACAGGAC (SEQ ID NO: 70) | Z | 56-FAM-P-GCCCGGT-3IABLFQ |
| 20 | X-ACTTTCGG | Y-ATAAAGCTAGATAACC (SEQ ID NO: 71) | Z | 56-FAM-P-ACTTTCGG-3IABLFQ |
| 21 | X-AGTAGTGC | Y-CATAAAGTAGAAAAGC (SEQ ID NO: 72) | Z | 56-FAM-P-AGTAGTGC-3IABLFQ |
| 22 | X-TCAATGAC | Y-TGCAACTTACCTGAGT (SEQ ID NO: 73) | Z | 56-FAM-P-TCAATGAC-3IABLFQ |
| 23 | X-CTAACTGC | Y-TAAGGTGCATCTAGTGC (SEQ ID NO: 74) | Z | 56-FAM-P-CTAACTGC-3IABLFQ |

Figure 4 con't

| | | | | |
|---|---|---|---|---|
| 24 | X-CACTTAGC | Y-ATATAATACAACCTGC (SEQ ID NO: 75) | N | 56-FAM-P-CACTTAGC-3IABLFQ |
| 25 | X-GGTAATCC | Y-ATCACATTGCCAGGG (SEQ ID NO: 76) | N | 56-FAM-P-GGTAATCC-3IABLFQ |
| 26 | X-TCAGTTTT | Y-TGTGCAAATCCATGCAA (SEQ ID NO: 77) | N | 56-FAM-P-TCAGTTTT-3IABLFQ |
| 27 | X-AGTTCTCC | Y-TGGGTTTACGTTGGG (SEQ ID NO: 78) | N | 56-FAM-P-AGTTCTCC-3IABLFQ |
| 28 | X-GCTGAGAG | Y-TGTAAACATCCTACACT (SEQ ID NO: 79) | N | 56-FAM-P-GCTGAGAG-3IABLFQ |
| 29 | X-CACACACC | Y-GTGGGCGGGGCAGGT (SEQ ID NO: 80) | N | 56-FAM-P-CACACACC-3IABLFQ |
| 30 | X-CGGGAAGT | Y-ACTGCTGAGCTAGCAC (SEQ ID NO: 81) | N | 56-FAM-P-CGGGAAGT-3IABLFQ |
| 31 | X-CCAGCAGC | Y-ACTGCCCCAGGTGC (SEQ ID NO: 82) | N | 56-FAM-P-CCAGCAGC-3IABLFQ |
| 32 | X-TACAGATG | Y-AATTGCACGGTATCCA (SEQ ID NO: 83) | N | 56-FAM-P-TACAGATG-3IABLFQ |
| 33 | X-ACAGGATT | Y-AGGGCCCCCCCTCAA (SEQ ID NO: 84) | N | 56-FAM-P-ACAGGATT-3IABLFQ |
| 34 | X-ATCTGCAC | Y-TAAAGTGCTGACAGT (SEQ ID NO: 85) | N | 56-FAM-P-ATCTGCAC-3IABLFQ |
| 35 | X-AGTACATC | Y-TACAGTATAGATGA (SEQ ID NO: 86) | N | 56-FAM-P-AGTACATC-3IABLFQ |
| 36 | X-AACCATAC | Y-TGAGGTAGTAGGTTGT (SEQ ID NO: 87) | N | 56-FAM-P-AACCATAC-3IABLFQ |
| 37 | X-AACTATGC | Y-AGAGGTAGTAGGTTGC (SEQ ID NO: 88) | N | 56-FAM-P-AACTATGC-3IABLFQ |
| 38 | X-TCGCCCTC | Y-AAAAGCTGGGTTGAGA (SEQ ID NO: 89) | N | 56-FAM-P-TCGCCCTC-3IABLFQ |
| 39 | X-GCACAGCC | Y-AGGGAGGGACGGGGGC (SEQ ID NO: 90) | N | 56-FAM-P-GCACAGCC-3IABLFQ |
| 40 | X-TCCTCTCA | Y-AAAAGCTGGGTTG (SEQ ID NO: 91) | N | 56-FAM-P-TCCTCTCA-3IABLFQ |
| 41 | X-ACCCAGTA | Y-AGCTACATCTGGCTA (SEQ ID NO: 92) | N | 56-FAM-P-ACCCAGTA-3IABLFQ |
| 42 | X-TAAAGCAG | Y-CCAATATTACTGTGCT (SEQ ID NO: 93) | N | 56-FAM-P-TAAAGCAG-3IABLFQ |
| 43 | X-CGGGGTGC | Y-GCCCTCCGCCCGTGCA (SEQ ID NO: 94) | N | 56-FAM-P-CGGGGTGC-3IABLFQ |
| 44 | X-GGGTGGCA | Y-TCCCACCGCTG (SEQ ID NO: 95) | N | 56-FAM-P-GGGTGGCA-3IABLFQ |
| 45 | X-GACCAATC | Y-CGGCGGGACGGCGAT (SEQ ID NO: 96) | N | 56-FAM-P-GACCAATC-3IABLFQ |
| 46 | X-TCTCCAGA | Y-TGGACTGCCCTGATC (SEQ ID NO: 97) | N | 56-FAM-P-TCTCCAGA-3IABLFQ |
| 47 | X-TCACAGGT | Y-TCCCTGAGACCCTTTAAC (SEQ ID NO: 98) | N | 56-FAM-P-TCACAGGT-3IABLFQ |
| 48 | X-CTCAGTCC | Y-TTATGGTTTGCCTGGG (SEQ ID NO: 99) | N | 56-FAM-P-CTCAGTCC-3IABLFQ |
| 49 | X-CTGTGTT | Y-TGCCTACTGAGCTGAA (SEQ ID NO: 100) | N | 56-FAM-P-CTGTGTT-3IABLFQ |
| 50 | X-TTTATTGT | Y-CTAATAGTATCTACCAC (SEQ ID NO: 101) | N | 56-FAM-P-TTTATTGT-3IABLFQ |

Figure 4 con't

| 51 | X-AGGTCTCA-3' | Y-TCTGGGCAACAAAGTG (SEQ ID NO: 102) | Z | 56-FAM-P-AGGTCTCA-3IABLFQ |
|---|---|---|---|---|

All sequences in 5' to 3' direction
with X =5'-CTCAACTGGTGTCGTGGAGTCGGCAATTCAGTTGAG (SEQ ID NO: 103)
with Y =5'-ACACTCCAGCTGGG (SEQ ID NO: 104)
with Z =5'-CTCAACTGGTGTCGTGGAGT (SEQ ID NO: 105)
with P =5'-TTCAGTTGAG (SEQ ID NO: 106)
with 56-FAM =5' 6-FAM (Fluorescein)
with 3IABLFQ=Iowa black fluorescein quencher

Figure 5

| Seq ID NO: | Forward Primer | Reverse Primer |
|---|---|---|
| 1 | AGATCACATTGCCAGGGA (SEQ ID NO: 107) | CCAGTTTTTTTTTTGGAAATCC (SEQ ID NO: 158) |
| 2 | GCAGTCACACCTGCCT (SEQ ID NO: 108) | GTCCAGTTTTTTTTTTTTGGG (SEQ ID NO: 159) |
| 3 | GTCTCCCAACCCTTGTAC (SEQ ID NO: 109) | GTCCAGTTTTTTTTTTTTCACTG (SEQ ID NO: 160) |
| 4 | GGCTCAGTTCAGCAGGA (SEQ ID NO: 110) | GTCCAGTTTTTTTTTTTCTGTTC (SEQ ID NO: 161) |
| 5 | GAAAAGTGCTTACAGTGCAG (SEQ ID NO: 111) | GTCCAGTTTTTTTTTTTTCTACCT (SEQ ID NO: 162) |
| 6 | CGCAGTTATCAGAATCTCCAG (SEQ ID NO: 112) | GTCCAGTTTTTTTTTTTTGTACC (SEQ ID NO: 163) |
| 7 | ACAGTAAAGTGCTTATAGTGCA (SEQ ID NO: 113) | GTCCAGTTTTTTTTTTTTTCTACCT (SEQ ID NO: 164) |
| 8 | GCAGTCGTACCGTGAGTAA (SEQ ID NO: 114) | CCAGTTTTTTTTTTTTCGCAT (SEQ ID NO: 165) |
| 9 | TGAGTGTGTGTGTGTGAGT (SEQ ID NO: 115) | CAGGTCCAGTTTTTTTTTTTTTACA (SEQ ID NO: 166) |
| 10 | CGCAGTATTCATTTATCCCCAG (SEQ ID NO: 116) | GGTCCAGTTTTTTTTTTTTGTAG (SEQ ID NO: 167) |
| 11 | GTGGAGAGAAAGGCAGTTC (SEQ ID NO: 117) | GTCCAGTTTTTTTTTTTCAGGA (SEQ ID NO: 168) |
| 12 | GCAGAAACCGTTACCATTACT (SEQ ID NO: 118) | GTCCAGTTTTTTTTTTTTAACTCA (SEQ ID NO: 169) |
| 13 | GCAAAGTGCTGTTCGTG (SEQ ID NO: 119) | GTCCAGTTTTTTTTTTTCTACCT (SEQ ID NO: 170) |
| 14 | AGTACCCATTGCATATCGGA (SEQ ID NO: 120) | GTCCAGTTTTTTTTTTTTCAACTC (SEQ ID NO: 171) |
| 15 | CAGAAAAGTGGGTTGAGA (SEQ ID NO: 121) | CAGTTTTTTTTTTTTGCCCTCT (SEQ ID NO: 172) |
| 16 | GCAGTCCTGTACTGAGCTG (SEQ ID NO: 122) | GGTCCAGTTTTTTTTTTTTCTCG (SEQ ID NO: 173) |
| 17 | AGAGCAGCATTGTACAGG (SEQ ID NO: 123) | GGTCCAGTTTTTTTTTTTCATAG (SEQ ID NO: 174) |
| 18 | TGAGGGGCAGAGAGCGA (SEQ ID NO: 124) | GTCCAGTTTTTTTTTTTAAAGTC (SEQ ID NO: 175) |
| 19 | GGGCTACAACACAGGAC (SEQ ID NO: 125) | GTTTTTTTTTTTTGCCCGGGT (SEQ ID NO: 176) |
| 20 | CGCAGATAAAGCTAGATAACCGA (SEQ ID NO: 126) | GGTCCAGTTTTTTTTTTTTACTTTC (SEQ ID NO: 177) |
| 21 | GCAGCATAAAGTAGAAAAGCAC (SEQ ID NO: 127) | AGGTCCAGTTTTTTTTTTTTAGTAG (SEQ ID NO: 178) |
| 22 | AGTGCAACTTACCTGAGTCA (SEQ ID NO: 128) | GGTCCAGTTTTTTTTTTTTCAATG (SEQ ID NO: 179) |
| 23 | GTAAGGTGCATCTAGTGCAG (SEQ ID NO: 129) | GGTCCAGTTTTTTTTTTTCTAAC (SEQ ID NO: 180) |
| 24 | CGCAGATATAATACAACCTGCT (SEQ ID NO: 130) | GTCCAGTTTTTTTTTTTTCACTTAG (SEQ ID NO: 181) |

Figure 5 con't

| | | |
|---|---|---|
| 25 | AGATCACATTGCCAGGGA (SEQ ID NO: 131) | GGTCCAGTTTTTTTTTTTTTTGGT (SEQ ID NO: 182) |
| 26 | AGTGTGCAAATCCATGCAA (SEQ ID NO: 132) | GGTCCAGTTTTTTTTTTTTTTCAGT (SEQ ID NO: 183) |
| 27 | TGGGTTTACGTTGGGAGA (SEQ ID NO: 133) | GGTCCAGTTTTTTTTTTTTTTAGTTCT (SEQ ID NO: 184) |
| 28 | CAGTGTAAACATCCTACACTCT (SEQ ID NO: 134) | TCCAGTTTTTTTTTTTTTTGCTG (SEQ ID NO: 185) |
| 29 | GCGGGGGCAGGTG (SEQ ID NO: 135) | TCCAGTTTTTTTTTTTTTTCACACA (SEQ ID NO: 186) |
| 30 | ACTGCTGAGCTAGCACT (SEQ ID NO: 136) | CAGTTTTTTTTTTTTTTCGGGAAG (SEQ ID NO: 187) |
| 31 | CTGCCCCAGGTGCT (SEQ ID NO: 137) | GTCCAGTTTTTTTTTTTTTTCCAG (SEQ ID NO: 188) |
| 32 | AGAATTGCACGGTATCCATC (SEQ ID NO: 138) | GGTCCAGTTTTTTTTTTTTTTACAGA (SEQ ID NO: 189) |
| 33 | GGCCCCCCCTCAATC (SEQ ID NO: 139) | GTCCAGTTTTTTTTTTTTTTACAGGA (SEQ ID NO: 190) |
| 34 | GCAGTAAAGTGCTGACAGTG (SEQ ID NO: 140) | GGTCCAGTTTTTTTTTTTTTTATCTG (SEQ ID NO: 191) |
| 35 | CGCAGTACAGTATAGATGATGT (SEQ ID NO: 141) | GGTCCAGTTTTTTTTTTTTTTAGTACA (SEQ ID NO: 192) |
| 36 | GCAGTGAGGTAGTAGGTTGTATG (SEQ ID NO: 142) | GGTCCAGTTTTTTTTTTTTTTAACCA (SEQ ID NO: 193) |
| 37 | AGAGAGGTAGTAGGTTGCAT (SEQ ID NO: 143) | AGGTCCAGTTTTTTTTTTTTTTAACT (SEQ ID NO: 194) |
| 38 | CAGAAAAGCTGGGTTGAGA (SEQ ID NO: 144) | GTTTTTTTTTTTTTTCGCCCTCT (SEQ ID NO: 195) |
| 39 | GGGACGGGGGCTG (SEQ ID NO: 145) | GTCCAGTTTTTTTTTTTTTTGCAC (SEQ ID NO: 196) |
| 40 | GCAGAAAAGCTGGGTTGAG (SEQ ID NO: 146) | TCCAGTTTTTTTTTTTTTTCCTCTC (SEQ ID NO: 197) |
| 41 | CAGAGCTACATCTGGCTACT (SEQ ID NO: 147) | CCAGTTTTTTTTTTTTTTACCCAGT (SEQ ID NO: 198) |
| 42 | CGCAGCCAATATTACTGTG (SEQ ID NO: 148) | TCCAGTTTTTTTTTTTTTTAAAGCAG (SEQ ID NO: 199) |
| 43 | CCCTCCGCCCGTG (SEQ ID NO: 149) | CAGTTTTTTTTTTTTTTCGGGGT (SEQ ID NO: 200) |
| 44 | CCCACCGCTGCCA (SEQ ID NO: 150) | GTCCAGTTTTTTTTTTTTTTGGGT (SEQ ID NO: 201) |
| 45 | GGGGACGGCGATTG (SEQ ID NO: 151) | TCCAGTTTTTTTTTTTTTTGACCA (SEQ ID NO: 202) |
| 46 | TGGACTGCCCTGATCTG (SEQ ID NO: 152) | CCAGTTTTTTTTTTTTTTCTCCAG (SEQ ID NO: 203) |
| 47 | CCCTGAGACCCTTTAACCT (SEQ ID NO: 153) | GTCCAGTTTTTTTTTTTTTTCACAG (SEQ ID NO: 204) |
| 48 | AGTTATGGTTTGCCTGGGA (SEQ ID NO: 154) | GTCCAGTTTTTTTTTTTTTTCTCAGT (SEQ ID NO: 205) |
| 49 | CAGTGCCTACTGAGCTGA (SEQ ID NO: 155) | TCCAGTTTTTTTTTTTTTTCTGTGT (SEQ ID NO: 206) |
| 50 | CGCAGCTAATAGTATCTACCAC (SEQ ID NO: 156) | GGTCCAGTTTTTTTTTTTTTTATTGTG (SEQ ID NO: 207) |
| 51 | TCTGGGCAACAAAGTGAG (SEQ ID NO: 157) | TCCAGTTTTTTTTTTTTTTAGGTCTC (SEQ ID NO: 208) |

Figure 6

| DNA-Fragment add to 3'-end of miRNA | Analysis Technique | Reference |
|---|---|---|
| dC utilizing T4 RNA ligase | microarray | PMID:17105992, Wang, H., et.al., RNA. 151–159 (2007) |
| (bio-dATP)n or (bio-dCTP)n or (bio-dGATP)n or (bio-dAUTP)n with n=1 to 12 utilizing Klenow-Fragment of DNA polymerase I | microarray | PMID:1878666, Vorwerk, S. et al. N. Biotechnol. 25, 142–9 (2008). |
| adding of a complex DNA-tag by ligation | microarray | PMID:21813625, Wyman S.K. et.al., Genome Res. 2011, 21(9):1450-61. |
| TGGAATTCTCGGGTGCCAAGG (SEQ ID NO: 209) | Next Generation Sequencing | Illumina, www.illumina.com |
| 5' P-UCGUAUGCCGUCUUCUGCUUGUidT (SEQ ID NO: 210) | Next Generation Sequencing | Illumina, www.illumina.com |
| AMP-5'p-5'p-CTGTAGGCACCATCAATdi-deoxyC (SEQ ID NO: 211) | Next Generation Sequencing | Illumina, www.illumina.com |
| AMP-5'p-5'p-ATCTCGTATGCCGTCTTCTGCTTGdi-deoxyC (SEQ ID NO: 212) | Next Generation Sequencing | Illumina, www.illumina.com |

Figure 7

| A | B | C | D | E |
|---|---|---|---|---|
| 3' RNA Adapter | 5' RNA Adapter | RT Primer | Small RNA PCR Primer 1 | Small RNA PCR Primer 2 |
| P-UCGUAUGCCGUCUUCUGCUUGUidT (SEQ ID NO: 213) | GUUCAGAGUUCUACAGUCCGACGAUC (SEQ ID NO: 216) | CAAGCAGAAGACGGCATACGA (SEQ ID NO: 219) | CAAGCAGAAGACGGCATACGA (SEQ ID NO: 222) | AATGATACGGCGACCACCGACAGGTTCAGAGTTCTACAGTCCGA (SEQ ID NO: 225) |
| 5'/5rApp/ATCTCGTATGCCGTCTTCTGCTTG/3ddC/ (SEQ ID NO: 214) | GUUCAGAGUUCUACAGUCCGACGAUC (SEQ ID NO: 217) | CAAGCAGAAGACGGCATACGA (SEQ ID NO: 220) | CAAGCAGAAGACGGCATACGA (SEQ ID NO: 223) | AATGATACGGCGACCACCGACAGGTTCAGAGTTCTACAGTCCGA (SEQ ID NO: 226) |
| 5' TGGAATTCTCGGGTGCCAAGG (SEQ ID NO: 215) | 5' GUUCAGAGUUCUACAGUCCGACGAUC (SEQ ID NO: 218) | 5' GCCTTGGCACCCGAGAATTCCA (SEQ ID NO: 221) | CAAGCAGAAGACGGCATACGAGATCGTGATGTGACTGGAGTTCCTTGGCACCCGAGAATTCCA (SEQ ID NO: 224) | AATGATACGGCGACCACCGAGATCTACACGTTCAGAGTTCTACAGTCCGA (SEQ ID NO: 227) | with:

(A) 3' RNA Adapter = DNA fragment added to 3'end of miRNA via ligation reaction (B) 5' RNA Adapter = DNA fragment added to 5'end of miRNA via ligation reaction (C) RT Primer = primer for reverse-transcribing said RNA-DNA hybrid to cDNA (D) Small RNA PCR Primer 1 = universal forward primer for amplifying the cDNAs (E) Small RNA PCR Primer 2 = universal reverse primer for amplifying the cDNAs

MIRNAS AS NON-INVASIVE BIOMARKERS FOR PARKINSON'S DISEASE

RELATED APPLICATIONS

This application is a national stage filing under 35 U.S.C. § 371 of international application number PCT/EP2014/078623, filed Dec. 19, 2014, which claims the benefit of European application number 13198606.9, filed Dec. 19, 2013, each of which is herein incorporated by reference in its entirety.

TECHNICAL FIELD OF THE INVENTION

The present invention relates to a method for diagnosis of Parkinson's disease (PD) based on the determination of expression profiles of at least two miRNAs representative for diagnosis of Parkinson's disease compared to a reference. In addition, the present invention relates to a kit for diagnosis of Parkinson's disease comprising means for determining expression profiles of at least two miRNA representative for Parkinson's disease and at least one reference. Further, the present invention relates to use of said method for diagnosis of Parkinson's disease in a blood sample of a subject.

BACKGROUND OF THE INVENTION

Today, biomarkers play a key role in early diagnosis, risk stratification, and therapeutic management of various diseases. While progress in biomarker research has accelerated over the last 5 years, the clinical translation of disease biomarkers as endpoints in disease management and as the foundation for diagnostic products still poses a challenge.

MicroRNAs (miRNAs) are a new class of biomarkers. They represent a group of small noncoding RNAs that regulate gene expression at the posttranslational level by degrading or blocking translation of messenger RNA (mRNA) targets. So far, miRNAs have been extensively studied in tissue material. It has been found that miRNAs are expressed in a highly tissue-specific manner. Since recently it is known that miRNAs are not only present in tissues but also in body fluid samples, including blood. Nevertheless, the mechanism why miRNAs are found in blood, especially in blood cells or serum/plasma, or their function in these blood fractions is not understood yet.

Various miRNA biomarkers found in tissue material have been proposed to be correlated with certain diseases, e.g. cancer. Especially desirable are non-invasive biomarkers, that allow for quick, easy and cost-effective diagnosis/prognosis, eliminating the need for surgical intervention.

Particularly, the potential role of miRNAs as non-invasive biomarkers for diagnosis of Parkinson's disease has not been systematically evaluated yet. Accordingly, there is still a need for effective methods and kits for the non-invasive diagnosis of Parkinson's disease.

The inventors of the present invention assessed for the first time the expression of miRNAs on a whole-genome level in subjects with Parkinson's disease as non-invasive biomarkers from blood cell preparations. They surprisingly found that miRNAs are significantly dysregulated in blood and blood cell preparations, preferably in blood cell preparation comprising red blood cell, white blood cells or platelets or in platelet preparations of Parkinson's disease subjects and thus, miRNAs are appropriated non-invasive biomarkers for diagnosis of Parkinson's disease. The inventors of the present invention identified single miRNAs which predict diagnosis Parkinson's disease with high specificity, sensitivity and accuracy. The inventors of the present invention also pursued a multiple biomarker strategy, combining at least two miRNA biomarkers to set (or signature) leading to added specificity, sensitivity, accuracy and predictive power.

SUMMARY OF THE INVENTION

In a first aspect, the invention provides a method for diagnosis of Parkinson's disease comprising the steps of:
(i) determining an expression profile of a set comprising at least two miRNAs representative for Parkinson's disease in a blood cell preparation derived from a whole blood sample from a subject, and
(ii) comparing said expression profile to a reference, wherein the comparison of said expression profile to said reference allows for the diagnosis of Parkinson's disease,
(iii) optionally identifying a subject afflicted with Parkinson's disease for therapeutic intervention,
wherein the nucleotide sequences of the miRNAs comprised in the set are selected from the group consisting of SEQ ID NO: 1 to 51.

In a second aspect, the invention provides a set comprising polynucleotides for detecting a set comprising at least two miRNAs for diagnosing Parkinson's disease in a blood cell preparation derived from a whole blood sample from a subject, wherein the nucleotide sequences of the miRNAs comprised in the set are selected from the group consisting of SEQ ID NO: 1 to 51.

In a third aspect, the invention provides the use of set of polynucleotides according to second aspect of the invention for diagnosing Parkinson's disease in a subject In a fourth aspect, the invention provides means for diagnosing Parkinson's disease in a blood cell preparation derived from a whole blood sample of a subject comprising:
(i) a set of at least two polynucleotides according to second aspect of the invention for determining an expression profile of a set comprising at least two miRNAs representative for Parkinson's disease, and/or
(ii) a biochip, a RT-PCT system, a PCR-system, a flow cytometer, a bead-based multiplex system or a next generation sequencing system for determining an expression profile of a set comprising at least two miRNAs representative for Parkinson's disease
wherein the nucleotide sequences of the miRNAs comprised in the set are selected from the group consisting of SEQ ID NO: 1 to 51.

In a fifth aspect, the invention provides a kit for diagnosing Parkinson's disease comprising
(i) means for determining an expression profile according the fourth aspect of the invention, and
(ii) at least one reference, and
(iii) a data carrier
(iv) optionally a whole blood collection tube
(v) optionally means for deriving a blood cell preparation from a whole blood sample In a sixth aspect, the invention provides a set of miRNAs isolated from a blood cell preparation derived from a whole blood sample from a subject for diagnosing Parkinson's disease, wherein the miRNAs are selected from the group consisting of SEQ ID NO: 1 to 51.

In a seventh aspect, the invention relates to the use of a set of miRNAs according to the sixth aspect of the invention for diagnosing Parkinson's disease in a subject.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences. The miRNAs regulate gene expression and are encoded by genes from whose DNA they are transcribed, but miRNAs are not translated into protein (i.e. miRNAs are non-coding RNAs).

The terms "microRNA*" or "miRNA*" refer to miRNA molecules derived from the passenger strand upon processing. In the context of the present invention, the terms "miRNA" and "miRNA*" are interchangeable used. The miRBase (www.mirbase.org) is a well established repository and searchable database of published miRNA sequences and annotation. Because of the conservation of miRNAs among species, for example between humans and other mammals, e.g. animals such as mice, monkey or rat, the polynucleotide(s) of the invention may not only be suitable for detecting and/or quantifying a miRNA(s) of a specific species, e.g. a human miRNA, but may also be suitable for detecting the respective miRNA orthologue(s) in another species, e.g. in another mammal, e.g. in an animal such as mouse or rat.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group (—CH2-OH), producing nucleotides, which are the molecular building blocks of DNA and RNA.

The term "polynucleotide", as used herein, means a molecule of at least 10 nucleotides and of not more than 70 nucleotides covalently linked together. Preferably, the polynucleotides of the present invention are molecules of 10 to 60 nucleotides or 15 to 50 nucleotides in length, more preferably of 17 to 35 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 nucleotides in length, not including optionally spacer elements and/or elongation elements.

The term "sensitivity", as used herein, means a statistical measure of how well a binary classification test correctly identifies a condition, for example how frequently it correctly classifies a heart and cardiovascular system disease into the correct type out of two or more possible types (e.g. heart and cardiovascular system disease type and healthy type). The sensitivity for class A is the proportion of cases that are determined to belong to class "A" by the test out of the cases that are in class "A". A theoretical, optimal prediction can achieve 100% sensitivity (i.e. predict all patients from the sick group as sick).

The term "specificity", as used herein, means a statistical measure of how well a binary classification test correctly identifies a condition, for example how frequently it correctly classifies a heart and cardiovascular system disease into the correct type out of two or more possible types. The specificity for class A is the proportion of cases that are determined to belong to class "not A" by the test out of the cases that are in class "not A". A theoretical, optimal prediction can achieve 100% specificity (i.e. not predict anyone from the healthy group as sick).

The term "accuracy", as used herein, means a statistical measure for the correctness of classification or identification of sample types. The accuracy is the proportion of true results (both true positives and true negatives).

The term "whole blood sample", as used in the context of the present invention, refers to a blood sample originating from a subject containing all blood fractions, including both the cellular (red blood cells, white blood cells, platelets) and the extra-cellar blood fractions (serum, plasma). The "whole blood sample" may be derived by removing blood from a subject by conventional blood collecting techniques, but may also be provided by using previously isolated and/or stored blood samples. Preferably, the whole blood sample from a subject (e.g. human or animal) has a volume of between 0.1 and 20 ml, more preferably of between 0.5 and 15 ml, more preferably between 1 and 10 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 51, 12, 13, 14, 15, 16, 17, 18, 19, or 20 ml. Preferably the whole blood sample is collected by means of a blood collection tube, preferably it is collected in a PAXgene Blood RNA tube, in a Tempus Blood RNA tube, in an EDTA-tube, in a Na-citrate tube, Heparin-tube or in a ACD-tube (Acid citrate dextrose). Preferably, when the whole blood sample is collected the RNA-fraction, especially the miRNA fraction, may be protected/guarded against degradation. For this purpose special collection tubes (e.g. PAXgene Blood RNA tubes from Preanalytix, Tempus Blood RNA tubes from Applied Biosystems) or additives (e.g. RNAlater from Ambion, RNAsin from Promega), that stabilize the RNA fraction and/or the miRNA fraction, may be employed.

The term "blood cell preparation derived from a whole sample", as used in the context of the present invention, refers to a preparation of the whole blood sample, that (substantially) comprises blood cells (red blood cells, white blood cells and/or platelets). Preferably, the blood cell fraction does not contain miRNAs that originate from the extra-cellular fraction (e.g. plasma, serum) of whole blood or does contain miRNAs that originate from the extra-cellular fraction (e.g. plasma, serum) only in minor amounts in order that these do not or do not substantially contribute to the expression profile of the set of at least two miRNAs representative for Parkinson's disease in a blood cell preparation derived from a whole blood sample.

"Blood cell preparations derived from a whole sample" comprising red blood cells, white blood cells and platelets are obtained from processing of whole blood samples collected in PAXgene Blood RNA Tubes, Tempus Blood RNA Tubes, EDTA-tubes, Na-citrate tubes or Heparin-tubes, maintaining or substantially maintaining the initial cellular distribution (blood cell composition) of the whole blood sample. It is preferred that a blood cell preparation derived from a whole sample" comprising red blood, cells white blood cells and platelets is collected e.g. in a PAXgene RNA tube and processed according to the manufacturers protocol resulting in a blood cell preparation, comprising red blood cells and white blood cells and platelets, from which total RNA (comprising the short RNA fraction including the miRNA fraction) is isolated and which is used for determining the expression profile of a subject in said sample according to the present invention.

In another embodiment of the invention the "Blood cell preparations derived from a whole sample" comprising red blood, cells white blood cells or platelets are obtained from processing of whole blood samples collected in PAXgene Blood RNA Tubes, Tempus Blood RNA Tubes, EDTA-tubes, Na-citrate tubes or Heparin-tubes, not necessarily maintaining or not necessarily substantially maintaining the initial cellular distribution (blood cell composition) of the whole blood sample.

The term "platelet preparation derived from a whole sample" as used in the context of the present invention, refers to a blood cell preparation derived from a whole blood sample, that (substantially) comprises platelets (thrombocytes) and which preferably does not contain miRNAs that originate from the red blood cell fraction or from the white blood cell fraction or which does contain miRNAs that originate from the red blood cell fraction or from the white blood cell fraction only in minor amounts in order that these do not or do not substantially contribute to the expression profile of the set of at least two miRNAs representative for Parkinson's disease. Platelet preparations derived from a whole sample are obtained from processing of whole blood samples, that are typically collected in EDTA-tubes, Na-citrate tubes, Heparin-tubes or in ACD-tubes, e.g. by apheresis or platelet-rich-plasma procedures (via red blood cell and white blood cell removal from the whole blood sample by soft spin centrifugation leading to platelet-rich plasma (PRP), optionally followed by leukocyte reduction leading to leukocyte-depleted platelet-rich plasma) or by buffy-coat derived platelet procedures (via red blood cell and plasma removal from the whole blood sample by initial hard spin centrifugation leading to platelet-enriched buffy coat, optionally followed by a second soft spin centrifugation to remove contaminating white and red blood cells leading to platelet (concentrate), optionally followed by leukocyte reduction leading to leukocyte-depleted platelet (concentrate)). Examples of "platelet preparations derived from a whole sample" according to the present invention include platelet-rich-plasma, leukocyte-depleted platelet-rich-plasma, leukocyte-depleted buffy-coat-derived platelets, apheresis-derived platelets or buffy-coat-derived platelets.

The term "total RNA" as used herein relates to the isolated RNA comprising the miRNA-fraction present in the respective blood cell preparations derived from a whole blood sample. Preferably, the total RNA according to the present invention contains the miRNA-fraction or contains a miRNA-enriched fraction of the isolated RNA. The total RNA (comprising the miRNA-fraction or miRNA-enriched fraction) is obtained by lysis (e.g. Trizol) of the blood cells in the blood cell preparation, followed by RNA purification e.g. by phenol/chloroform extraction and/or separation based techniques (e.g. glass fiber filter column, silica-membrane column). Examples of kits for RNA isolation and purification include the miRNeasy Kits (Qiagen), PAXgene Blood miRNA Kit (Qiagen), mirVana PARIS Kit (Life Technologies), PARIS Kit (Life Technologies), Tempus Spin RNA Isolation Kit (Life Technologies).

The term "set comprising at least two miRNAs representative for Parkinson's disease", as used herein, refers to at least two fixed defined miRNAs comprised in a set which are known to be differential (regulated) between subjects (e.g. humans or other mammals) suffering from Parkinson's disease (diseased state) and control subjects (e.g. humans or other mammals) and are thus representative for Parkinson's disease. Said "set comprising at least two miRNAs representative for Parkinson's disease" are preferably selected from the group consisting of SEQ ID NO: 1 to 51 (FIG. 1), or from at least one set of miRNAs listed in FIG. 2.

The term "expression profile" as used in the context of the present invention, represents the determination of the miRNA expression profile or a measure that correlates with the miRNA expression in a sample (e.g. in a blood cell preparation derived from a whole blood sample). By determining the miRNA expression profile, each miRNA is represented by a numerical value. The higher the value of an individual miRNA, the higher is the expression level of said miRNA, or the lower the value of an individual miRNA, the lower is the expression level of said miRNA. The expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX, Milipore Guava) and the like, that allow the analysis of miRNA expression profile in a subject and comparison between samples. Expression profiling techniques are reviewed by Pritchard et. al (Nat Rev Genet. 2012, PMID:22510765) which is incorporated herein by reference in its entirety. The sample material measured by the aforementioned means are derived from a blood cell preparation and may be a total RNA, labeled total RNA, amplified total RNA, cDNA, labeled cDNA, amplified cDNA, miRNA, labeled miRNA, amplified miRNA or any derivatives that may be generated from the aforementioned RNA/DNA species.

The "expression profile", as used herein, relates to a collection of expression profiles of at least two miRNAs, preferably of least 2, 3, 4, 5, 6, 7, 8, 9, 10, 51, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 51 or more miRNAs.

The term "platelet-derived miRNA" as used in the context of the present invention refers to a miRNA that is expressed in platelets. This does not necessarily mean that this platelet-miRNA is exclusively expressed in platelets and not in any other blood cells, in other cells, in other body fluids or in tissue.

The term "determining an expression profile in (from) a blood cell preparation" as used herein, relates to the determination of the expression profile from the miRNAs present in said blood cell preparation, therefore it is a measure that correlates with the miRNAs present in said blood cell preparation. Herein, all steps or transformations required to bring the blood cell preparation into a form which allows to record the expression profile by any convenient means (e.g. nucleic acid hybridisation, nucleic acid amplification, polymerase extension, mass spectroscopy, flow cytometry, sequencing) and which are known to the person skilled in the art, are included, e.g. cell-lysis, RNA-isolation, RNA-labeling, polymerase extension of RNA, ligation of RNA reverse-transcription into cDNA, amplification of the cDNA, labelling of cDNA, etc.

The term "diagnosis" as used in the context of the present invention refers to the process of determining a possible disease or disorder and therefore is a process attempting to define the (clinical) condition of a subject. The determination of the expression profile of at least two miRNAs according to the present invention correlates with the (clinical) condition of a subject. Preferably, the diagnosis comprises (i) determining the occurrence/presence of Parkinson's disease, especially in an (very) early phase of the disease (ii) monitoring the course of Parkinson's disease, (iii) staging of Parkinson's disease, (iv) measuring the response of a patient with Parkinson's disease to therapeutic intervention, and/or (v) segmentation of a subject suffering from Parkinson's disease.

Nucleic acid hybridization may be performed using a microarray/biochip or in situ hybridization. For nucleic acid hybridization, for example, the polynucleotides (probes) according to the present invention with complementarity to the corresponding miRNAs to be detected are e.g. attached to a solid phase to generate a microarray/biochip (e.g. 51 polynucleotides (probes) which are complementary to the 51 miRNAs having SEQ ID NO: 1 to 51. Said microarray/biochip is then incubated with a sample containing miRNAs, isolated (e.g. extracted) from a blood cell preparation derived from a whole blood sample from a subject, which may be labelled, e.g. fluorescently labelled, or unlabelled. Quantification of the expression level of the miRNAs may then be carried out e.g. by direct read out of a label or by additional manipulations, e.g. by use of a enzymatic reaction. Alternatively, the polynucleotides which are at least partially complementary (e.g. a set of chimeric polynucleotides with each a first stretch being complementary to a set of miRNA sequences and a second stretch complementary to capture probes bound to a solid surface (e.g. beads, Luminex beads)) to miRNAs having SEQ ID NO: 1 to 51 are contacted with said sample containing miRNAs in solution to hybridize. Afterwards, the hybridized duplexes are pulled down to the surface and successfully captured miRNAs are quantitatively determined (e.g. FlexmiR-assay, FlexmiR v2 detection assays from Luminex, Fireplex from Firefly Bioworks.

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 10 miRNAs), whereas high-throughput RT-PCR technologies (e.g. OpenArray from Applied Biosystems, Smart-PCR from Wafergen, Biomark System from Fluidigm) are also able to measure large sets (e.g a set of 10, 20, 30, 50, 80, 100, 200 or more) to all known miRNAs in a high parallel fashion. RT-PCR is particularly suitable for detecting low abandoned miRNAs.

The aforesaid real time polymerase chain reaction (RT-PCR) may include the following steps: (i) extracting the total RNA from a blood cell preparation derived from a whole blood sample of a subjects, (ii) obtaining cDNA samples by RNA reverse transcription (RT) reaction using universal or miRNA-specific primers; (iii) designing miRNA-specific cDNA primers and to amplify the cDNA via polymerase chain reaction (PCR), (iv) adding a fluorescent dye (e.g. SYBR Green) or a fluorescent probe (e.g. Taqman probe) probe to conduct PCR, and (v) detecting the miRNA(s) level in the sample. In Step (i) the isolation and/or extraction of RNA may be omitted in cases where the RT-PCR is conducted directly from the miRNA-containing sample. Kits for determining a miRNA expression profile by real time polymerase chain reaction (RT-PCR) are e.g. from Life Technologies, Applied Biosystems, Ambion, Roche, Qiagen, Invitrogen, SABiosciences, Exiqon.

The term "subject", as used in the context of the present invention, means a patient or individual or mammal suspected to be afflicted by Parkinson's disease. The patient may be diagnosed to be afflicted by Parkinson's disease, i.e. diseased, or may be diagnosed to be not afflicted by Parkinson's disease, i.e. healthy. The subject may also be diagnosed to be afflicted by a specific form of Parkinson's disease. The subject may further be diagnosed to develop Parkinson's disease or a specific form of Parkinson's disease as the inventors of the present invention surprisingly found that miRNAs representative for Parkinson's disease are already present in the blood cell preparation derived from a whole blood sample or in a platelet preparation at an the early stage of Parkinson's disease. It should be noted that a subject that is diagnosed as being healthy, i.e. not suffering from Parkinson's disease or from a specific form of Parkinson's disease, may possibly suffer from another disease not tested/known.

The term "Parkinson's disease (PD)", as used herein refers to a group of conditions called motor system disorders, which are the result of the loss of dopamine-producing brain cells. Primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. There are currently no blood or laboratory tests that have been proven to help in diagnosing PD. Therefore, the diagnosis is based on medical history and a neurological examination. PD can be difficult to diagnose accurately. Doctors may sometimes request brain scans or laboratory tests in order to rule out other diseases. At present, there is no cure for PD, but a variety of medications provide dramatic relief from the symptoms. To overcome current roadblocks to better clinical trial design through improved assessment of Parkinson's Disease progression across the disease spectrum, there is an urgent unmet need for new diagnostic and progression biomarkers in PD.

An overview of the miRNAs that are found to be significantly differentially regulated in blood cell preparations derived from a whole sample and that are suitable for diagnosis of Parkinson's disease are provided in FIG. 1 (SEQ ID NO: 1-51).

An exemplarily approach to arrive at miRNA sets (signatures) that are useful in the diagnosis of Parkinson's disease is summarized below:

Step 1: total RNA (comprising the miRNA fraction) is extracted from the blood cell preparations derived from a whole sample using suitable kits and/or purification methods.

Step 2: From the respective samples the expression profile of at least two miRNAs, e.g. selected from the group consisting of SEQ ID NO: 1 to SEQ ID NO: 51, is measured using experimental techniques. These techniques include but are not limited to hybridisation based approaches, amplification methods (PCR, RT-PCR, qPCR), sequencing, next generation sequencing, flow cytometry and/or mass spectroscopy.

Step 3: In order to gather information on the diagnostic value and the redundancy of each of the single miRNA biomarkers, mathematical methods are applied. These methods include, but are not restricted to, basic mathematic approaches (e.g. Fold Quotients, Signal to Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in Step 3) together with other experimental parameters (e.g. signal intensity, fold change, miRNA origin) is used to estimate for each miRNA biomarker the diagnostic content and the analytical quality. Usually, however, this diagnostic value is too small to get a highly accurate diagnosis with accuracy rates, specificities and sensitivities beyond the 80-90% barrier. The diagnostic content of the single miRNAs representative for diagnosing Parkinson's disease is exemplarily listed in FIG. 1.

Step 5: In order to increase the performance for diagnosing of subjects suffering from Parkinson's disease, more than one biomarker may be employed. Thus statistical learning/machine learning/bioinformatics/computational approaches are applied for set selection in order to select at least two miRNA biomarker (e.g. comprising miRNAs SEQ ID NO: 1 to 51 or comprising at least one set of miRNAs listed in FIG. 2) to result in a tailored set (signature) of miRNA biomarkers suitable for diagnosis of Parkinson's disease. These techniques include, but are not restricted to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers is then used to carry out a diagnosis of Parkinson's disease. To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning (Step 6) an algorithm or mathematical function for diagnosing Parkinson's disease is obtained. This algorithm or mathematical function is applied to a miRNA expression profile for diagnosis of Parkinson's disease.

In a first aspect, the present invention relates to a method for diagnosing Parkinson's disease comprising the steps of:
(i) determining an expression profile of a set comprising at least two miRNAs representative for Parkinson's disease in a blood cell preparation derived from a whole blood sample from a subject, and
(ii) comparing said expression profile to a reference, wherein the comparison of said expression profile to said reference allows for the diagnosis of Parkinson's disease,
(iii) optionally identifying a subject afflicted with Parkinson's disease for therapeutic intervention,
wherein the nucleotide sequences of the miRNAs comprised in the set are selected from the group consisting of SEQ ID NO: 1 to 51.

Optionally said method for diagnosing Parkinson's disease comprises a further step:
(iv) optionally subjecting said subject identified to be afflicted with Parkinson's disease to therapeutic intervention selected from the group consisting of medication (drug treatment), surgical intervention or lifestyle modification.

The term microRNA expression profile as used herein represents the expression profile of a collection of at least 2 miRNAs comprised in the set, preferably at least, 3, 4, 5, 6, 7, 8, 9, 10, 1, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 51 miRNAs, wherein the nucleic acid sequence of said miRNAs is selected from the group consisting of SEQ ID NO. 1 to SEQ ID NO: 51.

According to the present invention the expression profile is determined in a blood cell preparation derived from a whole blood sample of a subject, preferably a human subject. Herein, the whole blood sample is collected from the subject by conventional blood draw techniques. Blood collection tubes suitable for collection of whole blood include EDTA-, Na-citrate-, ACD-, Heparin-, PAXgene Blood RNA-, Tempus Blood RNA-tubes. According to the present invention the collected whole blood sample, which intermediately may be stored before use, is processed to result in a blood cell preparation of whole blood. This is achieved by separation of the blood cell fraction (the cellular fraction of whole blood) from the serum/plasma fraction (the extracellular fraction of whole blood). It is preferred, that the blood cell preparation derived from the whole blood sample comprises red blood cells, white blood cells or platelets, it is more preferred that the blood cell preparation derived from the whole blood sample comprises red blood cells, white blood cells and platelets.

Preferably, the total RNA, including the miRNA fraction, or the miRNA-fraction is isolated from said blood cells present within said blood cell preparations. Kits for isolation of total RNA including the miRNA fraction or kits for isolation of the miRNA-fraction are well known to those skilled in the art, e.g. miRNeasy-kit (Qiagen, Hilden, Germany), Paris-kit (Life Technologies, Weiterstadt, Germany). The miRNA-profile of said set comprising at least two miRNAs listed in FIG. 1 (SEQ ID NO. 1 to SEQ ID NO: 51) is then determined from the isolated RNA derived from the blood cells present within the blood cell preparation of whole blood. Alternatively, the miRNA-profile of said set comprising at least two miRNAs listed in FIG. 1 (SEQ ID NO. 1 to SEQ ID NO: 51) may be determined directly from the blood cell preparation derived from the whole blood sample without the need for isolation of RNA.

The determination of the expression profile may be by any convenient means for determining miRNAs or miRNA profiles. A variety of techniques are well known to those skilled in the art, e.g. nucleic acid hybridisation, nucleic acid amplification, sequencing, mass spectroskopy, flow cytometry based techniques or combinations thereof. According to the present invention the expression profile is determined from at least two miRNAs with nucleotide sequences selected from the group consisting of SEQ ID NO: 1 to SEQ ID NO: 51, which are listed in FIG. 1.

Preferably the nucleic sequences of the at least two miRNAs comprised in the set when determining an expression profile in a blood cell preparation derived from a whole blood sample have SEQ ID NO: 1 and SEQ ID NO: 2, the nucleic sequences of the at least two miRNAs comprised in the set have SEQ ID NO: 1 and SEQ ID NO: 3, the nucleic sequences of the at least two miRNAs comprised in the set have SEQ ID NO: 1 and SEQ ID NO: 4, the nucleic sequences of the at least two miRNAs comprised in the set have SEQ ID NO: 1 and SEQ ID NO: 5, the nucleic sequences of the at least two miRNAs comprised in the set have SEQ ID NO: 1 and SEQ ID NO: 6, the nucleic sequences of the at least two miRNAs comprised in the set have SEQ ID NO: 1 and SEQ ID NO: 7, the nucleic sequences of the at least two miRNAs comprised in the set have SEQ ID NO: 1 and SEQ ID NO: 8, the nucleic sequences of the at least two miRNAs comprised in the set have SEQ ID NO: 1 and SEQ ID NO: 9, the nucleic sequences of the at least two miRNAs comprised in the set have SEQ ID NO: 1 and SEQ ID NO: 10, the nucleic sequences of the at least two miRNAs comprised in the set have SEQ ID NO: 2 and SEQ ID NO: 3, the nucleic sequences of the at least two miRNAs comprised in the set have SEQ ID NO: 2 and SEQ ID NO: 4, the nucleic sequences of the at least two miRNAs comprised in the set have SEQ ID NO: 2 and SEQ ID NO: 5, the nucleic sequences of the at least two miRNAs comprised in the set have SEQ ID NO: 2 and SEQ ID NO: 6, the nucleic sequences of the at least two miRNAs comprised in the set have SEQ ID NO: 2 and SEQ ID NO: 7, the nucleic sequences of the at least two miRNAs comprised in the set have SEQ ID NO: 2 and SEQ ID NO: 8, the nucleic sequences of the at least two miRNAs comprised in the set have SEQ ID NO: 2 and SEQ ID NO: 9, the nucleic sequences of the at least two miRNAs comprised in the set have SEQ ID NO: 2 and SEQ ID NO: 10, the nucleic sequences of the at least two miRNAs comprised in the set have SEQ ID NO: 3 and SEQ ID NO: 4, the nucleic sequences of the at least two miRNAs comprised in the set have SEQ ID NO: 3 and SEQ ID NO: 5, the nucleic sequences of the at least two miRNAs comprised in the set have SEQ ID NO: 3 and SEQ ID NO: 6, the nucleic sequences of the at least two miRNAs comprised in the set have SEQ ID NO: 3 and SEQ ID NO: 7, the nucleic sequences of the at least two miRNAs comprised in the set have SEQ ID NO: 3 and SEQ ID NO: 8, the nucleic sequences of the at least two miRNAs comprised in the set have SEQ ID NO: 3 and SEQ ID NO: 9, the nucleic sequences of the at least two miRNAs comprised in the set have SEQ ID NO: 3 and SEQ ID NO: 10, the nucleic sequences of the at least two miRNAs comprised in the set have SEQ ID NO: 4 and SEQ ID NO: 5, the nucleic sequences of the at least two miRNAs comprised in the set have SEQ ID NO: 4 and SEQ ID NO: 6, the nucleic sequences of the at least two miRNAs comprised in the set have SEQ ID NO: 4 and SEQ ID NO: 7, the nucleic sequences of the at least two miRNAs comprised in the set have SEQ ID NO: 4 and SEQ ID NO: 8, the nucleic sequences of the at least two miRNAs comprised in the set have SEQ ID NO: 4 and SEQ ID NO: 9, the nucleic sequences of the at least two miRNAs comprised in the set have SEQ ID NO: 4 and SEQ ID NO: 10, the nucleic sequences of the at least two miRNAs comprised in the set have SEQ ID NO: 5 and SEQ ID NO: 6, the nucleic sequences of the at least two miRNAs comprised in the set have SEQ ID NO: 5 and SEQ ID NO: 7, the nucleic sequences of the at least two miRNAs comprised in the set have SEQ ID NO: 5 and SEQ ID NO: 8, the nucleic sequences of the at least two miRNAs comprised in the set have SEQ ID NO: 5 and SEQ ID NO: 9, the nucleic sequences of the at least two miRNAs comprised in the set have SEQ ID NO: 5 and SEQ ID NO: 10, the nucleic sequences of the at least two miRNAs comprised in the set have SEQ ID NO: 6 and SEQ ID NO: 7, the nucleic sequences of the at least two miRNAs comprised in the set have SEQ ID NO: 6 and SEQ ID NO: 8, the nucleic sequences of the at least two miRNAs comprised in the set have SEQ ID NO: 6 and SEQ ID NO: 9, the nucleic sequences of the at least two miRNAs comprised in the set have SEQ ID NO: 6 and SEQ ID NO: 10, the nucleic sequences of the at least two miRNAs comprised in the set have SEQ ID NO: 1 and SEQ ID NO: 8, the nucleic sequences of the at least two miRNAs comprised in the set have SEQ ID NO: 7 and SEQ ID NO: 9, the nucleic sequences of the at least two miRNAs comprised in the set have SEQ ID NO: 7 and SEQ ID NO: 10, the nucleic sequences of the at least two miRNAs comprised in the set have SEQ ID NO: 8 and SEQ ID NO: 9, the nucleic sequences of the at least two miRNAs comprised in the set have SEQ ID NO: 8 and SEQ ID NO: 10, or the nucleic sequences of the at least two miRNAs comprised in the set have SEQ ID NO: 9 and SEQ ID NO: 10.

The expression profile determined in step (i) above is then compared in step (ii) to a reference, wherein the reference is derived from the same set comprising at least two miRNAs representative for Parkinson's Disease. The reference may be derived from a collection of expression profiles derived from at least two reference subjects or alternatively, the reference may represent a mathematical function, an algorithm, a classifier or a numeric threshold that was derived from a plurality of reference expression profiles derived from at least two reference subjects. It is preferred that the reference subjects are human subjects. It is preferred that the reference subjects belong to one of at least two groups of clinical conditions which are relevant for diagnosis of Parkinson's Disease and which are to be diagnosed according to the method of the present invention. For example, in early diagnosis of Parkinson's disease, the two groups of clinical conditions may be a) being not afflicted with Parkinson's Disease (i.e. healthy control) and b) being afflicted with Parkinson's Disease, therefore the corresponding reference subjects may be a) subjects not suffering from PD (i.e. healthy control subject) and b) subjects suffering from PD (disease subject). Furthermore, when diagnosing response to therapeutic intervention or monitoring therapeutic intervention or stratifying PD patients, the two groups of clinical conditions may be a) PD subjects positively responding to therapeutic intervention and b) PD subjects not (or less or adversely) responding to therapeutic intervention, therefore the corresponding reference subjects may be a) subjects suffering from PD with positive response to therapeutic intervention (positive response subject) and b) subjects suffering from PD with negative (less or adverse) response to therapeutic intervention (negative response subjects). Preferably, the expression profile and the reference expression profile originate from the sample type of sample, preferably from a blood cell preparation derived from a whole blood sample.

According to the present invention the comparison of the expression profile of a subject to the reference in step (ii) allows for the diagnosis of Parkinson's Disease. Herein, the comparison will allow to diagnose that the subject belongs or that there is a statistical likelihood (or probability) that the subject belongs to one of at least two groups of clinical conditions (e.g. being not afflicted with PD vs. being afflicted with PD or being afflicted with PD with positive response to therapeutic treatment vs. being afflicted with PD with negative (or less or adverse) response to therapeutic treatment) which are relevant for diagnosis of Parkinson's Disease.

Optionally, the method of the present invention comprises a step (iii) for identifying a subject afflicted with Parkinson's disease for therapeutic intervention. Herein, subjects that are afflicted or diagnosed with PD are identified to be eligible for therapeutic treatment, e.g. identified for application of first line treatment, identified for application of second line treatment, identified for change of treatment regime. Therapeutic intervention include medication (e.g. dopaminergic drugs, Carbidopa-levodopa, dopamine agonists, MAO-B inhibitors, Catechol O-methyltransferase (COMT) inhibitors, Anticholinergics, Amantadine), surgical therapy (for those PD patients who have exhausted medical treatment of PD tremor or who suffer profound motor fluctuations) or lifestyle modifications such as getting more rest and more exercise.

Thus, optionally, the method of the present invention comprises a step (iv) for subjecting a subject which has been identified to be afflicted with Parkinson's disease to therapeutic intervention selected from the group consisting of medication (drug treatment), surgical intervention or lifestyle modification, preferably to medication (e.g. dopaminergic drugs, Carbidopa-levodopa, dopamine agonists, MAO-B inhibitors, Catechol O-methyltransferase (COMT) inhibitors, Anticholinergics, Amantadine), surgical therapy (for those PD patients who have exhausted medical treatment of PD tremor or who suffer profound motor fluctuations) or lifestyle modifications such as getting more rest and more exercise.

It is particularly preferred that the set of miRNAs comprises at least one set of miRNAs listed in FIG. 2. Thus, particularly preferred when determining the expression profile in a blood cell preparation derived from a whole blood sample from a subject the set of miRNAs comprises a set of miRNAs with high diagnostic discrimination power for diagnosing PD as listed in FIG. 2, selected from the group consisting of SHP-1 to SHP-179. Further particularly preferred, when determining the expression profile in a blood cell preparation derived from a whole blood sample from a subject, the set of miRNAs comprises a set of miRNAs with high diagnostic discrimination power for diagnosing PD listed in FIG. 2, such as SHP-1 (comprising SEQ ID NO: 19, SEQ ID NO: 22 resulting in 89% accuracy, 88% specificity, 94% sensitivity), SHP-2 (comprising SEQ ID NO: 1, SEQ ID NO: 2 resulting in 86% accuracy, 86% specificity, 86% sensitivity), SHP-3 (comprising SEQ ID NO: 2, SEQ ID NO: 3 resulting in 77% accuracy, 74% specificity, 96% sensitivity), SHP-4 (comprising SEQ ID NO: 20, SEQ ID NO: 22 resulting in 84% accuracy, 84% specificity, 85% sensitivity), SHP-5 (comprising SEQ ID NO: 19, SEQ ID NO: 2 resulting in 85% accuracy, 86% specificity, 83% sensitivity), SHP-6 (comprising SEQ ID NO: 19, SEQ ID NO: 6 resulting in 82% accuracy, 82% specificity, 84% sensitivity), SHP-7 (comprising SEQ ID NO: 18, SEQ ID NO: 4 resulting in 73% accuracy, 69% specificity, 93% sensitivity), SHP-8 (comprising SEQ ID NO: 47, SEQ ID NO: 1 resulting in 73% accuracy, 69% specificity, 92% sensitivity), SHP-9 (comprising SEQ ID NO: 20, SEQ ID NO: 31 resulting in 78% accuracy, 77% specificity, 83% sensitivity), SHP-10 (comprising SEQ ID NO: 17, SEQ ID NO: 19 resulting in 80% accuracy, 80% specificity, 80% sensitivity), SHP-11 (comprising SEQ ID NO: 18, SEQ ID NO: 20 resulting in 78% accuracy, 77% specificity, 83% sensitivity), SHP-12 (comprising SEQ ID NO: 33, SEQ ID NO: 20 resulting in 74% accuracy, 72% specificity, 87% sensitivity), SHP-13 (comprising SEQ ID NO: 2, SEQ ID NO: 4 resulting in 82% accuracy, 83% specificity, 75% sensitivity), SHP-14 (comprising SEQ ID NO: 16, SEQ ID NO: 19 resulting in 76% accuracy, 75% specificity, 83% sensitivity), SHP-15 (comprising SEQ ID NO: 6, SEQ ID NO: 20 resulting in 73% accuracy, 71% specificity, 86% sensitivity), SHP-16 (comprising SEQ ID NO: 2, SEQ ID NO: 9 resulting in 88% accuracy, 93% specificity, 64% sensitivity), SHP-17 (comprising SEQ ID NO: 19, SEQ ID NO: 21 resulting in 73% accuracy, 71% specificity, 84% sensitivity), SHP-18 (comprising SEQ ID NO: 17, SEQ ID NO: 31 resulting in 75% accuracy, 74% specificity, 80% sensitivity), SHP-19 (comprising SEQ ID NO: 18, SEQ ID NO: 19 resulting in 77% accuracy, 77% specificity, 77% sensitivity), SHP-20 (comprising SEQ ID NO: 47, SEQ ID NO: 16 resulting in 72% accuracy, 70% specificity, 83% sensitivity), SHP-21 (comprising SEQ ID NO: 4, SEQ ID NO: 43 resulting in 70% accuracy, 67% specificity, 85% sensitivity), SHP-22 (comprising SEQ ID NO: 22, SEQ ID NO: 9 resulting in 79% accuracy, 81% specificity, 72% sensitivity), SHP-23 (comprising SEQ ID NO: 2, SEQ ID NO: 22 resulting in 84% accuracy, 88% specificity, 63% sensitivity), SHP-24 (comprising SEQ ID NO: 22, SEQ ID NO: 25 resulting in 80% accuracy, 82% specificity, 68% sensitivity), SHP-25 (comprising SEQ ID NO: 17, SEQ ID NO: 20 resulting in 75% accuracy, 75% specificity, 76% sensitivity), SHP-26 (comprising SEQ ID NO: 2, SEQ ID NO: 6 resulting in 84% accuracy, 89% specificity, 62% sensitivity), SHP-27 (comprising SEQ ID NO: 15, SEQ ID NO: 18 resulting in 77% accuracy, 77% specificity, 72% sensitivity), SHP-28 (comprising SEQ ID NO: 19, SEQ ID NO: 20 resulting in 75% accuracy, 75% specificity, 74% sensitivity), SHP-29 (comprising SEQ ID NO: 33, SEQ ID NO: 17 resulting in 67% accuracy, 63% specificity, 86% sensitivity) or SHP-30 (comprising SEQ ID NO: 3, SEQ ID NO: 6 resulting in 68% accuracy, 65% specificity, 82% sensitivity).

Further preferred are sets of the at least two miRNAs selected from the group consisting of SHP-1 to SHP-3 (of FIG. 2), which allow for diagnosing PD with 85-91% balanced Accuracy.

Further preferred are sets of the at least two miRNAs selected from the group consisting of SHP-1 to SHP-11 (of FIG. 2), which allow for diagnosing PD with 80-91% balanced Accuracy.

Further preferred are sets of the at least two miRNAs selected from the group consisting of SHP-1 to SHP-28 (of FIG. 2), which allow for diagnosing PD with 75-91% balanced Accuracy.

Further preferred are sets of the at least two miRNAs selected from the group consisting of SHP-1 to SHP-50 (of FIG. 2), which allow for diagnosing PD with 70-91% balanced Accuracy.

Further preferred are sets of the at least two miRNAs, which allow for diagnosing PD with 92-96% sensitivity, comprising sets of 2 miRNAs, selected from the group consisting of SHP-3, SHP-1, SHP-7, SHP-113, SHP-8 (of FIG. 2). Further preferred are sets of the at least two miRNAs, which allow for diagnosing PD with 85-96% sensitivity, selected from the group consisting of SHP-3, SHP-1, SHP-7, SHP-113, SHP-8, SHP-169, SHP-36, SHP-54, SHP-172, SHP-12, SHP-52, SHP-2, SHP-29, SHP-15, SHP-21, SHP-4 (of FIG. 2). Further preferred are sets of the at least two miRNAs, which allow for diagnosing PD with 80-96% sensitivity, selected from the group consisting of SHP-3, SHP-1, SHP-7, SHP-113, SHP-8, SHP-169, SHP-36, SHP-54, SHP-172, SHP-12, SHP-52, SHP-2, SHP-29, SHP-15, SHP-21, SHP-4, SHP-6, SHP-17, SHP-9, SHP-11, SHP-14, SHP-59, SHP-5, SHP-20, SHP-30, SHP-119, SHP-62, SHP-10, SHP-84, SHP-18, SHP-72 (of FIG. 2). Further preferred are sets of the at least two miRNAs, which allow for diagnosing PD with 55-96% sensitivity, selected from the group consisting of SHP-3, SHP-1, SHP-7, SHP-113, SHP-8, SHP-169, SHP-36, SHP-54, SHP-172, SHP-12, SHP-52, SHP-2, SHP-29, SHP-15, SHP-21, SHP-4, SHP-6, SHP-17, SHP-9, SHP-11, SHP-14, SHP-59, SHP-5, SHP-20, SHP-30, SHP-119, SHP-62, SHP-10, SHP-84, SHP-18, SHP-72, SHP-64, SHP-66, SHP-19, SHP-91, SHP-43, SHP-51, SHP-25, SHP-45, SHP-116, SHP-55, SHP-71, SHP-13, SHP-65 (of FIG. 2).

Further preferred are sets of the at least two miRNAs, which allow for diagnosing PD with 86-93% specificity, selected from the group consisting of SHP-16, SHP-26, SHP-23, SHP-1, SHP-31, SHP-5, SHP-46, SHP-2 (of FIG. 2). Further preferred are sets of the at least two miRNAs, which allow for diagnosing PD with 85-93% specificity, selected from the group consisting of SHP-16, SHP-26, SHP-23, SHP-1, SHP-31, SHP-5, SHP-46, SHP-2, SHP-4, SHP-13, SHP-56, SHP-47, SHP-24, SHP-33, SHP-6, SHP-38, SHP-41, SHP-22, SHP-96, SHP-10, SHP-69 (of FIG. 2). Further preferred are sets of the at least two miRNAs, which allow for diagnosing PD with 80-93% specificity, selected from the group consisting of SHP-16, SHP-26, SHP-23, SHP-1, SHP-31, SHP-5, SHP-46, SHP-2, SHP-4, SHP-13, SHP-56, SHP-47, SHP-24, SHP-33, SHP-6, SHP-38, SHP-41, SHP-22, SHP-96, SHP-10, SHP-69, SHP-34, SHP-9, SHP-27, SHP-37, SHP-11, SHP-19, SHP-44, SHP-49, SHP-40, SHP-75, SHP-35, SHP-110, SHP-28, SHP-79, SHP-25, SHP-14, SHP-32, SHP-63, SHP-85 (of FIG. 2).

It is further preferred that the reference is derived from one or more expression profiles of a set comprising said at least two miRNAs determined from one or more reference subjects.

It is further preferred that the determining of the expression profile includes the reverse-transcription of the nucleotide sequence of the at least two miRNAs comprised in the set into cDNA (complementary DNA). Herein, the RNA-sequence is reverse-transcribed into DNA (e.g. by use of reverse-transcriptase) before the expression profile of said miRNAs is determined. Preferably, the nucleotide sequence of the at least two miRNAs comprised in the set is reverse-transcribed into cDNA when nucleic acid amplification (PCR, RT-PCR), sequencing (next generation sequencing, Sanger sequencing) based techniques are employed in the determination of the miRNA expression profile.

In a further embodiment the determining of an expression profile of a set comprising at least two miRNAs representative for PD (selected from SEQ ID NO: 1 to 51) in step (i) of said method comprises the steps:
(a) reverse-transcribing the miRNAs comprised in the total RNA isolated from the blood cells of the blood cell preparation derived from a whole blood sample into (non-naturally occurring) cDNA
(b) optionally amplifying the cDNA of step (a)
(c) quantifying the optionally amplified cDNA, thereby determining the expression profile of said miRNAs Herein it is preferred that miRNA-specific or universal reverse transcription DNA-primers are used for reverse transcription in step (a). Examples of miRNA-specific reverse transcription primers are listed in column B of FIG. 4, examples of universal reverse transcription primers are Oligo-d(T)-Primers or RT primers listed in column C of FIG. 7. It is further preferred that miRNA-specific forward primer and universal reverse primer or alternatively universal forward and universal reverse primer are used for optionally amplifying the cDNA in step (b). Examples of miRNA-specific forward primer and universal reverse primer are listed in column C and D of FIG. 4, examples of universal forward and universal reverse primer are listed in column D and E of FIG. 7. Further, it is preferred that miRNA-specific forward primer and universal reverse primer (see FIG. 4, column C, D) or alternatively miRNA-specific forward and partially universal reverse primer (see FIG. 5, column B, C) are used for quantifying the optionally amplified cDNA in step (c). It is preferred that the quantifying in step (c) is performed by real-time PCR, nucleic acid hybridization (e.g. microarray) or sequencing (e.g. next generation sequencing) techniques. It is preferred that the quantifying in step (c) by real-time PCR is utilizing dual-labeled hydrolysis probes that make use of the 5'-3' exonuclease activity of polymerase (e.g. Taqman-probes) or DNA-intercalating dyes (e.g. SYBRgreen). Examples of miRNA-specific forward primer and universal reverse primer are listed in column C and D of FIG. 4, examples of miRNA-specific forward and partially universal reverse primer are listed in column B and C of FIG. 5; examples of dual-labeled hydrolysis probes are listed in column E of FIG. 4.

In a still further embodiment the determining of an expression profile of a set comprising at least two miRNAs representative for PD (selected from SEQ ID NO: 1 to 51) in step (i) of said method comprises the steps:
(a) adding a DNA-fragment to the 3'-end of the miRNAs comprised in the total RNA isolated from the blood cells of the blood cell preparation derived from a whole blood sample, thereby forming non-naturally occurring RNA-DNA hybrids
(b) optionally reverse-transcribing said RNA-DNA hybrids to cDNA
(c) quantifying the optionally reverse-transcribed RNA-DNA hybrids, thereby determining the expression profile of said miRNAs Herein it is preferred that DNA-fragments of 1 to 150 nucleotides in length (preferably of 1 to 100 nt, more preferably of 1 to 50 nt, even more preferably of 1 to 30 nt in length) are added in step (a) to the 3'-end of the miRNAs by ligation or by polymerase-based elongation. Examples of said DNA-fragments are listed in FIG. 6 or column A of FIG. 7.

It is preferred that miRNA-specific or universal reverse transcription DNA-primers are used for reverse transcription in step (b). Further, it is preferred that miRNA-specific forward primer and universal reverse primer or alternatively miRNA-specific forward and partially universal reverse primer are used for quantifying the optionally amplified cDNA in step (c). Examples of miRNA-specific reverse transcription primers are listed in column B of FIG. 4, examples of universal reverse transcription primers are oligo-d(T)-Primers or RT primers listed in column C of FIG. 7. It is preferred that the quantifying in step (c) is performed by real-time PCR, nucleic acid hybridization or sequencing (e.g. next generation sequencing) techniques. It is preferred that the quantifying in step (c) by real-time PCR is utilizing dual-labeled hydrolysis probes that make use of the 5'-3' exonuclease activity of polymerase (e.g. Taqman-probes, e.g. FIG. 4, column E) or DNA-intercalating dyes (e.g. SYBRgreen).

In a still further embodiment the determining of an expression profile of a set comprising at least two miRNAs representative for PD (selected from SEQ ID NO: 1 to 51) in step (i) of said method comprises the steps:
(a) adding a RNA-fragment to the 3'-end of the miRNAs comprised in the total RNA isolated from the blood cells of the blood cell preparation derived from a whole blood sample, thereby forming non-naturally occurring RNA-RNA hybrids
(b) optionally reverse-transcribing said RNA-RNA hybrids to cDNA
(c) quantifying the optionally reverse-transcribed RNA-RNA hybrids, thereby determining the expression profile of said miRNAs Herein it is preferred that RNA-fragments of 1 to 150 nucleotides in length (preferably of 1 to 100 nt, more preferably of 1 to 50 nt, even more preferably of 1 to 30 nt in length) are added in step (a) to the 3'-end of the miRNAs preferably by poly(A)-tailing reaction. The reverse-transcription of step (b) is preferably with universal RT-primers, e.g. oligo-d(T)-primers. The quantifying in step (c) is preferably utilizing miRNA-specific forward and partially universal reverse primer, e.g. miRNA-specific forward and partially universal reverse primer as listed in column B and C of FIG. 5.

The inventors of the present invention surprisingly found that a plurality of said miRNAs representative for PD are expressed in platelets, which translates to the finding that the diagnostic information is present or originates from the miRNAs expressed in the platelet fraction of the blood cell preparation. This is somehow surprising or unexpected since the platelets do not contain a nucleus, therefore the platelets are lacking important features (e.g. Dicer) of the miRNA-processing machinery. The inventors of the present invention for the first time found that miRNA-expression arising from platelets may be employed for diagnosing PD. Thus, the method according to present invention further allows for diagnosing a platelet-related component of PD, diagnosing PD, monitoring the progression of PD, determining the platelet activity in a subject affected by PD or monitoring the efficacy of an anti-platelet therapy in a subject affected by PD by determining the expression profile of a set comprising at least two platelet-derived miRNAs representative for PD. Therefore, the expression of platelet-derived miRNAs in a blood cell preparation of whole blood is suitable for diagnosing PD, for diagnosing a platelet-related component of PD, for monitoring the progression of PD, for determining the platelet activity in a subject affected by PD or for monitoring the efficacy of an anti-platelet therapy in a subject affected by PD. In a further embodiment of the present invention, in the method of the present invention, the expression profile of said at least two miRNAs is determined from platelet-derived miRNAs, preferably from miRNAs selected from the group consisting of SEQ ID NO:1-2, SEQ ID NO: 4-19, SEQ ID NO: 21, SEQ ID NO: 23-45, SEQ ID NO: 47-49 or SEQ ID NO: 51. Thus, the method for diagnosing Parkinson's disease comprises the steps of: (i) determining an expression profile of a set comprising at least two platelet-derived miRNAs representative for Parkinson's disease in a blood cell preparation derived from a whole blood sample from a subject, and (ii) comparing said expression profile to a reference, wherein the comparison of said expression profile to said reference allows for the diagnosis of Parkinson's disease, and (iii) optionally identifying a subject afflicted with Parkinson's disease for therapeutic intervention, wherein the nucleotide sequences of the miRNAs comprised in the set are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

It is particularly preferred that when determining the expression profile in a blood cell preparation derived from a whole blood sample from a subject the set of platelet-derived miRNAs comprises at least one set of platelet-derived miRNAs listed in FIG. 2. Particularly preferred when determining the expression profile in a blood cell preparation derived from a whole blood sample from a subject the set of platelet-derived miRNAs comprises a set of platelet-derived miRNAs with high diagnostic discrimination power for diagnosing PD listed in FIG. 2, selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179. Particularly preferred, when determining the expression profile in a blood cell preparation derived from a whole blood sample from a subject, the set of platelet-derived miRNAs comprises a set of platelet-derived miRNAs with high diagnostic discrimination power for diagnosing PD listed in FIG. 2, such as SHP-2 (comprising SEQ ID NO: 1, SEQ ID NO: 2 resulting in 86% accuracy, 86% specificity, 86% sensitivity), SHP-5 (comprising SEQ ID NO: 19, SEQ ID NO: 2 resulting in 85% accuracy, 86% specificity, 83% sensitivity), SHP-6 (comprising SEQ ID NO: 19, SEQ ID NO: 6 resulting in 82% accuracy, 82% specificity, 84% sensitivity), SHP-7 (comprising SEQ ID NO: 18, SEQ ID NO: 4 resulting in 73% accuracy, 69% specificity, 93% sensitivity), SHP-8 (comprising SEQ ID NO: 47, SEQ ID NO: 1 resulting in 73% accuracy, 69% specificity, 92% sensitivity), SHP-10 (comprising SEQ ID NO: 17, SEQ ID NO: 19 resulting in 80% accuracy, 80% specificity, 80% sensitivity), SHP-13 (comprising SEQ ID NO: 2, SEQ ID NO: 4 resulting in 82% accuracy, 83% specificity, 75% sensitivity), SHP-14 (comprising SEQ ID NO: 16, SEQ ID NO: 19 resulting in 76% accuracy, 75% specificity, 83% sensitivity), SHP-16 (comprising SEQ ID NO: 2, SEQ ID NO: 9 resulting in 88% accuracy, 93% specificity, 64% sensitivity), SHP-17 (comprising SEQ ID NO: 19, SEQ ID NO: 21 resulting in 73% accuracy, 71% specificity, 84% sensitivity), SHP-18 (comprising SEQ ID NO: 17, SEQ ID NO: 31 resulting in 75% accuracy, 74% specificity, 80% sensitivity), SHP-19 (comprising SEQ ID NO: 18, SEQ ID NO: 19 resulting in 77% accuracy, 77% specificity, 77% sensitivity), SHP-20 (comprising SEQ ID NO: 47, SEQ ID NO: 16 resulting in 72% accuracy, 70% specificity, 83% sensitivity), SHP-21 (comprising SEQ ID NO: 4, SEQ ID NO: 43 resulting in 70% accuracy, 67% specificity, 85% sensitivity), SHP-26 (comprising SEQ ID NO: 2, SEQ ID NO: 6 resulting in 84% accuracy, 89% specificity, 62% sensitivity), SHP-27 (comprising SEQ ID NO: 15, SEQ ID NO: 18 resulting in 77% accuracy, 77% specificity, 72% sensitivity), SHP-29 (comprising SEQ ID NO: 33, SEQ ID NO: 17 resulting in 67% accuracy, 63% specificity, 86% sensitivity), SHP-32 (comprising SEQ ID NO: 31, SEQ ID NO: 4 resulting in 74% accuracy, 75% specificity, 72% sensitivity), SHP-33 (comprising SEQ ID NO: 2, SEQ ID NO: 5 resulting in 79% accuracy, 82% specificity, 65% sensitivity), SHP-35 (comprising SEQ ID NO: 5, SEQ ID NO: 6 resulting in 75% accuracy, 76% specificity, 70% sensitivity), SHP-36 (comprising SEQ ID NO: 45, SEQ ID NO: 12 resulting in 62% accuracy, 57% specificity, 88% sensitivity), SHP-38 (comprising SEQ ID NO: 4, SEQ ID NO: 6 resulting in 79% accuracy, 82% specificity, 62% sensitivity), SHP-39 (comprising SEQ ID NO: 18, SEQ ID NO: 25 resulting in 69% accuracy, 68% specificity, 74% sensitivity), SHP-40 (comprising SEQ ID NO: 6, SEQ ID NO: 8 resulting in 74% accuracy, 76% specificity, 67% sensitivity), SHP-42 (comprising SEQ ID NO: 6, SEQ ID NO: 7 resulting in 73% accuracy, 73% specificity, 69% sensitivity), SHP-43 (comprising SEQ ID NO: 9, SEQ ID NO: 18 resulting in 66% accuracy, 64% specificity, 76% sensitivity), SHP-44 (comprising SEQ ID NO: 5, SEQ ID NO: 23 resulting in 74% accuracy, 76% specificity, 64% sensitivity), SHP-45 (comprising SEQ ID NO: 16, SEQ ID NO: 18 resulting in 67% accuracy, 65% specificity, 75% sensitivity) or SHP-49 (comprising SEQ ID NO: 18, SEQ ID NO: 21 resulting in 74% accuracy, 76% specificity, 63% sensitivity).

The inventors of the present invention surprisingly found that a plurality of said miRNAs representative for PD are expressed in platelets, which translates to the finding that the diagnostic information is present or originates from the miRNAs expressed in the platelet fraction of the blood cell preparation. This is somehow surprising or unexpected since the platelets do not contain a nucleus, therefore the platelets are lacking important features (e.g. Dicer) of the miRNA-processing machinery. The inventors of the present invention for the first time found that miRNA-expression arising from platelets may be employed for diagnosing PD. Therefore, the expression of miRNAs in a platelet preparation of whole blood is suitable for diagnosing PD. In a further embodiment of the present invention the blood cell preparation derived from a whole blood sample is a platelet-preparation, consisting or substantially consisting of platelets. Preferred platelet-preparation according to the present invention include platelet-rich-plasma, leukocyte-depleted platelet-rich-plasma, leukocyte-depleted buffy-coat-derived platelets, apheresis-derived platelets or buffy-coat-derived platelets.

Preferably the present invention relates to a method for diagnosing Parkinson's disease comprising the steps of: (i) determining an expression profile of a set comprising at least two miRNAs representative for Parkinson's disease in a platelet preparation derived from a whole blood sample from a subject, and (ii) comparing said expression profile to a reference, wherein the comparison of said expression profile to said reference allows for the diagnosis of Parkinson's disease, and (iii) optionally identifying a subject afflicted with Parkinson's disease for therapeutic intervention, wherein the nucleotide sequences of the miRNAs comprised in the set are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

Preferably the nucleic sequences of the at least two miRNAs comprised in the set when determining an expression profile in a platelet preparation derived from a whole blood sample have SEQ ID NO: 1 and SEQ ID NO: 4, the nucleic sequences of the at least two miRNAs comprised in the set have SEQ ID NO: 1 and SEQ ID NO: 5, the nucleic sequences of the at least two miRNAs comprised in the set have SEQ ID NO: 1 and SEQ ID NO: 6, the nucleic sequences of the at least two miRNAs comprised in the set have SEQ ID NO: 1 and SEQ ID NO: 7, the nucleic sequences of the at least two miRNAs comprised in the set have SEQ ID NO: 1 and SEQ ID NO: 8, the nucleic sequences of the at least two miRNAs comprised in the set have SEQ ID NO: 1 and SEQ ID NO: 9, the nucleic sequences of the at least two miRNAs comprised in the set have SEQ ID NO: 1 and SEQ ID NO: 10, the nucleic sequences of the at least two miRNAs comprised in the set have SEQ ID NO: 4 and SEQ ID NO: 5, the nucleic sequences of the at least two miRNAs comprised in the set have SEQ ID NO: 4 and SEQ ID NO: 6, the nucleic sequences of the at least two miRNAs comprised in the set have SEQ ID NO: 4 and SEQ ID NO: 7, the nucleic sequences of the at least two miRNAs comprised in the set have SEQ ID NO: 4 and SEQ ID NO: 8, the nucleic sequences of the at least two miRNAs comprised in the set have SEQ ID NO: 4 and SEQ ID NO: 9, the nucleic sequences of the at least two miRNAs comprised in the set have SEQ ID NO: 4 and SEQ ID NO: 10, the nucleic sequences of the at least two miRNAs comprised in the set have SEQ ID NO: 5 and SEQ ID NO: 6, the nucleic sequences of the at least two miRNAs comprised in the set have SEQ ID NO: 5 and SEQ ID NO: 7, the nucleic sequences of the at least two miRNAs comprised in the set have SEQ ID NO: 5 and SEQ ID NO: 8, the nucleic sequences of the at least two miRNAs comprised in the set have SEQ ID NO: 5 and SEQ ID NO: 9, the nucleic sequences of the at least two miRNAs comprised in the set have SEQ ID NO: 5 and SEQ ID NO: 10, the nucleic sequences of the at least two miRNAs comprised in the set have SEQ ID NO: 6 and SEQ ID NO: 7, the nucleic sequences of the at least two miRNAs comprised in the set have SEQ ID NO: 6 and SEQ ID NO: 8, the nucleic sequences of the at least two miRNAs comprised in the set have SEQ ID NO: 6 and SEQ ID NO: 9, the nucleic sequences of the at least two miRNAs comprised in the set have SEQ ID NO: 6 and SEQ ID NO: 10, the nucleic sequences of the at least two miRNAs comprised in the set have SEQ ID NO: 1 and SEQ ID NO: 8, the nucleic sequences of the at least two miRNAs comprised in the set have SEQ ID NO: 7 and SEQ ID NO: 9, the nucleic sequences of the at least two miRNAs comprised in the set have SEQ ID NO: 7 and SEQ ID NO: 10, the nucleic sequences of the at least two miRNAs comprised in the set have SEQ ID NO: 8 and SEQ ID NO: 9, the nucleic sequences of the at least two miRNAs comprised in the set have SEQ ID NO: 8 and SEQ ID NO: 10, or the nucleic sequences of the at least two miRNAs comprised in the set have SEQ ID NO: 9 and SEQ ID NO: 10.

It is particularly preferred that when determining the expression profile in a platelet preparation derived from a whole blood sample from a subject the set of miRNAs comprises at least one set of platelet-derived miRNAs listed in FIG. 2. Particularly preferred when determining the expression profile in a platelet preparation derived from a whole blood sample from a subject the set of miRNAs comprises a set of platelet-derived miRNAs with high diagnostic discrimination power for diagnosing PD listed in FIG. 2, selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179. Particularly preferred, when determining the expression profile in a platelet preparation derived from a whole blood sample from a subject, the set of miRNAs comprises a set of miRNAs with high diagnostic discrimination power for diagnosing PD listed in FIG. 2, such as SHP-2 (comprising SEQ ID NO: 1, SEQ ID NO: 2 resulting in 86% accuracy, 86% specificity, 86% sensitivity), SHP-5 (comprising SEQ ID NO: 19, SEQ ID NO: 2 resulting in 85% accuracy, 86% specificity, 83% sensitivity), SHP-6 (comprising SEQ ID NO: 19, SEQ ID NO: 6 resulting in 82% accuracy, 82% specificity, 84% sensitivity), SHP-7 (comprising SEQ ID NO: 18, SEQ ID NO: 4 resulting in 73% accuracy, 69% specificity, 93% sensitivity), SHP-8 (comprising SEQ ID NO: 47, SEQ ID NO: 1 resulting in 73% accuracy, 69% specificity, 92% sensitivity), SHP-10 (comprising SEQ ID NO: 17, SEQ ID NO: 19 resulting in 80% accuracy, 80% specificity, 80% sensitivity), SHP-13 (comprising SEQ ID NO: 2, SEQ ID NO: 4 resulting in 82% accuracy, 83% specificity, 75% sensitivity), SHP-14 (comprising SEQ ID NO: 16, SEQ ID NO: 19 resulting in 76% accuracy, 75% specificity, 83% sensitivity), SHP-16 (comprising SEQ ID NO: 2, SEQ ID NO: 9 resulting in 88% accuracy, 93% specificity, 64% sensitivity), SHP-17 (comprising SEQ ID NO: 19, SEQ ID NO: 21 resulting in 73% accuracy, 71% specificity, 84% sensitivity), SHP-18 (comprising SEQ ID NO: 17, SEQ ID NO: 31 resulting in 75% accuracy, 74% specificity, 80% sensitivity), SHP-19 (comprising SEQ ID NO: 18, SEQ ID NO: 19 resulting in 77% accuracy, 77% specificity, 77% sensitivity), SHP-20 (comprising SEQ ID NO: 47, SEQ ID NO: 16 resulting in 72% accuracy, 70% specificity, 83% sensitivity), SHP-21 (comprising SEQ ID NO: 4, SEQ ID NO: 43 resulting in 70% accuracy, 67% specificity, 85% sensitivity), SHP-26 (comprising SEQ ID NO: 2, SEQ ID NO: 6 resulting in 84% accuracy, 89% specificity, 62% sensitivity), SHP-27 (comprising SEQ ID NO: 15, SEQ ID NO: 18 resulting in 77% accuracy, 77% specificity, 72% sensitivity), SHP-29 (comprising SEQ ID NO: 33, SEQ ID NO: 17 resulting in 67% accuracy, 63% specificity, 86% sensitivity), SHP-32 (comprising SEQ ID NO: 31, SEQ ID NO: 4 resulting in 74% accuracy, 75% specificity, 72% sensitivity), SHP-33 (comprising SEQ ID NO: 2, SEQ ID NO: 5 resulting in 79% accuracy, 82% specificity, 65% sensitivity), SHP-35 (comprising SEQ ID NO: 5, SEQ ID NO: 6 resulting in 75% accuracy, 76% specificity, 70% sensitivity), SHP-36 (comprising SEQ ID NO: 45, SEQ ID NO: 12 resulting in 62% accuracy, 57% specificity, 88% sensitivity), SHP-38 (comprising SEQ ID NO: 4, SEQ ID NO: 6 resulting in 79% accuracy, 82% specificity, 62% sensitivity), SHP-39 (comprising SEQ ID NO: 18, SEQ ID NO: 25 resulting in 69% accuracy, 68% specificity, 74% sensitivity), SHP-40 (comprising SEQ ID NO: 6, SEQ ID NO: 8 resulting in 74% accuracy, 76% specificity, 67% sensitivity), SHP-42 (comprising SEQ ID NO: 6, SEQ ID NO: 7 resulting in 73% accuracy, 73% specificity, 69% sensitivity), SHP-43 (comprising SEQ ID NO: 9, SEQ ID NO: 18 resulting in 66% accuracy, 64% specificity, 76% sensitivity), SHP-44 (comprising SEQ ID NO: 5, SEQ ID NO: 23 resulting in 74% accuracy, 76% specificity, 64% sensitivity), SHP-45 (comprising SEQ ID NO: 16, SEQ ID NO: 18 resulting in 67% accuracy, 65% specificity, 75% sensitivity) or SHP-49 (comprising SEQ ID NO: 18, SEQ ID NO: 21 resulting in 74% accuracy, 76% specificity, 63% sensitivity).

In a second aspect, the invention relates to a set comprising polynucleotides for detecting a set comprising at least two miRNAs for diagnosing Parkinson's disease in a blood cell preparation derived from a whole blood sample from a subject, wherein the nucleotide sequences of the miRNAs comprised in the set are selected from the group consisting of SEQ ID NO: 1 to 51.

It is understood that the set comprising polynucleotides of the second aspect of the invention includes and/or comprises the aspects detailed in the method according to the first aspect of the present invention.

It is preferred, that the blood cell preparation derived from the whole blood sample comprises red blood cells, white blood cells or platelets. It is more preferred that the blood cell preparation derived from the whole blood sample comprises red blood cells, white blood cells and platelets.

It is preferred that the at least two miRNAs to be detected by the set comprising polynucleotides have a nucleotide sequences selected from the group consisting of SEQ ID NO: 1 to SEQ ID NO: 51 in a blood cell preparation derived from a whole blood sample, listed in FIG. 1. For further particularly preferred sets of at least two miRNAs to be detected by the set comprising polynucleotides it is referred to the first aspect of the present invention.

It is particularly preferred that the set of miRNAs comprises at least one set of miRNAs listed in FIG. 2, preferably selected from the group consisting of SHP-1 to SHP-179. For further particularly preferred sets of miRNAs with high diagnostic discrimination power for diagnosing PD in a blood cell preparation derived from whole blood it is referred to the first aspect of the present invention.

In a further embodiment of the present invention, in the set comprising polynucleotides of the present invention, the expression profile of said at least two miRNAs is determined from platelet-derived miRNAs, preferably from miRNAs selected from the group consisting of SEQ ID NO:1-2, SEQ ID NO: 4-19, SEQ ID NO: 21, SEQ ID NO: 23-45, SEQ ID NO: 47-49 or SEQ ID NO: 51. For further particularly preferred at least two platelet-derived miRNAs to be detected by the set comprising polynucleotides in a blood cell preparation or for further preferred sets of platelet-derived sets of miRNAs (listed in FIG. 2) to be detected by the set comprising polynucleotides in a blood cell preparation it is referred to the first aspect of the present invention.

In a further embodiment of the second aspect of the present invention the blood cell preparation derived from a whole blood sample is a platelet-preparation, consisting or substantially consisting of platelets. Preferred platelet-preparation according to the present invention include platelet-rich-plasma, leukocyte-depleted platelet-rich-plasma, leukocyte-depleted buffy-coat-derived platelets, apheresis-derived platelets or buffy-coat-derived platelets.

Preferably, the present invention relates to a set comprising polynucleotides for detecting a set comprising at least two miRNAs for diagnosing Parkinson's disease in a platelet preparation derived from a whole blood sample from a subject, wherein the nucleotide sequences of the miRNAs comprised in the set are selected from the group consisting SEQ ID NO:1-2, SEQ ID NO: 4-19, SEQ ID NO: 21, SEQ ID NO: 23-45, SEQ ID NO: 47-49 or SEQ ID NO: 51.

It is further preferred in the set comprising polynucleotides for detecting a set comprising at least two miRNAs for diagnosing Parkinson's disease in a platelet preparation derived from a whole blood sample from a subject, that the set of miRNAs comprises at least one of the set of platelet-derived miRNAs selected from FIG. 2. For further particularly preferred at least two miRNAs to be detected by the set comprising polynucleotides in a platelet preparation or for further preferred sets of platelet-derived sets of miRNAs (listed in FIG. 2) to be detected by the set comprising polynucleotides in a platelet preparation it is referred to the first aspect of the present invention.

It is further preferred that according to the second aspect of the invention said polynucleotides comprised in the set:
(i) are complementary to the miRNAs comprised in said set, or
(ii) are fragments of the polynucleotides comprised in said set or
(iii) are DNA complements according to (i) or DNA fragments according to (ii), or
(iv) have at least 80% sequence identity to the polynucleotide sequences of the complementary polynucleotides comprised in the set according to (i) or of the polynucleotide fragments comprised in the set according to (ii) or of the DNA complement or DNA fragments according to (iii).

It a further embodiment of the second aspect of the invention said polynucleotides comprised in the set are a set of at least two primer pairs for determining an expression profile of a set comprising at least two miRNAs representative for Parkinson's disease in a blood cell preparation derived from a whole blood sample from a subject. It is preferred that said set of at least two primer pairs are specific for determining of at least two miRNAs selected from the group consisting of SEQ ID NO: 1 to 51, or are specific for determining of at least one set of miRNAs listed in FIG. 2. Preferably said set of at least two primer pairs for determining at least two miRNAs selected from the group consisting of SEQ ID NO: 1 to 51 are selected from the primer pairs listed in FIG. 4 or FIG. 5 or FIG. 7.

In a third aspect, the invention relates to the use of set of polynucleotides according to the second aspect of the invention for diagnosing Parkinson's disease in a subject.

It is understood that the use of set of polynucleotides of the third aspect of the invention includes and/or comprises the aspects detailed in set comprising polynucleotides according to the second aspect of the present invention.

In a fourth aspect, the invention relates to means for diagnosing Parkinson's disease in a blood cell preparation derived from a whole blood sample of a subject comprising:
(i) a set of at least two polynucleotides according to the second aspect of the present invention for determining an expression profile of a set comprising at least two miRNAs representative for Parkinson's disease, and/or
(ii) a biochip, a RT-PCR system, a PCR-system, a flow cytometer, a bead-based multiplex system or a next generation sequencing system for determining an expression profile of a set comprising at least two miRNAs representative for Parkinson's disease wherein the nucleotide sequences of the miRNAs comprised in the set are selected from the group consisting of SEQ ID NO: 1 to 51.

It is understood that the means of the fourth aspect of the invention includes and/or comprises the aspects detailed in method according to the first aspect and the aspects detailed in the set comprising polynucleotides according to the second aspect of the present invention.

It is understood that any convenient techniques for determining a miRNA expression profile may be used, including but not limited to, nucleic acid hybridisation, nucleic acid amplification, polymerase extension, sequencing, flow cytometry, mass spectroscopy techniques or any combination thereof.

It is preferred, that in the means for diagnosing PD the blood cell preparation derived from the whole blood sample comprises red blood cells, white blood cells or platelets. It is more preferred that the blood cell preparation derived from the whole blood sample comprises red blood cells, white blood cells and platelets.

It is particularly preferred that the set of miRNAs in the means for diagnosing PD comprises at least one set of miRNAs listed in FIG. 2.

In a fifth aspect, the invention relates to a kit for diagnosing Parkinson's disease comprising
   (i) means for determining an expression profile, and
   (ii) at least one reference, and
   (iii) a data carrier
   (iv) optionally a whole blood collection tube
   (v) optionally means for deriving a blood cell preparation from a whole blood sample It is understood that the means of the fifth aspect of the invention includes and/or comprises the aspects detailed in the method according to the first aspect, the aspects detailed in the set comprising polynucleotides according to the second aspect and the means according to the aspects of the fourth aspect of the present invention.

It is preferred that the means of (i) are means for determining an expression profile of a set comprising at least two miRNAs representative for Parkinson's disease in a blood cell preparation derived from a whole blood sample of a subject, wherein the nucleotide sequences of the miRNAs comprised in the set are selected from the group consisting of SEQ ID NO: 1 to 51.

The kit comprises at least one reference according to the present invention as outlined in the first aspect of the present invention. In a preferred embodiment, the reference may be contained in the data carrier of the kit. In a further preferred embodiment the reference may be a reference sample and/or a reference standard that is included in the kit and which is employed when performing the kit, e.g. in the determining of the expression profile.

The kit comprises a data carrier. Preferably the data carrier is an electronic or a non-electronic data carrier, more preferably it is an electronic data carrier, such as a storage medium.

It is preferred that the data carrier comprised in the kit comprises a guide for use of the kit in diagnosing PD. This guide may include instructions for the doctor and/or the diagnostic laboratory that are involved in the diagnosing of PD. The guide may include a reference according to the present invention.

It is preferred that the data carrier further comprises tools for analysis and evaluation of the determined expression profile(s). These tools may be any tools to assist the doctor and/or the diagnostic laboratory in the diagnosing of PD. Preferably, these tools are software-tools that assist in analysis of the determined expression profile(s) and/or assist in the subsequently diagnosis. The tools for analysis and evaluation may include a reference according to the present invention.

The kit optionally comprises whole blood collection tubes, which are preferably selected from group consisting of EDTA-, Na-citrate-, ACD-, Heparin-, PAXgene Blood RNA-, Tempus Blood RNA-tubes and optionally contains an additive for stabilizing the RNA-fraction.

The kit optionally comprises means for deriving the blood cell preparation from a whole blood sample. These means are preferably for separating and/or isolating of the respective blood cell preparation (e.g. a blood cell preparation comprising white blood cells, red blood cells or platelets, a blood cell preparation comprising white blood cells, red blood cells and platelets, a platelet-preparation) from the whole blood sample. These means may include reagents or consumables for isolating/separating the respective blood cell fraction(s) and/or reagents or consumables for isolating the total RNA (comprising the miRNA-fraction).

It is preferred that the kit comprises means for determining an expression profile according to the fourth aspect of the invention It is preferred that the kit for diagnosing Parkinson's disease, allows for determining the expression profile from a blood cell preparation derived from a whole blood sample comprising platelets, red blood cells and white blood cells or from a blood cell preparation derived from a whole blood sample comprising platelets, red blood cells or white blood cells. It is further preferred that in said kit for diagnosing PD the nucleotide sequences of the at least two miRNAs comprised in the set when determining an expression profile in a blood cell preparation derived from a whole blood sample have SEQ ID NO: 1 and SEQ ID NO: 2, the nucleic sequences of the at least two miRNAs comprised in the set have SEQ ID NO: 1 and SEQ ID NO: 3, the nucleic sequences of the at least two miRNAs comprised in the set have SEQ ID NO: 1 and SEQ ID NO: 4, the nucleic sequences of the at least two miRNAs comprised in the set have SEQ ID NO: 1 and SEQ ID NO: 5, the nucleic sequences of the at least two miRNAs comprised in the set have SEQ ID NO: 1 and SEQ ID NO: 6, the nucleic sequences of the at least two miRNAs comprised in the set have SEQ ID NO: 1 and SEQ ID NO: 7, the nucleic sequences of the at least two miRNAs comprised in the set have SEQ ID NO: 1 and SEQ ID NO: 8, the nucleic sequences of the at least two miRNAs comprised in the set have SEQ ID NO: 1 and SEQ ID NO: 9, the nucleic sequences of the at least two miRNAs comprised in the set have SEQ ID NO: 1 and SEQ ID NO: 10, the nucleic sequences of the at least two miRNAs comprised in the set have SEQ ID NO: 2 and SEQ ID NO: 3, the nucleic sequences of the at least two miRNAs comprised in the set have SEQ ID NO: 2 and SEQ ID NO: 4, the nucleic sequences of the at least two miRNAs comprised in the set have SEQ ID NO: 2 and SEQ ID NO: 5, the nucleic sequences of the at least two miRNAs comprised in the set have SEQ ID NO: 2 and SEQ ID NO: 6, the nucleic sequences of the at least two miRNAs comprised in the set have SEQ ID NO: 2 and SEQ ID NO: 7, the nucleic sequences of the at least two miRNAs comprised in the set have SEQ ID NO: 2 and SEQ ID NO: 8, the nucleic sequences of the at least two miRNAs comprised in the set have SEQ ID NO: 2 and SEQ ID NO: 9, the nucleic sequences of the at least two miRNAs comprised in the set have SEQ ID NO: 2 and SEQ ID NO: 10, the nucleic sequences of the at least two miRNAs comprised in the set have SEQ ID NO: 3 and SEQ ID NO: 4, the nucleic sequences of the at least two miRNAs comprised in the set have SEQ ID NO: 3 and SEQ ID NO: 5, the nucleic sequences of the at least two miRNAs comprised in the set have SEQ ID NO: 3 and SEQ ID NO: 6, the nucleic sequences of the at least two miRNAs comprised in the set have SEQ ID NO: 3 and SEQ ID NO: 7, the nucleic sequences of the at least two miRNAs comprised in the set have SEQ ID NO: 3 and SEQ ID NO: 8, the nucleic sequences of the at least two miRNAs comprised in the set have SEQ ID NO: 3 and SEQ ID NO: 9, the nucleic sequences of the at least two miRNAs comprised in the set have SEQ ID NO: 3 and SEQ ID NO: 10, the nucleic sequences of the at least two miRNAs comprised in the set have SEQ ID NO: 4 and SEQ ID NO: 5, the nucleic sequences of the at least two miRNAs comprised in the set have SEQ ID NO: 4 and SEQ ID NO: 6, the nucleic sequences of the at least two miRNAs comprised in the set have SEQ ID NO: 4 and SEQ ID NO: 7, the nucleic sequences of the at least two miRNAs comprised in the set have SEQ ID NO: 4 and SEQ ID NO: 8, the nucleic sequences of the at least two miRNAs comprised in the set have SEQ ID NO: 4 and SEQ ID NO: 9, the nucleic sequences of the at least two miRNAs comprised in the set have SEQ ID NO: 4 and SEQ ID NO: 10, the nucleic sequences of the at least two miRNAs comprised in the set have SEQ ID NO: 5 and SEQ ID NO: 6, the nucleic sequences of the at least two miRNAs comprised in the set have SEQ ID NO: 5 and SEQ ID NO: 7, the nucleic sequences of the at least two miRNAs comprised in the set have SEQ ID NO: 5 and SEQ ID NO: 8, the nucleic sequences of the at least two miRNAs comprised in the set have SEQ ID NO: 5 and SEQ ID NO: 9, the nucleic sequences of the at least two miRNAs comprised in the set have SEQ ID NO: 5 and SEQ ID NO: 10, the nucleic sequences of the at least two miRNAs comprised in the set have SEQ ID NO: 6 and SEQ ID NO: 7, the nucleic sequences of the at least two miRNAs comprised in the set have SEQ ID NO: 6 and SEQ ID NO: 8, the nucleic sequences of the at least two miRNAs comprised in the set have SEQ ID NO: 6 and SEQ ID NO: 9, the nucleic sequences of the at least two miRNAs comprised in the set have SEQ ID NO: 6 and SEQ ID NO: 10, the nucleic sequences of the at least two miRNAs comprised in the set have SEQ ID NO: 1 and SEQ ID NO: 8, the nucleic sequences of the at least two miRNAs comprised in the set have SEQ ID NO: 7 and SEQ ID NO: 9, the nucleic sequences of the at least two miRNAs comprised in the set have SEQ ID NO: 7 and SEQ ID NO: 10, the nucleic sequences of the at least two miRNAs comprised in the set have SEQ ID NO: 8 and SEQ ID NO: 9, the nucleic sequences of the at least two miRNAs comprised in the set have SEQ ID NO: 8 and SEQ ID NO: 10 or the nucleic sequences of the at least two miRNAs comprised in the set have SEQ ID NO: 9 and SEQ ID NO: 10.

It is further preferred that the kit for diagnosing Parkinson's disease allows for determining the expression profile of a set of miRNAs comprising at least one of the sets of miRNAs listed in FIG. 2. It is even more preferred that in the kit for diagnosing PD in a blood cell preparation derived from a whole blood sample the set of miRNAs comprises at least one set of miRNAs listed in FIG. 2. Thus, particularly preferred in the kit when determining the expression profile in a blood cell preparation derived from a whole blood sample from a subject, it is that the set of miRNAs comprises a set of miRNAs with high diagnostic discrimination power for diagnosing PD (listed in FIG. 2), is selected from the group consisting of SHP-1 to SHP-179. Further it is particularly preferred, when determining the expression profile in a blood cell preparation derived from a whole blood sample from a subject, that the set of miRNAs comprises a set of miRNAs with high diagnostic discrimination power for diagnosing PD listed in FIG. 2, such as SHP-1 (comprising SEQ ID NO: 19, SEQ ID NO: 22 resulting in 89% accuracy, 88% specificity, 94% sensitivity), SHP-2 (comprising SEQ ID NO: 1, SEQ ID NO: 2 resulting in 86% accuracy, 86% specificity, 86% sensitivity), SHP-3 (comprising SEQ ID NO: 2, SEQ ID NO: 3 resulting in 77% accuracy, 74% specificity, 96% sensitivity), SHP-4 (comprising SEQ ID NO: 20, SEQ ID NO: 22 resulting in 84% accuracy, 84% specificity, 85% sensitivity), SHP-5 (comprising SEQ ID NO: 19, SEQ ID NO: 2 resulting in 85% accuracy, 86% specificity, 83% sensitivity), SHP-6 (comprising SEQ ID NO: 19, SEQ ID NO: 6 resulting in 82% accuracy, 82% specificity, 84% sensitivity), SHP-7 (comprising SEQ ID NO: 18, SEQ ID NO: 4 resulting in 73% accuracy, 69% specificity, 93% sensitivity), SHP-8 (comprising SEQ ID NO: 47, SEQ ID NO: 1 resulting in 73% accuracy, 69% specificity, 92% sensitivity), SHP-9 (comprising SEQ ID NO: 20, SEQ ID NO: 31 resulting in 78% accuracy, 77% specificity, 83% sensitivity), SHP-10 (comprising SEQ ID NO: 17, SEQ ID NO: 19 resulting in 80% accuracy, 80% specificity, 80% sensitivity), SHP-11 (comprising SEQ ID NO: 18, SEQ ID NO: 20 resulting in 78% accuracy, 77% specificity, 83% sensitivity), SHP-12 (comprising SEQ ID NO: 33, SEQ ID NO: 20 resulting in 74% accuracy, 72% specificity, 87% sensitivity), SHP-13 (comprising SEQ ID NO: 2, SEQ ID NO: 4 resulting in 82% accuracy, 83% specificity, 75% sensitivity), SHP-14 (comprising SEQ ID NO: 16, SEQ ID NO: 19 resulting in 76% accuracy, 75% specificity, 83% sensitivity), SHP-15 (comprising SEQ ID NO: 6, SEQ ID NO: 20 resulting in 73% accuracy, 71% specificity, 86% sensitivity), SHP-16 (comprising SEQ ID NO: 2, SEQ ID NO: 9 resulting in 88% accuracy, 93% specificity, 64% sensitivity), SHP-17 (comprising SEQ ID NO: 19, SEQ ID NO: 21 resulting in 73% accuracy, 71% specificity, 84% sensitivity), SHP-18 (comprising SEQ ID NO: 17, SEQ ID NO: 31 resulting in 75% accuracy, 74% specificity, 80% sensitivity), SHP-19 (comprising SEQ ID NO: 18, SEQ ID NO: 19 resulting in 77% accuracy, 77% specificity, 77% sensitivity), SHP-20 (comprising SEQ ID NO: 47, SEQ ID NO: 16 resulting in 72% accuracy, 70% specificity, 83% sensitivity), SHP-21 (comprising SEQ ID NO: 4, SEQ ID NO: 43 resulting in 70% accuracy, 67% specificity, 85% sensitivity), SHP-22 (comprising SEQ ID NO: 22, SEQ ID NO: 9 resulting in 79% accuracy, 81% specificity, 72% sensitivity), SHP-23 (comprising SEQ ID NO: 2, SEQ ID NO: 22 resulting in 84% accuracy, 88% specificity, 63% sensitivity), SHP-24 (comprising SEQ ID NO: 22, SEQ ID NO: 25 resulting in 80% accuracy, 82% specificity, 68% sensitivity), SHP-25 (comprising SEQ ID NO: 17, SEQ ID NO: 20 resulting in 75% accuracy, 75% specificity, 76% sensitivity), SHP-26 (comprising SEQ ID NO: 2, SEQ ID NO: 6 resulting in 84% accuracy, 89% specificity, 62% sensitivity), SHP-27 (comprising SEQ ID NO: 15, SEQ ID NO: 18 resulting in 77% accuracy, 77% specificity, 72% sensitivity), SHP-28 (comprising SEQ ID NO: 19, SEQ ID NO: 20 resulting in 75% accuracy, 75% specificity, 74% sensitivity), SHP-29 (comprising SEQ ID NO: 33, SEQ ID NO: 17 resulting in 67% accuracy, 63% specificity, 86% sensitivity) or SHP-30 (comprising SEQ ID NO: 3, SEQ ID NO: 6 resulting in 68% accuracy, 65% specificity, 82% sensitivity).

It is further preferred that the kit for diagnosing Parkinson's disease allows for determining the expression profile at least two platelet-derived miRNAs representative for Parkinson's disease in a blood cell preparation derived from a whole blood sample selected from the group consisting of SEQ ID NO:1-2, SEQ ID NO: 4-19, SEQ ID NO: 21, SEQ ID NO: 23-45, SEQ ID NO: 47-49 or SEQ ID NO: 51. It is further preferred that the kit for diagnosing Parkinson's disease allows for determining the expression profile of a set of platelet-derived miRNAs comprising at least one of the sets of platelet-derived miRNAs selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179 in a blood cell preparation derived from a whole blood sample. It is more preferred that the kit for diagnosing Parkinson's disease allows for determining the expression profile of a set of platelet-derived miRNAs comprising at least one of the sets of platelet-derived miRNAs with high diagnostic discrimination power for diagnosing PD listed in FIG. 2, such as SHP-2 (comprising SEQ ID NO: 1, SEQ ID NO: 2 resulting in 86% accuracy, 86% specificity, 86% sensitivity), SHP-5 (comprising SEQ ID NO: 19, SEQ ID NO: 2 resulting in 85% accuracy, 86% specificity, 83% sensitivity), SHP-6 (comprising SEQ ID NO: 19, SEQ ID NO: 6 resulting in 82% accuracy, 82% specificity, 84% sensitivity), SHP-7 (comprising SEQ ID NO: 18, SEQ ID NO: 4 resulting in 73% accuracy, 69% specificity, 93% sensitivity), SHP-8 (comprising SEQ ID NO: 47, SEQ ID NO: 1 resulting in 73% accuracy, 69% specificity, 92% sensitivity), SHP-10 (comprising SEQ ID NO: 17, SEQ ID NO: 19 resulting in 80% accuracy, 80% specificity, 80% sensitivity), SHP-13 (comprising SEQ ID NO: 2, SEQ ID NO: 4 resulting in 82% accuracy, 83% specificity, 75% sensitivity), SHP-14 (comprising SEQ ID NO: 16, SEQ ID NO: 19 resulting in 76% accuracy, 75% specificity, 83% sensitivity), SHP-16 (comprising SEQ ID NO: 2, SEQ ID NO: 9 resulting in 88% accuracy, 93% specificity, 64% sensitivity), SHP-17 (comprising SEQ ID NO: 19, SEQ ID NO: 21 resulting in 73% accuracy, 71% specificity, 84% sensitivity), SHP-18 (comprising SEQ ID NO: 17, SEQ ID NO: 31 resulting in 75% accuracy, 74% specificity, 80% sensitivity), SHP-19 (comprising SEQ ID NO: 18, SEQ ID NO: 19 resulting in 77% accuracy, 77% specificity, 77% sensitivity), SHP-20 (comprising SEQ ID NO: 47, SEQ ID NO: 16 resulting in 72% accuracy, 70% specificity, 83% sensitivity), SHP-21 (comprising SEQ ID NO: 4, SEQ ID NO: 43 resulting in 70% accuracy, 67% specificity, 85% sensitivity), SHP-26 (comprising SEQ ID NO: 2, SEQ ID NO: 6 resulting in 84% accuracy, 89% specificity, 62% sensitivity), SHP-27 (comprising SEQ ID NO: 15, SEQ ID NO: 18 resulting in 77% accuracy, 77% specificity, 72% sensitivity), SHP-29 (comprising SEQ ID NO: 33, SEQ ID NO: 17 resulting in 67% accuracy, 63% specificity, 86% sensitivity), SHP-32 (comprising SEQ ID NO: 31, SEQ ID NO: 4 resulting in 74% accuracy, 75% specificity, 72% sensitivity), SHP-33 (comprising SEQ ID NO: 2, SEQ ID NO: 5 resulting in 79% accuracy, 82% specificity, 65% sensitivity), SHP-35 (comprising SEQ ID NO: 5, SEQ ID NO: 6 resulting in 75% accuracy, 76% specificity, 70% sensitivity), SHP-36 (comprising SEQ ID NO: 45, SEQ ID NO: 12 resulting in 62% accuracy, 57% specificity, 88% sensitivity), SHP-38 (comprising SEQ ID NO: 4, SEQ ID NO: 6 resulting in 79% accuracy, 82% specificity, 62% sensitivity), SHP-39 (comprising SEQ ID NO: 18, SEQ ID NO: 25 resulting in 69% accuracy, 68% specificity, 74% sensitivity), SHP-40 (comprising SEQ ID NO: 6, SEQ ID NO: 8 resulting in 74% accuracy, 76% specificity, 67% sensitivity), SHP-42 (comprising SEQ ID NO: 6, SEQ ID NO: 7 resulting in 73% accuracy, 73% specificity, 69% sensitivity), SHP-43 (comprising SEQ ID NO: 9, SEQ ID NO: 18 resulting in 66% accuracy, 64% specificity, 76% sensitivity), SHP-44 (comprising SEQ ID NO: 5, SEQ ID NO: 23 resulting in 74% accuracy, 76% specificity, 64% sensitivity), SHP-45 (comprising SEQ ID NO: 16, SEQ ID NO: 18 resulting in 67% accuracy, 65% specificity, 75% sensitivity) or SHP-49 (comprising SEQ ID NO: 18, SEQ ID NO: 21 resulting in 74% accuracy, 76% specificity, 63% sensitivity) in a blood cell preparation derived from a whole blood sample.

It is particularly preferred that the kit for diagnosing Parkinson's disease allows for determining the expression profile of a set of miRNAs in a platelet preparation derived from a whole blood sample. It is more preferred that said platelet preparation is a platelet-rich-plasma preparation. Thus, it is further preferred that the kit for diagnosing Parkinson's disease allows for determining the expression profile at least two platelet-derived miRNAs representative for Parkinson's disease in a platelet preparation derived from a whole blood sample selected from the group consisting of SEQ ID NO:1-2, SEQ ID NO: 4-19, SEQ ID NO: 21, SEQ ID NO: 23-45, SEQ ID NO: 47-49 or SEQ ID NO: 51. It is further preferred that the kit for diagnosing Parkinson's disease allows for determining the expression profile of a set of platelet-derived miRNAs comprising at least one of the sets of platelet-derived miRNAs selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP- 125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179 in a platelet preparation derived from a whole blood sample. It is more preferred that the kit for diagnosing Parkinson's disease allows for determining the expression profile of a set of platelet-derived miRNAs comprising at least one of the sets of platelet-derived miRNAs with high diagnostic discrimination power for diagnosing PD listed in FIG. 2, such as SHP-2 (comprising SEQ ID NO: 1, SEQ ID NO: 2 resulting in 86% accuracy, 86% specificity, 86% sensitivity), SHP-5 (comprising SEQ ID NO: 19, SEQ ID NO: 2 resulting in 85% accuracy, 86% specificity, 83% sensitivity), SHP-6 (comprising SEQ ID NO: 19, SEQ ID NO: 6 resulting in 82% accuracy, 82% specificity, 84% sensitivity), SHP-7 (comprising SEQ ID NO: 18, SEQ ID NO: 4 resulting in 73% accuracy, 69% specificity, 93% sensitivity), SHP-8 (comprising SEQ ID NO: 47, SEQ ID NO: 1 resulting in 73% accuracy, 69% specificity, 92% sensitivity), SHP-10 (comprising SEQ ID NO: 17, SEQ ID NO: 19 resulting in 80% accuracy, 80% specificity, 80% sensitivity), SHP-13 (comprising SEQ ID NO: 2, SEQ ID NO: 4 resulting in 82% accuracy, 83% specificity, 75% sensitivity), SHP-14 (comprising SEQ ID NO: 16, SEQ ID NO: 19 resulting in 76% accuracy, 75% specificity, 83% sensitivity), SHP-16 (comprising SEQ ID NO: 2, SEQ ID NO: 9 resulting in 88% accuracy, 93% specificity, 64% sensitivity), SHP-17 (comprising SEQ ID NO: 19, SEQ ID NO: 21 resulting in 73% accuracy, 71% specificity, 84% sensitivity), SHP-18 (comprising SEQ ID NO: 17, SEQ ID NO: 31 resulting in 75% accuracy, 74% specificity, 80% sensitivity), SHP-19 (comprising SEQ ID NO: 18, SEQ ID NO: 19 resulting in 77% accuracy, 77% specificity, 77% sensitivity), SHP-20 (comprising SEQ ID NO: 47, SEQ ID NO: 16 resulting in 72% accuracy, 70% specificity, 83% sensitivity), SHP-21 (comprising SEQ ID NO: 4, SEQ ID NO: 43 resulting in 70% accuracy, 67% specificity, 85% sensitivity), SHP-26 (comprising SEQ ID NO: 2, SEQ ID NO: 6 resulting in 84% accuracy, 89% specificity, 62% sensitivity), SHP-27 (comprising SEQ ID NO: 15, SEQ ID NO: 18 resulting in 77% accuracy, 77% specificity, 72% sensitivity), SHP-29 (comprising SEQ ID NO: 33, SEQ ID NO: 17 resulting in 67% accuracy, 63% specificity, 86% sensitivity), SHP-32 (comprising SEQ ID NO: 31, SEQ ID NO: 4 resulting in 74% accuracy, 75% specificity, 72% sensitivity), SHP-33 (comprising SEQ ID NO: 2, SEQ ID NO: 5 resulting in 79% accuracy, 82% specificity, 65% sensitivity), SHP-35 (comprising SEQ ID NO: 5, SEQ ID NO: 6 resulting in 75% accuracy, 76% specificity, 70% sensitivity), SHP-36 (comprising SEQ ID NO: 45, SEQ ID NO: 12 resulting in 62% accuracy, 57% specificity, 88% sensitivity), SHP-38 (comprising SEQ ID NO: 4, SEQ ID NO: 6 resulting in 79% accuracy, 82% specificity, 62% sensitivity), SHP-39 (comprising SEQ ID NO: 18, SEQ ID NO: 25 resulting in 69% accuracy, 68% specificity, 74% sensitivity), SHP-40 (comprising SEQ ID NO: 6, SEQ ID NO: 8 resulting in 74% accuracy, 76% specificity, 67% sensitivity), SHP-42 (comprising SEQ ID NO: 6, SEQ ID NO: 7 resulting in 73% accuracy, 73% specificity, 69% sensitivity), SHP-43 (comprising SEQ ID NO: 9, SEQ ID NO: 18 resulting in 66% accuracy, 64% specificity, 76% sensitivity), SHP-44 (comprising SEQ ID NO: 5, SEQ ID NO: 23 resulting in 74% accuracy, 76% specificity, 64% sensitivity), SHP-45 (comprising SEQ ID NO: 16, SEQ ID NO: 18 resulting in 67% accuracy, 65% specificity, 75% sensitivity) or SHP-49 (comprising SEQ ID NO: 18, SEQ ID NO: 21 resulting in 74% accuracy, 76% specificity, 63% sensitivity) in a platelet preparation derived from a whole blood sample.

In a sixth aspect, the invention relates to a set comprising at least two miRNAs isolated from a blood cell preparation derived from a whole blood sample from a subject for diagnosing Parkinson's disease, wherein the miRNAs are selected from the group consisting of SEQ ID NO: 1 to 51.

It is understood that the set of miRNAs isolated of the sixth aspect of the invention includes and/or comprises the aspects detailed in the method according to the first aspect, the aspects detailed in the set comprising polynucleotides according to the second aspect and the aspects detailed in kit according to the aspects of the fifth aspect of the present invention.

It is preferred, that the set comprising at least two miRNAs is isolated from a blood cell preparation derived from the whole blood sample that comprises red blood cells, white blood cells or platelets, it is more preferred that the set of miRNAs is isolated from a blood cell preparation derived from the whole blood sample comprising red blood cells, white blood cells and platelets.

It is further preferred that the set comprising at least two miRNAs isolated for diagnosing Parkinson's disease comprises at least one of the sets of miRNAs listed in FIG. 2.

It is further preferred, that said set of miRNAs isolated comprises platelet-derived miRNAs and wherein said platelet-derived miRNAs are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

It is further preferred that the set comprising at least two miRNAs is isolated from a platelet preparation derived from the whole blood sample.

It is preferred that the set comprising at least two miRNAs is isolated from the blood cell preparation by nucleic acid hybridisation, nucleic acid amplification, polymerase extension, sequencing, flow cytometry, mass spectroscopy or any combination thereof.

It is preferred that the set comprising at least two miRNAs comprises a set of polynucleotides according to the second aspect of the present invention for isolation of said miRNAs from the blood cell preparation.

In a seventh aspect, the invention relates to the use of a set of miRNAs according the sixth aspect of the present invention for diagnosing Parkinson's disease in a subject.

In summary, the present invention is composed of the following items:

1. A method for diagnosing Parkinson's disease comprising the steps of:
   (i) determining an expression profile of a set comprising at least two miRNAs representative for Parkinson's disease in a blood cell preparation derived from a whole blood sample from a subject, and
   (ii) comparing said expression profile to a reference, wherein the comparison of said expression profile to said reference allows for the diagnosis of Parkinson's disease,
   (iii) optionally identifying a subject afflicted with Parkinson's disease for therapeutic intervention,
   wherein the nucleotide sequences of the miRNAs comprised in the set are selected from the group consisting of SEQ ID NO: 1 to 51.

2. The method of item 1, wherein the blood cell preparation derived from the whole blood sample comprises platelets, red blood cells and white blood cells 3. The method according to any of the items 1 to 2, wherein the set of miRNAs comprises at least one of the sets of miRNAs listed in FIG. 2.

4. The method according to any of the items 1 to 3, wherein the set comprises at least two platelet-derived miRNAs representative for Parkinson's disease in a blood cell preparation derived from a whole blood sample and wherein said platelet-derived miRNAs are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

5. The method according to any of the items 1 to 4, wherein the set of miRNAs comprises at least one of the sets of miRNAs selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179 listed in FIG. 2

6. The method according to any of the items 1 to 5, wherein the blood cell preparation derived from the whole blood sample is a platelet preparation, preferably a platelet-rich-plasma preparation.

7. The method according to any of the items 1 to 6, wherein the reference is derived from expression profiles of a set comprising said at least two miRNAs determined from at least two reference subjects.

8. The method according to any of the items 1 to 7, wherein the determining of the expression profile includes reverse-transcription of the nucleotide sequence of the at least two miRNAs comprised in the set into cDNA.

9. A set comprising polynucleotides for detecting a set comprising at least two miRNAs for diagnosing Parkinson's disease in a blood cell preparation derived from a whole blood sample from a subject, wherein the nucleotide sequences of the miRNAs comprised in the set are selected from the group consisting of SEQ ID NO: 1 to 51.

10. The set comprising polynucleotides of item 9, wherein the blood cell preparation derived from the whole blood sample comprises platelets, red blood cells and white blood cells.

11. The set comprising polynucleotides according to any of the items 9 to 10, wherein the set of miRNAs comprises at least one of the sets of miRNAs listed in FIG. 2.

12. The set comprising polynucleotides according to any of the items 9 to 10, wherein the miRNAs comprised in the set are platelet-derived miRNAs and wherein said platelet-derived miRNAs are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

13. The set comprising polynucleotides according to any of the items 9 to 12, wherein the set of miRNAs comprises at least one of the sets of miRNAs selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179

14. The set comprising polynucleotides according to any of the items 9 to 13, wherein the blood cell preparation derived from the whole blood sample is a platelet preparation, preferably a platelet-rich-plasma preparation.

15. The set comprising polynucleotides according to any of the items 9 to 14, wherein
   (i) the polynucleotides comprised in the set are complementary to the miRNAs comprised in the set according to any of the items 9 to 14, or
   (ii) the polynucleotides comprised in the set are fragments of the polynucleotides comprised in the set according to (i), or
   (iii) the polynucleotides comprised in the set are DNA complements according to (i) or DNA fragments according to (ii), or
   (iv) the polynucleotides comprised in the set have at least 80% sequence identity to the polynucleotide sequences of the complementary polynucleotides comprised in the set according to (i) or of the polynucleotide fragments comprised in the set according to (ii) or of the DNA complement or DNA fragments according to (iii).

16. Use of set of polynucleotides according to any of the items 9 to 15 for diagnosing Parkinson's disease in a subject.

17. Means for diagnosing Parkinson's disease in a blood cell preparation derived from a whole blood sample of a subject comprising:

(i) a set of at least two polynucleotides according to any of the items 9 to 15 for determining an expression profile of a set comprising at least two miRNAs representative for Parkinson's disease, and/or
(ii) a biochip, a RT-PCT system, a PCR-system, a flow cytometer, a bead-based multiplex system or a next generation sequencing system for determining an expression profile of a set comprising at least two miRNAs representative for Parkinson's disease
wherein the nucleotide sequences of the miRNAs comprised in the set are selected from the group consisting of SEQ ID NO: 1 to 51.

18. The means of item 17, wherein the set of miRNAs comprises at least one of the sets of miRNAs listed in FIG. 2.

19. A kit for diagnosing Parkinson's disease comprising
(i) means for determining an expression profile of a set comprising at least two miRNAs representative for Parkinson's disease in a blood cell preparation derived from a whole blood sample of a subject, wherein the nucleotide sequences of the miRNAs comprised in the set are selected from the group consisting of SEQ ID NO: 1 to 51, and
(ii) at least one reference, and
(iii) a data carrier
(iv) optionally a whole blood collection tube
(v) optionally means for deriving a blood cell preparation from a whole blood sample 20. The kit of item 19, wherein the data carrier comprises a guide for use of the kit in diagnosing of Parkinson's disease.

21. The kit according to item 20, wherein the data carrier further comprises tools for analysis and evaluation of the determined expression profiles.

22. The kit according to any of the items 19 to 20, wherein the means for determining an expression profile comprise means according to item 17.

23. The kit according to any of the items 19 to 22, wherein the blood cell preparation derived from the whole blood sample comprises platelets, red blood cells and white blood cells 24. The kit according to any of the items 19 to 23, wherein the set of miRNAs comprises at least one of the sets of miRNAs listed in FIG. 2.

25. The kit according to any of the items 19 to 24, wherein the miRNAs comprised in the set are platelet-derived miRNAs and wherein said platelet-derived miRNAs are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

26. The kit according to any of the items 19 to 25, wherein the set of miRNAs comprises at least one of the sets of miRNAs selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179

27. The kit according to any of the items 19 to 26, wherein the blood cell preparation derived from the whole blood sample is a platelet preparation, preferably a platelet-rich-plasma preparation.

28. A set comprising at least two miRNAs isolated from a blood cell preparation derived from a whole blood sample from a subject for diagnosing Parkinson's disease, wherein the miRNAs are selected from the group consisting of SEQ ID NO: 1 to 51.

29. The set of miRNAs of item 28, wherein the blood cell preparation derived from the whole blood sample comprises platelets, red blood cells and white blood cells.

30. The set of miRNAs according to any of the items 28 to 29 wherein the set of miRNAs comprises at least one of the sets of miRNAs listed in FIG. 2.

31. The set of miRNAs according to any of the items 28 to 30, wherein the miRNAs comprised in the set are platelet-derived miRNAs and wherein said platelet-derived miRNAs are selected from the group consisting of SEQ ID NO:1-2, SEQ ID NO: 4-19, SEQ ID NO: 21, SEQ ID NO: 23-45, SEQ ID NO: 47-49 or SEQ ID NO: 51.

32. The set of miRNAs according to any of the items 28 to 31, wherein the set of miRNAs comprises at least one of the sets of miRNAs selected from the group consisting of SHP-2, SHP-5, SHP-6, SHP-7, SHP-8, SHP-10, SHP-13, SHP-14, SHP-16, SHP-17, SHP-18, SHP-19, SHP-20, SHP-21, SHP-26, SHP-27, SHP-29, SHP-32, SHP-33, SHP-35, SHP-36, SHP-38, SHP-39, SHP-40, SHP-42, SHP-43, SHP-44, SHP-45, SHP-49, SHP-50, SHP-51, SHP-52, SHP-53, SHP-54, SHP-55, SHP-56, SHP-57, SHP-58, SHP-59, SHP-60, SHP-61, SHP-62, SHP-63, SHP-64, SHP-65, SHP-66, SHP-67, SHP-69, SHP-70, SHP-71, SHP-72, SHP-73, SHP-74, SHP-75, SHP-76, SHP-77, SHP-78, SHP-79, SHP-80, SHP-82, SHP-83, SHP-84, SHP-85, SHP-86, SHP-87, SHP-89, SHP-90, SHP-91, SHP-92, SHP-93, SHP-94, SHP-95, SHP-96, SHP-97, SHP-98, SHP-99, SHP-100, SHP-102, SHP-104, SHP-105, SHP-106, SHP-107, SHP-109, SHP-110, SHP-111, SHP-112, SHP-113, SHP-114, SHP-115, SHP-116, SHP-117, SHP-118, SHP-119, SHP-120, SHP-121, SHP-122, SHP-123, SHP-124, SHP-125, SHP-126, SHP-127, SHP-128, SHP-129, SHP-130, SHP-131, SHP-132, SHP-133, SHP-134, SHP-135, SHP-136, SHP-137, SHP-138, SHP-139, SHP-140, SHP-141, SHP-142, SHP-143, SHP-144, SHP-145, SHP-146, SHP-147, SHP-148, SHP-149, SHP-150, SHP-151, SHP-152, SHP-153, SHP-155, SHP-156, SHP-157, SHP-158, SHP-159, SHP-160, SHP-161, SHP-162, SHP-163, SHP-164, SHP-165, SHP-166, SHP-167, SHP-168, SHP-169, SHP-170, SHP-171, SHP-172, SHP-173, SHP-174, SHP-175, SHP-176, SHP-177, SHP-178 or SHP-179

33. The set comprising polynucleotides according to any of the items 28 to 32, wherein the blood cell preparation derived from the whole blood sample is a platelet preparation, preferably a platelet-rich-plasma preparation.

34. The set of miRNAs according to any of the items 28 to 33, wherein the set comprising at least two miRNAs is isolated from the blood cell preparation by nucleic acid hybridisation, nucleic acid amplification, polymerase extension, sequencing, flow cytometry, mass spectroscopy or any combination thereof.

35. The set of miRNAs of item 34, comprising a set comprising polynucleotides according to any of the items 9 to 15.

36. Use of a set of miRNAs according to any of the items 28 to 35 for diagnosing Parkinson's disease in a subject.

37. The method according to items 1 to 8, the set comprising polynucleotides according to items 9 to 15, the means according to items 17 to 18, the kit according to items 19 to 27, or the set of miRNAs according to items 28 to 35, wherein the whole blood sample is collected in a whole blood collection tube, preferably it is collected in a PAXgene Blood RNA tube, Tempus Blood RNA tube, EDTA-tube, Na-citrate tube or ACD-tube and optionally contains an additive for stabilizing the RNA-fraction.

38. The method, the set comprising polynucleotides, the means, the kit or the set of miRNAs according to item 37, wherein the blood cell preparation is obtained by separation of the blood cells, preferably by separation of the red blood cell fraction and/or the platelet fraction and/or the white blood cell fraction from the whole blood sample followed by isolation of the (miRNA-comprising) RNA from said blood cell preparation.

39. The method according to any of the items 1 to 8 or according to any of the items 37 to 38, wherein the determining of an expression profile of a set comprising at least two miRNAs representative for PD in step (i) comprises the steps:
    (a) reverse-transcribing the miRNAs comprised in the (total) RNA isolated from the blood cells of the blood cell preparation derived from a whole blood sample into (non-naturally occurring) cDNA
    (b) optionally amplifying the cDNA of step (a)
    (c) quantifying the optionally amplified cDNA, thereby determining the expression profile of said miRNAs 40. The method according to item 39, wherein miRNA-specific or universal reverse transcription DNA-primers are used for reverse transcription in step (a).

41. The method according to any of the items 39 to 40, wherein miRNA-specific forward primer and universal reverse primer or miRNA-specific forward and partially universal reverse primer are used for quantifying the optionally amplified cDNA in step (c).

42. The method according to any of the items 39 to 41, wherein miRNA-specific forward primer and universal reverse primer or miRNA-specific forward and partially universal reverse primer are used for optionally amplifying the cDNA in step (b).

43. The method according to any of the items 39 to 42, wherein that the quantifying in step (c) is performed by real-time PCR, nucleic acid hybridization or sequencing techniques.

44. The method according to any of the items 1 to 8 or according to any of the items 37 to 38, wherein the determining of an expression profile of a set comprising at least two miRNAs representative for PD in step (i) comprises the steps:
    (a) adding a DNA-fragment to the 3'-end of the miRNAs comprised in the (total) RNA isolated from the blood cells of the blood cell preparation derived from a whole blood sample, thereby forming non-naturally occurring RNA-DNA hybrids
    (b) optionally reverse-transcribing said RNA-DNA hybrids to cDNA
    (c) quantifying the optionally reverse-transcribed RNA-DNA hybrids, thereby determining the expression profile of said miRNAs 45. The method according to item 44, wherein DNA-fragments of 1 to 150 nucleotides in length are added to the 3'-end of the miRNAs by ligation or by polymerase-based elongation.

46. The method according to any of the items 44 to 45, wherein universal reverse transcription DNA-primers are used for reverse transcription in step (b).

47. The method according to any of the items 44 to 46, wherein miRNA-specific forward primer and universal reverse primer or miRNA-specific forward and partially universal reverse primer are used for quantifying the optionally amplified cDNA in step (c).

48. The method according to any of the items 44 to 47, wherein that the quantifying in step (c) is performed by real-time PCR, nucleic acid hybridization or sequencing techniques.

49. The method according to any of the items 1 to 8 or 39 to 48, comprising a further step:
    (iv) optionally subjecting said subject identified to be afflicted with Parkinson's disease to therapeutic intervention selected from the group consisting of medication (drug treatment), surgical intervention or lifestyle modification.

BRIEF DESCRIPTION OF THE DRAWINGS

FIG. 1: Overview of the miRNAs determined in blood cell preparations derived from whole blood samples, comprising red blood cells, white blood cells and platelets that are found to be significantly differentially regulated, in subjects suffering from Parkinson's disease when compared to healthy controls and that are suitable for diagnosis of Parkinson's disease. The blood samples from PD-patients and healthy controls were drawn into PAXgene RNA tubes (http://www.preanalytix.com), the total RNA—comprising the miRNA-fraction of blood cells—was isolated by use of the miRNeasy kit (http://www.qiagen.com) and analyzed on dna-microarrays (febit biomed) representing miRBase version 12. Experimental details: SEQ ID NO: Sequence identification number; miRNA: miRNA annotation according to miRBase version 12; Parkinson median g1=median expression level of the PD patients; Healthy Control median g2=median expression level of the healthy controls; log 2FC=log 2 of ratio of Parkinson median g1 and Healthy Control median g2; ttest_rawp=raw p-value calculated according to ttest; ttest_adjp=Benjamini-Hochberg-adjusted p-value calculated according to ttest; AUC=area under the curve statistics; limma_rawp=raw p-value calculated according to limma-test; limma_adjp=Benjamin-Hochberg-adjusted p-value calculated according to limma-test.

FIG. 2: Overview of sets of miRNA-biomarkers (miRNA biomarker signatures SHP-1 to SHP-179) suitable for diagnosing Parkinson's disease in blood cell preparations derived from whole blood samples, comprising red blood cells, white blood cells and platelets. Experimental details: Signature: SEQ ID NO: sequence identification number; miRNA-Identifiers: identifier of the miRNAs according to miRBase version 12; Acc: statistical accuracy in %; Spec:

statistical specificity in %; Sens: statistical sensitivity in %; bal. Acc: statistical balanced accuracy in %.

FIG. 3: Overview of miRNA biomarkers suitable for diagnosing Parkinson's disease in platelet preparations derived from whole blood samples. Experimental details: SEQ ID NO: Sequence identification number; miRNA: miRNA annotation according to miRBase version 12; Expressed in Platelets and/or red blood cells (RBCs). with R=expressed in RBCs, P=expressed in Platelets, PR=expressed in Platelets and RBCs; Parkinson, relative Level Blood cells: relative miRNA expression level in blood cell preparations of whole blood (comprising RBCs, WBCs and platelets) of PD subjects; upon ranking the miRNA expression levels (from least to greatest values) with T=top expressed within range of 25% highest expression levels, L=low expressed within range of 25% lowest expression levels; H=high expressed within range of 50-75% of expression levels, M=medium expressed within range 25-50% expression levels. Healthy Control, relative Level Blood cells: relative miRNA expression level in blood cell preparations of whole blood (comprising RBCs, WBCs and platelets) of Healthy Control subjects. Healthy Control, relative Level Platelets: relative Level Blood cells: relative miRNA expression level in platelet preparations (PRP) of whole blood of Healthy Control subjects. Healthy Control, relative Level Red Blood cells: relative miRNA expression level in red blood cell preparations of whole blood of Healthy Control subjects.

FIG. 4: miRNA-specific DNA-primers (column B) used for reverse transcription (RT) of miRNAs with SEQ ID NO: 1 to 51 to non-naturally occurring cDNA; miRNA-specific forward and universal reverse primers (column C, D) for quantification and optionally amplification of miRNAs with SEQ ID NO: 1 to 51 employed for determining of an expression profile of a set comprising at least two miRNAs representative for PD in a blood cell preparation derived from a whole blood sample; dual-labeled hydrolysis probes (Taqman-probes, column E) utilized for quantifying of miRNAs with SEQ ID NO: 1 to 51 by real-time PCR.

FIG. 5: miRNA-specific forward primer (column B) and partially universal reverse primer (column C) for quantification and optionally amplification of cDNA-transcripts of miRNAs with SEQ ID NO: 1 to 51 employed for determining of an expression profile of a set comprising at least two miRNAs representative for PD in a blood cell preparation derived from a whole blood sample.

FIG. 6: DNA-fragments added to the 3'-end of the miRNAs with SEQ ID NO: 1 to 51 employed for determining of an expression profile of a set comprising at least two miRNAs representative for PD in a blood cell preparation derived from a whole blood sample, thereby forming non-naturally occurring RNA-DNA hybrids.

FIG. 7: Adapters, RT-primers and PCR-primers utilized for next generation sequencing (Illumina small RNA-seq) of the miRNAs with SEQ ID NO: 1 to 51 employed for determining of an expression profile of a set comprising at least two miRNAs representative for PD in a blood cell preparation derived from a whole blood sample: universal 3' RNA Adapters (column A) ligated to the 3'-end of the miRNAs with SEQ ID NO: 1 to 51; universal 5' RNA Adapter (column B) ligated to the 5'-end of the miRNAs with SEQ ID NO: 1 to 51; universal reverse transcription (RT)-Primers (column C) for reverse-transcribing the 3'- and 5'-adapter ligated miRNAs into (non-naturally occurring) cDNA; Small RNA PCR Primer 1=universal forward (column D) and Small RNA PCR Primer 2=universal reverse (PCR) primers (column E) for amplifying the 3'- and 5'-adapter ligated and reverse-transcribed cDNAs of miRNAs with SEQ ID NO: 1 to 51.

EXAMPLES

The Examples are designed in order to further illustrate the present invention and serve a better understanding. They are not to be construed as limiting the scope of the invention in any way.

Example 1: Preparation of Blood Cell Preparations Derived from Whole Blood Samples Blood of Parkinson's Disease patients and healthy controls was drawn in PAXgene Blood RNA tubes (PreAnalytiX GmbH, Hombrechtikon, Switzerland). For each blood donor, 2×2.5 ml of peripheral whole blood was collected. The blood cells preparations were obtained from processing the whole blood samples collected in PAXgene Blood RNA tubes according to the manufacturers protocol. Herein, the blood cell pellet (the cellular blood fraction comprising red blood cells, white blood cells and platelets) was collected by centrifugation for further processing, while the supernatant (including the extra-cellular blood fraction) was discarded. Total RNA, including the small RNA (miRNA-fraction) was extracted from the pelleted blood cells using the miRNeasy Mini Kit (Qiagen GmbH, Hilden, Germany) and the resulting RNA was stored at −70° C. before use in expression profiling experiments.

Example 2: Microarray-Based Determination of Expression Profiles

The RNA-samples were analyzed employing microarray hybridization on the Geniom Realtime Analyzer (febit biomed GmbH, Heidelberg, Germany) using the Geniom Biochip miRNA *Homo sapiens*. Each microfluidic microarray contains complementary dna-probes of 866 miRNAs and miRNA* (each represented by 7 replicates) as annotated in the Sanger miRBase 12.0. Sample labeling with biotine has been carried out by enzymatic on-chip labeling of miRNAs employing febit's MPEA-assay. Following hybridization for 16 hours at 42° C. the biochip was washed automatically and a program for signal enhancement was processed with the Geniom Realtime Analyzer. The resulting detection pictures were evaluated using the Geniom Wizard Software. For each array, the median signal intensity was extracted from the raw data file such that for each miRNA seven intensity values have been calculated corresponding to each replicate copy of miRBase on the array. Following background correction, the seven replicate intensity values of each miRNA were summarized by their median value. To normalize the data across different arrays, quantile normalization was applied and all further analyses were carried out using the normalized and background subtracted intensity values (=Parkinson median g1, Healthy Control median g2). From Parkinson median g1 (=Parkinson's Disease subjects) and Healthy Control median g2 (=Healthy Control subjects) the Fold Change of the expression (=qmedian) was calculated as the ratio g1/g2. The log median represents the log 2-value of the qmedian, which allows more easily to judge on the up/down-regulation due to the positive or negative value.

Example 3: Statistical Analysis

After having verified the normal distribution of the measured data, a parametric t-test (unpaired, two-tailed) was carried out for each miRNA separately, to detect miRNAs that show a different behavior in different groups of blood donors. The resulting p-values (=ttest_rawp) were adjusted for multiple testing by Benjamini-Hochberg adjustment (=ttest_adj). Furthermore, we applied the limma-test for each miRNA separately (=limma_raw) and corrected according to Benjamini-Hochberg (=limma_adj). Additionally, we applied receiver operating characteristics and calculated the "Area under the Curve"-value (=AUC). The ttest-, limma-test- and AUC-values allow to judge on the statistical significance for each miRNA to be differential expressed between group 1 (g1=Parkinson's Disease subjects) and group 2 (=g2=Healthy Control subjects).

Example 4: Classification Performance of Predetermined Sets of miRNAs

In addition to the single biomarker analysis and network analysis, classification of samples using miRNA patterns was carried out using Support Vector Machines (SVM,) as implemented in the Rel071 package. In detail, different kernel (linear, polynomial, sigmoid, radial basis function) Support Vector Machines were evaluated, where the cost parameter was sampled from 0.01 to 10 in decimal powers. The measured miRNA profiles were classified using 100 repetitions of standard 10-fold cross-validation. As a subset selection technique we applied a filter approach based on selecting the miRNAs with SEQ ID NO: 1-51 and 179 subsets comprising of 2 miRNAs thereof. The respective subset was used to train the SVM and to carry out the prediction of the test samples. As result, the mean accuracy (=Acc), specificity (=Spec), and sensitivity (=Sens) were calculated for each subset size. To check for overtraining permutation tests were applied. Here the class labels were sampled randomly and classifications were carried out using the permuted class labels. All statistical analyzes were performed using R. FIG. 3 list the classification performance (accuracy, specificity, sensitivity, balance accuracy) of pre-defined sets of 2 miRNAs each. This translates to the accuracy, specificity, sensitivity and balanced accuracy that is obtained when the classifier comprising the sets of 2 miRNAs is applied to classification between the investigated 2 groups of healthy controls and Parkinson's Disease subjects.

Example 5: Preparation of Platelet Preparations Derived from Whole Blood Samples Blood Draw For platelet-preparations derived from whole blood, venous blood is conveniently drawn into EDTA-tubes (10 ml, Vaccutainer, BD Heidelberg, Germany), Na-citrate tubes (380%; 4.5 ml Vaccutainer, BD Heidelberg, Germany) or ACD-tubes (ACD type A, 8.5 ml, ACD type B, 6.5 ml Vaccutainer, BD Heidelberg, Germany).

Preparation of Platelet-Rich-Plasma (PRP)

Freshly collected whole blood is centrifuged with soft spin (170 g, 15 min) to make Platelet-Rich-Plasma (PRP), buffy coat (white blood cells) and red blood cells, from which the PRP is separated.

Leukocyte-depleted PRP is obtained by either filtering the PRP through leukocyte depletion filters (Pall corporation, Port Washington, N.Y., ISA) or by negative selection employing magnetic cell sorting using human CD45+ magnetic beads (Miltenyi Biotech, Bergisch Gladbach, Germany).

Platelet-concentrate is obtained from PRP by a second hard spin centrifugation (5000 g, 3 min), where platelets are pelleted out of the plasma to yield platelet-concentrate and platelet-poor-plasma (PPP).

Preparation of Platelet-Concentrate from Buffy Coat

The collected whole blood is centrifuged with hard spin (5000 g, 7 min) to make Platelet-Poor-Plasma (PPP), buffy coat (including white blood cells & platelets) and red blood cells, from which the buffy coat comprising the platelets is separated. To concentrate the platelets, the buffy coat is further centrifuged (2000 g, 3 min).

Leukocyte-depleted platelet concentrate is obtained by either filtering through leukocyte depletion filters (Pall corporation, Port Washington, N.Y., ISA) or by negative selection employing magnetic cell sorting using human CD45+ magnetic beads (Miltenyi Biotech, Bergisch Gladbach, Germany).

The invention claimed is:

1. A method for diagnosing Parkinson's disease comprising the steps of:
   (i) isolating total intracellular RNA from platelets, red blood cells and white blood cells obtained from a whole blood sample taken from a subject,
   (ii) determining in said total intracellular RNA an expression profile of a set comprising at least two miRNAs, wherein the at least two miRNAs have a nucleotide sequence according to SEQ ID NO:2 (hsa-miR-1228) and a nucleotide sequence according to SEQ ID NO:4 (hsa-miR-24), (iii) comparing the expression profile determined in said total intracellular RNA to a reference expression profile of at least two healthy control subjects, and
(iv) detecting a down-regulation of the miRNA having a nucleotide sequence according to SEQ ID NO:2 in said total intracellular RNA compared to the reference expression profile and an up-regulation of the miRNA having a nucleotide sequence according to SEQ ID NO:4 in said total intracellular RNA compared to the reference expression profile, thereby diagnosing Parkinson's disease in said subject,
wherein the method comprises a further step of:
(v) subjecting said subject identified to be afflicted with Parkinson's disease to medical or surgical intervention directed to Parkinson's disease.

2. The method of claim 1, wherein the determining of the expression profile includes reverse-transcription of the nucleotide sequence of the at least two miRNAs comprised in the set into cDNA.

3. The method according to claim 1, wherein the whole blood sample is collected in a whole blood collection tube, preferably it is collected in a PAXgene Blood RNA tube, Tempus Blood RNA tube, EDTA-tube, Na-citrate tube or ACD-tube and optionally contains an additive for stabilizing the RNA-fraction.

4. The method according to claim 1, wherein the red blood cells, platelets and white blood cells are obtained from the whole blood sample taken from the subject by centrifuging the whole blood sample and removing the supernatant.

5. The method of claim 1, wherein the determining of an expression profile of a set comprising at least two miRNAs in said total intracellular RNA in step (ii) comprises the steps of:
(a) reverse-transcribing the at least two miRNAs comprised in said total intracellular RNA into non-naturally occurring cDNA;
(b) amplifying the cDNA of step (a); and
(c) quantifying the amplified cDNA, thereby determining the expression profile of said at least two miRNAs.

6. The method of claim 1, wherein the determining of an expression profile of a set comprising at least two miRNAs in said total intracellular RNA in step (ii) comprises the steps of:
(a) adding a DNA-fragment to the 3'-end of the at least two miRNAs comprised in said total intracellular RNA, thereby forming non-naturally occurring RNA-DNA hybrids;
(b) reverse-transcribing said RNA-DNA hybrids to cDNA; and
(c) quantifying the reverse-transcribed RNA-DNA hybrids, thereby determining the expression profile of said at least two miRNAs.

7. The method of claim 1, wherein the medical or surgical intervention directed to Parkinson's disease is selected from the group consisting of medication, surgical intervention or lifestyle modification.

8. A method for diagnosing Parkinson's disease comprising the steps of:
(i) determining an expression profile of a set comprising at least two miRNAs representative for Parkinson's disease in a blood cell preparation derived from a whole blood sample from a subject, wherein the at least two miRNAs have a nucleotide sequence according to SEQ ID NO:2 (hsa-miR-1228) and a nucleotide sequence according to SEQ ID NO: 4 (hsa-miR-24),
(ii) comparing the expression profile determined in the blood cell preparation derived from a whole blood sample from the subject to a reference expression profile of at least two healthy control subjects, and
(iii) detecting a down-regulation of the miRNA having a nucleotide sequence according to SEQ ID NO:2 in the blood cell preparation derived from a whole blood sample from the subject compared to the reference expression profile and an up-regulation of the miRNA having a nucleotide sequence according to SEQ ID NO:4 in the blood cell preparation derived from a whole blood sample from the subject compared to the reference expression profile, and thereby diagnosing Parkinson's disease in said subject,
wherein the method comprises a further step of:
(iv) subjecting said subject identified to be afflicted with Parkinson's disease to medical or surgical intervention directed to Parkinson's disease.

9. A method for diagnosing Parkinson's disease comprising the steps of:
(i) isolating total intracellular RNA from platelets, red blood cells and white blood cells obtained from a whole blood sample taken from a subject,
(ii) determining in said total intracellular RNA an expression profile of a set comprising at least two miRNAs, wherein the at least two miRNAs have a nucleotide sequence according to SEQ ID NO:2 (hsa-miR-1228) and a nucleotide sequence according to SEQ ID NO:4 (hsa-miR-24),
(iii) comparing the expression profile determined in said total intracellular RNA to a reference expression profile of at least two healthy control subjects, and
(iv) detecting a down-regulation of the miRNA having a nucleotide sequence according to SEQ ID NO:2 in said total intracellular RNA compared to the reference expression profile and an up-regulation of the miRNA having a nucleotide sequence according to SEQ ID NO:4 in said total intracellular RNA compared to the reference expression profile, and thereby diagnosing Parkinson's disease in said subject,
wherein the determining of an expression profile of a set comprising at least two miRNAs in said total intracellular RNA in step (ii) comprises the steps of:
(a) adding a DNA-fragment to the 3'-end of the at least two miRNAs comprised in said total intracellular RNA, thereby forming non-naturally occurring RNA-DNA hybrids;
(b) reverse-transcribing said RNA-DNA hybrids to cDNA; and
(c) quantifying the reverse-transcribed RNA-DNA hybrids, thereby determining the expression profile of said at least two miRNAs,
wherein the method comprises a further step of:
(v) subjecting said subject identified to be afflicted with Parkinson's disease to medical or surgical intervention directed to Parkinson's disease.

10. The method of claim 1, wherein the medical intervention is administration of a drug for treatment of Parkinson's disease to said subject.

11. The method of claim 1, wherein the medical intervention is administration of one or more of a dopaminergic drug, carbidopa-levodopa, a dopamine agonist, a MAO-B inhibitor, a catechol O-methyltransferase (COMT) inhibitor, an anticholinergic, and Amantadine to said subject.

12. The method of claim 8, wherein the medical intervention is administration of a drug for treatment of Parkinson's disease to said subject.

13. The method of claim 8, wherein the medical intervention is administration of one or more of a dopaminergic drug, carbidopa-levodopa, a dopamine agonist, a MAO-B inhibitor, a catechol O-methyltransferase (COMT) inhibitor, an anticholinergic, and Amantadine to said subject.

14. The method of claim 9, wherein the medical intervention is administration of a drug for treatment of Parkinson's disease to said subject.

15. The method of claim 9, wherein the medical intervention is administration of one or more of a dopaminergic drug, carbidopa-levodopa, a dopamine agonist, a MAO-B inhibitor, a catechol O-methyltransferase (COMT) inhibitor, an anticholinergic, and Amantadine to said subject.

* * * * *

SEQUENCE LISTING

```
<160> NUMBER OF SEQ ID NOS: 227

<210> SEQ ID NO 1
<211> LENGTH: 21
<212> TYPE: RNA
<213> ORGANISM: Homo sapiens

<400> SEQUENCE: 1
aucacauugc cagggauuuc c                                              21

<210> SEQ ID NO 2
<211> LENGTH: 20
<212> TYPE: RNA
<213> ORGANISM: Homo sapiens

<400> SEQUENCE: 2
ucacaccugc cucgcccccc                                                20

<210> SEQ ID NO 3
<211> LENGTH: 22
<212> TYPE: RNA
```

<213> ORGANISM: Homo sapiens

<400> SEQUENCE: 3
ucucccaacc cuuguaccag ug                                              22

<210> SEQ ID NO 4
<211> LENGTH: 22
<212> TYPE: RNA
<213> ORGANISM: Homo sapiens

<400> SEQUENCE: 4
uggcucaguu cagcaggaac ag                                              22

<210> SEQ ID NO 5
<211> LENGTH: 23
<212> TYPE: RNA
<213> ORGANISM: Homo sapiens

<400> SEQUENCE: 5
aaaagugcuu acagugcagg uag                                             23

<210> SEQ ID NO 6
<211> LENGTH: 22
<212> TYPE: RNA
<213> ORGANISM: Homo sapiens

<400> SEQUENCE: 6
uuaucagaau cuccaggggu ac                                              22

<210> SEQ ID NO 7
<211> LENGTH: 23
<212> TYPE: RNA
<213> ORGANISM: Homo sapiens

<400> SEQUENCE: 7
uaaagugcuu auagugcagg uag                                             23

<210> SEQ ID NO 8
<211> LENGTH: 22
<212> TYPE: RNA
<213> ORGANISM: Homo sapiens

<400> SEQUENCE: 8
ucguaccgug aguaauaaug cg                                              22

<210> SEQ ID NO 9
<211> LENGTH: 23
<212> TYPE: RNA
<213> ORGANISM: Homo sapiens

<400> SEQUENCE: 9
ugagugugug ugugugagug ugu                                             23

<210> SEQ ID NO 10
<211> LENGTH: 23
<212> TYPE: RNA
<213> ORGANISM: Homo sapiens

<400> SEQUENCE: 10
uauucauuua uccccagccu aca                                             23

<210> SEQ ID NO 11
<211> LENGTH: 22

```
<212> TYPE: RNA
<213> ORGANISM: Homo sapiens

<400> SEQUENCE: 11
uggagagaaa ggcaguuccu ga                                        22

<210> SEQ ID NO 12
<211> LENGTH: 22
<212> TYPE: RNA
<213> ORGANISM: Homo sapiens

<400> SEQUENCE: 12
aaaccguuac cauuacugag uu                                        22

<210> SEQ ID NO 13
<211> LENGTH: 23
<212> TYPE: RNA
<213> ORGANISM: Homo sapiens

<400> SEQUENCE: 13
caaagugcug uucgugcagg uag                                       23

<210> SEQ ID NO 14
<211> LENGTH: 22
<212> TYPE: RNA
<213> ORGANISM: Homo sapiens

<400> SEQUENCE: 14
uacccauugc auaucggagu ug                                        22

<210> SEQ ID NO 15
<211> LENGTH: 22
<212> TYPE: RNA
<213> ORGANISM: Homo sapiens

<400> SEQUENCE: 15
aaaagcuggg uugagagggc aa                                        22

<210> SEQ ID NO 16
<211> LENGTH: 22
<212> TYPE: RNA
<213> ORGANISM: Homo sapiens

<400> SEQUENCE: 16
uccuguacug agcugccccg ag                                        22

<210> SEQ ID NO 17
<211> LENGTH: 23
<212> TYPE: RNA
<213> ORGANISM: Homo sapiens

<400> SEQUENCE: 17
agcagcauug uacagggcua uga                                       23

<210> SEQ ID NO 18
<211> LENGTH: 23
<212> TYPE: RNA
<213> ORGANISM: Homo sapiens

<400> SEQUENCE: 18
ugaggggcag agagcgagac uuu                                       23

<210> SEQ ID NO 19
```

```
<211> LENGTH: 22
<212> TYPE: RNA
<213> ORGANISM: Homo sapiens

<400> SEQUENCE: 19
ggcuacaaca caggacccgg gc                                              22

<210> SEQ ID NO 20
<211> LENGTH: 22
<212> TYPE: RNA
<213> ORGANISM: Homo sapiens

<400> SEQUENCE: 20
auaaagcuag auaaccgaaa gu                                              22

<210> SEQ ID NO 21
<211> LENGTH: 21
<212> TYPE: RNA
<213> ORGANISM: Homo sapiens

<400> SEQUENCE: 21
cauaaaguag aaagcacuac u                                               21

<210> SEQ ID NO 22
<211> LENGTH: 22
<212> TYPE: RNA
<213> ORGANISM: Homo sapiens

<400> SEQUENCE: 22
ugcaacuuac cugagucauu ga                                              22

<210> SEQ ID NO 23
<211> LENGTH: 23
<212> TYPE: RNA
<213> ORGANISM: Homo sapiens

<400> SEQUENCE: 23
uaaggugcau cuagugcagu uag                                             23

<210> SEQ ID NO 24
<211> LENGTH: 22
<212> TYPE: RNA
<213> ORGANISM: Homo sapiens

<400> SEQUENCE: 24
auauaauaca accugcuaag ug                                              22

<210> SEQ ID NO 25
<211> LENGTH: 21
<212> TYPE: RNA
<213> ORGANISM: Homo sapiens

<400> SEQUENCE: 25
aucacauugc cagggauuac c                                               21

<210> SEQ ID NO 26
<211> LENGTH: 23
<212> TYPE: RNA
<213> ORGANISM: Homo sapiens

<400> SEQUENCE: 26
ugugcaaauc caugcaaaac uga                                             23
```

```
<210> SEQ ID NO 27
<211> LENGTH: 21
<212> TYPE: RNA
<213> ORGANISM: Homo sapiens

<400> SEQUENCE: 27
uggguuuacg uugggagaac u                                            21

<210> SEQ ID NO 28
<211> LENGTH: 23
<212> TYPE: RNA
<213> ORGANISM: Homo sapiens

<400> SEQUENCE: 28
uguaaacauc cuacacucuc agc                                          23

<210> SEQ ID NO 29
<211> LENGTH: 21
<212> TYPE: RNA
<213> ORGANISM: Homo sapiens

<400> SEQUENCE: 29
gugggcgggg gcaggugugu g                                            21

<210> SEQ ID NO 30
<211> LENGTH: 22
<212> TYPE: RNA
<213> ORGANISM: Homo sapiens

<400> SEQUENCE: 30
acugcugagc uagcacuucc cg                                           22

<210> SEQ ID NO 31
<211> LENGTH: 20
<212> TYPE: RNA
<213> ORGANISM: Homo sapiens

<400> SEQUENCE: 31
acugccccag gugcugcugg                                              20

<210> SEQ ID NO 32
<211> LENGTH: 22
<212> TYPE: RNA
<213> ORGANISM: Homo sapiens

<400> SEQUENCE: 32
aauugcacgg uauccaucug ua                                           22

<210> SEQ ID NO 33
<211> LENGTH: 21
<212> TYPE: RNA
<213> ORGANISM: Homo sapiens

<400> SEQUENCE: 33
agggcccccc cucaauccug u                                            21

<210> SEQ ID NO 34
<211> LENGTH: 21
<212> TYPE: RNA
<213> ORGANISM: Homo sapiens

<400> SEQUENCE: 34
uaaagugcug acagugcaga u                                            21
```

```
<210> SEQ ID NO 35
<211> LENGTH: 20
<212> TYPE: RNA
<213> ORGANISM: Homo sapiens

<400> SEQUENCE: 35
uacaguauag augauguacu                                              20

<210> SEQ ID NO 36
<211> LENGTH: 22
<212> TYPE: RNA
<213> ORGANISM: Homo sapiens

<400> SEQUENCE: 36
ugagguagua gguuguaugg uu                                           22

<210> SEQ ID NO 37
<211> LENGTH: 22
<212> TYPE: RNA
<213> ORGANISM: Homo sapiens

<400> SEQUENCE: 37
agagguagua gguugcauag uu                                           22

<210> SEQ ID NO 38
<211> LENGTH: 22
<212> TYPE: RNA
<213> ORGANISM: Homo sapiens

<400> SEQUENCE: 38
aaaagcuggg uugagagggc ga                                           22

<210> SEQ ID NO 39
<211> LENGTH: 21
<212> TYPE: RNA
<213> ORGANISM: Homo sapiens

<400> SEQUENCE: 39
agggagggac ggggggcugug c                                           21

<210> SEQ ID NO 40
<211> LENGTH: 19
<212> TYPE: RNA
<213> ORGANISM: Homo sapiens

<400> SEQUENCE: 40
aaaagcuggg uugagagga                                               19

<210> SEQ ID NO 41
<211> LENGTH: 21
<212> TYPE: RNA
<213> ORGANISM: Homo sapiens

<400> SEQUENCE: 41
agcuacaucu ggcuacuggg u                                            21

<210> SEQ ID NO 42
<211> LENGTH: 22
<212> TYPE: RNA
<213> ORGANISM: Homo sapiens

<400> SEQUENCE: 42
ccaauauuac ugugcugcuu ua                                           22
```

<210> SEQ ID NO 43
<211> LENGTH: 21
<212> TYPE: RNA
<213> ORGANISM: Homo sapiens

<400> SEQUENCE: 43
gcccuccgcc cgugcacccc g                                    21

<210> SEQ ID NO 44
<211> LENGTH: 17
<212> TYPE: RNA
<213> ORGANISM: Homo sapiens

<400> SEQUENCE: 44
ucccaccgcu gccaccc                                         17

<210> SEQ ID NO 45
<211> LENGTH: 21
<212> TYPE: RNA
<213> ORGANISM: Homo sapiens

<400> SEQUENCE: 45
cggcggggac ggcgauuggu c                                    21

<210> SEQ ID NO 46
<211> LENGTH: 21
<212> TYPE: RNA
<213> ORGANISM: Homo sapiens

<400> SEQUENCE: 46
uggacugccc ugaucuggag a                                    21

<210> SEQ ID NO 47
<211> LENGTH: 24
<212> TYPE: RNA
<213> ORGANISM: Homo sapiens

<400> SEQUENCE: 47
ucccugagac ccuuuaaccu guga                                 24

<210> SEQ ID NO 48
<211> LENGTH: 22
<212> TYPE: RNA
<213> ORGANISM: Homo sapiens

<400> SEQUENCE: 48
uuaugguuug ccugggacug ag                                   22

<210> SEQ ID NO 49
<211> LENGTH: 22
<212> TYPE: RNA
<213> ORGANISM: Homo sapiens

<400> SEQUENCE: 49
ugccuacuga gcugaaacac ag                                   22

<210> SEQ ID NO 50
<211> LENGTH: 23
<212> TYPE: RNA
<213> ORGANISM: Homo sapiens

<400> SEQUENCE: 50
cuaauaguau cuaccacaau aaa                                           23

<210> SEQ ID NO 51
<211> LENGTH: 22
<212> TYPE: RNA
<213> ORGANISM: Homo sapiens

<400> SEQUENCE: 51
ucugggcaac aaagugagac cu                                            22

<210> SEQ ID NO 52
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 52
atcacattgc caggg                                                    15

<210> SEQ ID NO 53
<211> LENGTH: 14
<212> TYPE: DNA
<213> ORGANISM: Artificial Sequence
<220> FEATURE:
<223> OTHER INFORMATION: chemically-synthesized polynucleotide

<400> SEQUENCE: 53
tcacacctgc ctcg                                                     14

<210> SEQ ID NO 54
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 54
tctcccaacc cttgta                                                   16

<210> SEQ ID NO 55
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 55
tggctcagtt cagcag                                                   16

<210> SEQ ID NO 56
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 56
aaaagtgctt acagtgc                                                  17

<210> SEQ ID NO 57
<211> LENGTH: 16
<212> TYPE: DNA
<213> ORGANISM: Artificial Sequence
<220> FEATURE:
<223> OTHER INFORMATION: chemically-synthesized polynucleotide

```
<400> SEQUENCE: 57
ttatcagaat ctccag                                                     16

<210> SEQ ID NO 58
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 58
taaagtgctt atagtgc                                                    17

<210> SEQ ID NO 59
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 59
tcgtaccgtg agtaat                                                     16

<210> SEQ ID NO 60
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 60
tgagtgtgtg tgtgtga                                                    17

<210> SEQ ID NO 61
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 61
tattcattta tccccag                                                    17

<210> SEQ ID NO 62
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 62
tggagagaaa ggcagt                                                     16

<210> SEQ ID NO 63
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 63
aaaccgttac cattac                                                     16

<210> SEQ ID NO 64
```

```
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 64
caaagtgctg ttcgtgc                                                    17

<210> SEQ ID NO 65
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 65
tacccattgc atatcg                                                     16

<210> SEQ ID NO 66
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 66
aaaagctggg ttgaga                                                     16

<210> SEQ ID NO 67
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 67
tcctgtactg agctgc                                                     16

<210> SEQ ID NO 68
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 68
agcagcattg tacaggg                                                    17

<210> SEQ ID NO 69
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 69
tgaggggcag agagcga                                                    17

<210> SEQ ID NO 70
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 70
```
ggctacaaca caggac                                                    16

<210> SEQ ID NO 71
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 71
ataaagctag ataacc                                                    16

<210> SEQ ID NO 72
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 72
cataaagtag aaagc                                                     15

<210> SEQ ID NO 73
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 73
tgcaacttac ctgagt                                                    16

<210> SEQ ID NO 74
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 74
taaggtgcat ctagtgc                                                   17

<210> SEQ ID NO 75
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 75
atataataca acctgc                                                    16

<210> SEQ ID NO 76
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 76
atcacattgc caggg                                                     15

<210> SEQ ID NO 77
<211> LENGTH: 17
<212> TYPE: DNA

<213> ORGANISM: Artificial Sequence
<220> FEATURE:
<223> OTHER INFORMATION: chemically-synthesized polynucleotide

<400> SEQUENCE: 77
tgtgcaaatc catgcaa                                                   17

<210> SEQ ID NO 78
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 78
tgggtttacg ttggg                                                     15

<210> SEQ ID NO 79
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 79
tgtaaacatc ctacact                                                   17

<210> SEQ ID NO 80
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 80
gtgggcgggg gcaggt                                                    16

<210> SEQ ID NO 81
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 81
actgctgagc tagcac                                                    16

<210> SEQ ID NO 82
<211> LENGTH: 14
<212> TYPE: DNA
<213> ORGANISM: Artificial Sequence
<220> FEATURE:
<223> OTHER INFORMATION: chemically-synthesized polynucleotide

<400> SEQUENCE: 82
actgccccag gtgc                                                      14

<210> SEQ ID NO 83
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 83
aattgcacgg tatcca                                                    16

<210> SEQ ID NO 84
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 84 agggccccccc ctcaa                                            15

<210> SEQ ID NO 85
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 85
taaagtgctg acagt                                             15

<210> SEQ ID NO 86
<211> LENGTH: 14
<212> TYPE: DNA
<213> ORGANISM: Artificial Sequence
<220> FEATURE:
<223> OTHER INFORMATION: chemically-synthesized polynucleotide

<400> SEQUENCE: 86
tacagtatag atga                                              14

<210> SEQ ID NO 87
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 87
tgaggtagta ggttgt                                            16

<210> SEQ ID NO 88
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 88
agaggtagta ggttgc                                            16

<210> SEQ ID NO 89
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 89
aaaagctggg ttgaga                                            16

<210> SEQ ID NO 90
<211> LENGTH: 16
<212> TYPE: DNA
<213> ORGANISM: Artificial Sequence
<220> FEATURE:

```
<223> OTHER INFORMATION: chemically-synthesized polynucleotide

<400> SEQUENCE: 90
agggagggac gggggc                                                        16

<210> SEQ ID NO 91
<211> LENGTH: 13
<212> TYPE: DNA
<213> ORGANISM: Artificial Sequence
<220> FEATURE:
<223> OTHER INFORMATION: chemically-synthesized polynucleotide

<400> SEQUENCE: 91
aaaagctggg ttg                                                           13

<210> SEQ ID NO 92
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 92
agctacatct ggcta                                                         15

<210> SEQ ID NO 93
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 93
ccaatattac tgtgct                                                        16

<210> SEQ ID NO 94
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 94
gccctccgcc cgtgca                                                        16

<210> SEQ ID NO 95
<211> LENGTH: 11
<212> TYPE: DNA
<213> ORGANISM: Artificial Sequence
<220> FEATURE:
<223> OTHER INFORMATION: chemically-synthesized polynucleotide

<400> SEQUENCE: 95
tcccaccgct g                                                             11

<210> SEQ ID NO 96
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 96
cggcggggac ggcgat                                                        16
```

```
<210> SEQ ID NO 97
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 97
tggactgccc tgatc                                                    15

<210> SEQ ID NO 98
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 98
tccctgagac cctttaac                                                 18

<210> SEQ ID NO 99
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 99
ttatggtttg cctggg                                                   16

<210> SEQ ID NO 100
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 100
tgcctactga gctgaa                                                   16

<210> SEQ ID NO 101
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 101
ctaatagtat ctaccac                                                  17

<210> SEQ ID NO 102
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 102
tctgggcaac aaagtg                                                   16

<210> SEQ ID NO 103
<211> LENGTH: 36
<212> TYPE: DNA
<213> ORGANISM: Artificial Sequence
<220> FEATURE:
<223> OTHER INFORMATION: chemically-synthesized polynucleotide
```

<400> SEQUENCE: 103
ctcaactggt gtcgtggagt cggcaattca gttgag    36

<210> SEQ ID NO 104
<211> LENGTH: 14
<212> TYPE: DNA
<213> ORGANISM: Artificial Sequence
<220> FEATURE:
<223> OTHER INFORMATION: chemically-synthesized polynucleotide

<400> SEQUENCE: 104
acactccagc tggg    14

<210> SEQ ID NO 105
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 105
ctcaactggt gtcgtggagt    20

<210> SEQ ID NO 106
<211> LENGTH: 10
<212> TYPE: DNA
<213> ORGANISM: Artificial Sequence
<220> FEATURE:
<223> OTHER INFORMATION: chemically-synthesized polynucleotide

<400> SEQUENCE: 106
ttcagttgag    10

<210> SEQ ID NO 107
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 107
agatcacatt gccaggga    18

<210> SEQ ID NO 108
<211> LENGTH: 16
<212> TYPE: DNA
<213> ORGANISM: Artificial Sequence
<220> FEATURE:
<223> OTHER INFORMATION: chemically-synthesized polynucleotide

<400> SEQUENCE: 108
gcagtcacac ctgcct    16

<210> SEQ ID NO 109
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 109
gtctcccaac ccttgtac    18

<210> SEQ ID NO 110
<211> LENGTH: 17

```
<212> TYPE: DNA
<213> ORGANISM: Artificial Sequence
<220> FEATURE:
<223> OTHER INFORMATION: chemically-synthesized polynucleotide

<400> SEQUENCE: 110
ggctcagttc agcagga                                                      17

<210> SEQ ID NO 111
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 111
gaaaagtgct tacagtgcag                                                   20

<210> SEQ ID NO 112
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 112
cgcagttatc agaatctcca g                                                 21

<210> SEQ ID NO 113
<211> LENGTH: 22
<212> TYPE: DNA
<213> ORGANISM: Artificial Sequence
<220> FEATURE:
<223> OTHER INFORMATION: chemically-synthesized polynucleotide

<400> SEQUENCE: 113
acagtaaagt gcttatagtg ca                                                22

<210> SEQ ID NO 114
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 114
gcagtcgtac cgtgagtaa                                                    19

<210> SEQ ID NO 115
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 115
tgagtgtgtg tgtgtgagt                                                    19

<210> SEQ ID NO 116
<211> LENGTH: 22
<212> TYPE: DNA
<213> ORGANISM: Artificial Sequence
<220> FEATURE:
<223> OTHER INFORMATION: chemically-synthesized polynucleotide

<400> SEQUENCE: 116
```

```
cgcagtattc atttatcccc ag                                              22
```

<210> SEQ ID NO 117
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 117

```
gtggagagaa aggcagttc                                                  19
```

<210> SEQ ID NO 118
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 118

```
gcagaaaccg ttaccattac t                                               21
```

<210> SEQ ID NO 119
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 119

```
gcaaagtgct gttcgtg                                                    17
```

<210> SEQ ID NO 120
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 120

```
agtacccatt gcatatcgga                                                 20
```

<210> SEQ ID NO 121
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 121

```
cagaaaagct gggttgaga                                                  19
```

<210> SEQ ID NO 122
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 122

```
gcagtcctgt actgagctg                                                  19
```

<210> SEQ ID NO 123
<211> LENGTH: 18
<212> TYPE: DNA
<213> ORGANISM: Artificial Sequence

```
<220> FEATURE:
<223> OTHER INFORMATION: chemically-synthesized polynucleotide

<400> SEQUENCE: 123
agagcagcat tgtacagg                                                 18

<210> SEQ ID NO 124
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 124 tgagggcag agagcga                                                   17

<210> SEQ ID NO 125
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 125
gggctacaac acaggac                                                  17

<210> SEQ ID NO 126
<211> LENGTH: 23
<212> TYPE: DNA
<213> ORGANISM: Artificial Sequence
<220> FEATURE:
<223> OTHER INFORMATION: chemically-synthesized polynucleotide

<400> SEQUENCE: 126
cgcagataaa gctagataac cga                                           23

<210> SEQ ID NO 127
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 127
gcagcataaa gtagaaagca c                                             21

<210> SEQ ID NO 128
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 128
agtgcaactt acctgagtca                                               20

<210> SEQ ID NO 129
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 129
gtaaggtgca tctagtgcag                                               20
```

<210> SEQ ID NO 130
<211> LENGTH: 22
<212> TYPE: DNA
<213> ORGANISM: Artificial Sequence
<220> FEATURE:
<223> OTHER INFORMATION: chemically-synthesized polynucleotide

<400> SEQUENCE: 130
cgcagatata atacaacctg ct                                            22

<210> SEQ ID NO 131
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 131
agatcacatt gccaggga                                                 18

<210> SEQ ID NO 132
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 132
agtgtgcaaa tccatgcaa                                                19

<210> SEQ ID NO 133
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 133
tgggtttacg ttgggaga                                                 18

<210> SEQ ID NO 134
<211> LENGTH: 22
<212> TYPE: DNA
<213> ORGANISM: Artificial Sequence
<220> FEATURE:
<223> OTHER INFORMATION: chemically-synthesized polynucleotide

<400> SEQUENCE: 134
cagtgtaaac atcctacact ct                                            22

<210> SEQ ID NO 135
<211> LENGTH: 13
<212> TYPE: DNA
<213> ORGANISM: Artificial Sequence
<220> FEATURE:
<223> OTHER INFORMATION: chemically-synthesized polynucleotide

<400> SEQUENCE: 135
gcgggggcag gtg                                                      13

<210> SEQ ID NO 136
<211> LENGTH: 17
<212> TYPE: DNA
<213> ORGANISM: Artificial Sequence
<220> FEATURE:
<223> OTHER INFORMATION: chemically-synthesized polynucleotide

```
<400> SEQUENCE: 136
actgctgagc tagcact                                                    17

<210> SEQ ID NO 137
<211> LENGTH: 14
<212> TYPE: DNA
<213> ORGANISM: Artificial Sequence
<220> FEATURE:
<223> OTHER INFORMATION: chemically-synthesized polynucleotide

<400> SEQUENCE: 137
ctgccccagg tgct                                                       14

<210> SEQ ID NO 138
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 138
agaattgcac ggtatccatc                                                 20

<210> SEQ ID NO 139
<211> LENGTH: 15
<212> TYPE: DNA
<213> ORGANISM: Artificial Sequence
<220> FEATURE:
<223> OTHER INFORMATION: chemically-synthesized polynucleotide

<400> SEQUENCE: 139
ggccccccct caatc                                                      15

<210> SEQ ID NO 140
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 140
gcagtaaagt gctgacagtg                                                 20

<210> SEQ ID NO 141
<211> LENGTH: 22
<212> TYPE: DNA
<213> ORGANISM: Artificial Sequence
<220> FEATURE:
<223> OTHER INFORMATION: chemically-synthesized polynucleotide

<400> SEQUENCE: 141
cgcagtacag tatagatgat gt                                              22

<210> SEQ ID NO 142
<211> LENGTH: 23
<212> TYPE: DNA
<213> ORGANISM: Artificial Sequence
<220> FEATURE:
<223> OTHER INFORMATION: chemically-synthesized polynucleotide

<400> SEQUENCE: 142
gcagtgaggt agtaggttgt atg                                             23

<210> SEQ ID NO 143
```

```
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 143
agagaggtag taggttgcat                                                    20

<210> SEQ ID NO 144
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 144
cagaaaagct gggttgaga                                                     19

<210> SEQ ID NO 145
<211> LENGTH: 13
<212> TYPE: DNA
<213> ORGANISM: Artificial Sequence
<220> FEATURE:
<223> OTHER INFORMATION: chemically-synthesized polynucleotide

<400> SEQUENCE: 145
gggacggggg ctg                                                           13

<210> SEQ ID NO 146
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 146
gcagaaaagc tgggttgag                                                     19

<210> SEQ ID NO 147
<211> LENGTH: 20
<212> TYPE: DNA
<213> ORGANISM: Artificial Sequence
<220> FEATURE:
<223> OTHER INFORMATION: chemically-synthesized polynucleotide

<400> SEQUENCE: 147
cagagctaca tctggctact                                                    20

<210> SEQ ID NO 148
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 148
cgcagccaat attactgtg                                                     19

<210> SEQ ID NO 149
<211> LENGTH: 13
<212> TYPE: DNA
<213> ORGANISM: Artificial Sequence
<220> FEATURE:
<223> OTHER INFORMATION: chemically-synthesized polynucleotide

<400> SEQUENCE: 149
```
ccctccgccc gtg                                                          13

<210> SEQ ID NO 150
<211> LENGTH: 13
<212> TYPE: DNA
<213> ORGANISM: Artificial Sequence
<220> FEATURE:
<223> OTHER INFORMATION: chemically-synthesized polynucleotide

<400> SEQUENCE: 150
cccaccgctg cca                                                          13

<210> SEQ ID NO 151
<211> LENGTH: 14
<212> TYPE: DNA
<213> ORGANISM: Artificial Sequence
<220> FEATURE:
<223> OTHER INFORMATION: chemically-synthesized polynucleotide

<400> SEQUENCE: 151
ggggacggcg attg                                                         14

<210> SEQ ID NO 152
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 152
tggactgccc tgatctg                                                      17

<210> SEQ ID NO 153
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 153
ccctgagacc ctttaacct                                                    19

<210> SEQ ID NO 154
<211> LENGTH: 19
<212> TYPE: DNA
<213> ORGANISM: Artificial Sequence
<220> FEATURE:
<223> OTHER INFORMATION: chemically-synthesized polynucleotide

<400> SEQUENCE: 154
agttatggtt tgcctggga                                                    19

<210> SEQ ID NO 155
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 155
cagtgcctac tgagctga                                                     18

<210> SEQ ID NO 156
<211> LENGTH: 22
<212> TYPE: DNA

```
<213> ORGANISM: Artificial Sequence
<220> FEATURE:
<223> OTHER INFORMATION: chemically-synthesized polynucleotide

<400> SEQUENCE: 156
cgcagctaat agtatctacc ac                                              22

<210> SEQ ID NO 157
<211> LENGTH: 18
<212> TYPE: DNA
<213> ORGANISM: Artificial Sequence
<220> FEATURE:
<223> OTHER INFORMATION: chemically-synthesized polynucleotide

<400> SEQUENCE: 157
tctgggcaac aaagtgag                                                   18

<210> SEQ ID NO 158
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 158
ccagtttttt ttttttttg gaaatcc                                          27

<210> SEQ ID NO 159
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 159
gtccagtttt tttttttttt tggg                                            24

<210> SEQ ID NO 160
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 160
gtccagtttt tttttttttt tcactg                                          26

<210> SEQ ID NO 161
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 161
gtccagtttt tttttttttt tctgttc                                         27

<210> SEQ ID NO 162
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 162
gtccagtttt tttttttttt tctacct                                         27
```

<210> SEQ ID NO 163
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 163
gtccagtttt ttttttttt tgtacc                                        26

<210> SEQ ID NO 164
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 164
gtccagtttt ttttttttt tctacct                                       27

<210> SEQ ID NO 165
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 165 ccagttttt ttttttttc gcat                                           24

<210> SEQ ID NO 166
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 166
caggtccagt tttttttttt ttttaca                                      27

<210> SEQ ID NO 167
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 167
ggtccagttt ttttttttt ttgtag                                        26

<210> SEQ ID NO 168
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 168
gtccagtttt ttttttttt tcagga                                        26

<210> SEQ ID NO 169
<211> LENGTH: 27
<212> TYPE: DNA
<213> ORGANISM: Artificial Sequence
<220> FEATURE:

<223> OTHER INFORMATION: chemically-synthesized polynucleotide

<400> SEQUENCE: 169
gtccagtttt tttttttttt taactca                                              27

<210> SEQ ID NO 170
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 170
gtccagtttt tttttttttt tctacct                                              27

<210> SEQ ID NO 171
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 171
gtccagtttt tttttttttt tcaactc                                              27

<210> SEQ ID NO 172
<211> LENGTH: 25
<212> TYPE: DNA
<213> ORGANISM: Artificial Sequence
<220> FEATURE:
<223> OTHER INFORMATION: chemically-synthesized polynucleotide

<400> SEQUENCE: 172
cagttttttt ttttttttgc cctct                                                25

<210> SEQ ID NO 173
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 173
ggtccagttt tttttttttt ttctcg                                               26

<210> SEQ ID NO 174
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 174
ggtccagttt tttttttttt ttcatag                                              27

<210> SEQ ID NO 175
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 175
gtccagtttt tttttttttt taaagtc                                              27

```
<210> SEQ ID NO 176
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 176 gtttttttttt tttttttgccc gggt                                          24

<210> SEQ ID NO 177
<211> LENGTH: 28
<212> TYPE: DNA
<213> ORGANISM: Artificial Sequence
<220> FEATURE:
<223> OTHER INFORMATION: chemically-synthesized polynucleotide

<400> SEQUENCE: 177
ggtccagttt tttttttttt ttactttc                                        28

<210> SEQ ID NO 178
<211> LENGTH: 28
<212> TYPE: DNA
<213> ORGANISM: Artificial Sequence
<220> FEATURE:
<223> OTHER INFORMATION: chemically-synthesized polynucleotide

<400> SEQUENCE: 178
aggtccagtt tttttttttt tttagtag                                        28

<210> SEQ ID NO 179
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 179
ggtccagttt tttttttttt ttcaatg                                         27

<210> SEQ ID NO 180
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 180
ggtccagttt tttttttttt ttctaac                                         27

<210> SEQ ID NO 181
<211> LENGTH: 28
<212> TYPE: DNA
<213> ORGANISM: Artificial Sequence
<220> FEATURE:
<223> OTHER INFORMATION: chemically-synthesized polynucleotide

<400> SEQUENCE: 181
gtccagtttt tttttttttt tcacttag                                        28

<210> SEQ ID NO 182
<211> LENGTH: 25
<212> TYPE: DNA
<213> ORGANISM: Artificial Sequence
<220> FEATURE:
<223> OTHER INFORMATION: chemically-synthesized polynucleotide
```

<400> SEQUENCE: 182
ggtccagttt ttttttttttt ttggt                               25

<210> SEQ ID NO 183
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 183
ggtccagttt ttttttttttt ttcagt                              26

<210> SEQ ID NO 184
<211> LENGTH: 28
<212> TYPE: DNA
<213> ORGANISM: Artificial Sequence
<220> FEATURE:
<223> OTHER INFORMATION: chemically-synthesized polynucleotide

<400> SEQUENCE: 184
ggtccagttt ttttttttttt ttagttct                            28

<210> SEQ ID NO 185
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 185
tccagttttt ttttttttttt gctg                                24

<210> SEQ ID NO 186
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 186
tccagttttt ttttttttttt cacaca                              26

<210> SEQ ID NO 187
<211> LENGTH: 25
<212> TYPE: DNA
<213> ORGANISM: Artificial Sequence
<220> FEATURE:
<223> OTHER INFORMATION: chemically-synthesized polynucleotide

<400> SEQUENCE: 187
cagttttttt ttttttttcg ggaag                                25

<210> SEQ ID NO 188
<211> LENGTH: 25
<212> TYPE: DNA
<213> ORGANISM: Artificial Sequence
<220> FEATURE:
<223> OTHER INFORMATION: chemically-synthesized polynucleotide

<400> SEQUENCE: 188
gtccagtttt ttttttttttt tccag                               25

<210> SEQ ID NO 189
<211> LENGTH: 27

```
<212> TYPE: DNA
<213> ORGANISM: Artificial Sequence
<220> FEATURE:
<223> OTHER INFORMATION: chemically-synthesized polynucleotide

<400> SEQUENCE: 189
ggtccagttt ttttttttt ttacaga                                      27

<210> SEQ ID NO 190
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 190
gtccagtttt ttttttttt tacagga                                      27

<210> SEQ ID NO 191
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 191
ggtccagttt ttttttttt ttatctg                                      27

<210> SEQ ID NO 192
<211> LENGTH: 28
<212> TYPE: DNA
<213> ORGANISM: Artificial Sequence
<220> FEATURE:
<223> OTHER INFORMATION: chemically-synthesized polynucleotide

<400> SEQUENCE: 192
ggtccagttt ttttttttt ttagtaca                                     28

<210> SEQ ID NO 193
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 193
ggtccagttt ttttttttt ttaacca                                      27

<210> SEQ ID NO 194
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 194
aggtccagtt ttttttttt tttaact                                      27

<210> SEQ ID NO 195
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 195
```

```
gttttttttt tttttttcgcc ctct                                              24

<210> SEQ ID NO 196
<211> LENGTH: 25
<212> TYPE: DNA
<213> ORGANISM: Artificial Sequence
<220> FEATURE:
<223> OTHER INFORMATION: chemically-synthesized polynucleotide

<400> SEQUENCE: 196
gtccagtttt tttttttttt tgcac                                              25

<210> SEQ ID NO 197
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 197
tccagttttt tttttttttt cctctc                                             26

<210> SEQ ID NO 198
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 198 ccagttttttt ttttttttta cccagt                                            26

<210> SEQ ID NO 199
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 199 tccagtttttt tttttttttt aaagcag                                           27

<210> SEQ ID NO 200
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 200
cagttttttt ttttttttcg gggt                                               24

<210> SEQ ID NO 201
<211> LENGTH: 25
<212> TYPE: DNA
<213> ORGANISM: Artificial Sequence
<220> FEATURE:
<223> OTHER INFORMATION: chemically-synthesized polynucleotide

<400> SEQUENCE: 201
gtccagtttt tttttttttt tgggt                                              25

<210> SEQ ID NO 202
<211> LENGTH: 25
<212> TYPE: DNA
<213> ORGANISM: Artificial Sequence
```

```
<220> FEATURE:
<223> OTHER INFORMATION: chemically-synthesized polynucleotide

<400> SEQUENCE: 202
tccagttttt ttttttttttt gacca                                       25

<210> SEQ ID NO 203
<211> LENGTH: 25
<212> TYPE: DNA
<213> ORGANISM: Artificial Sequence
<220> FEATURE:
<223> OTHER INFORMATION: chemically-synthesized polynucleotide

<400> SEQUENCE: 203 ccagttttttt tttttttttc tccag                                       25

<210> SEQ ID NO 204
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 204
gtccagtttt tttttttttt tcacag                                       26

<210> SEQ ID NO 205
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 205
gtccagtttt tttttttttt tctcagt                                      27

<210> SEQ ID NO 206
<211> LENGTH: 26
<212> TYPE: DNA
<213> ORGANISM: Artificial Sequence
<220> FEATURE:
<223> OTHER INFORMATION: chemically-synthesized polynucleotide

<400> SEQUENCE: 206
tccagttttt tttttttttt ctgtgt                                       26

<210> SEQ ID NO 207
<211> LENGTH: 28
<212> TYPE: DNA
<213> ORGANISM: Artificial Sequence
<220> FEATURE:
<223> OTHER INFORMATION: chemically-synthesized polynucleotide

<400> SEQUENCE: 207
ggtccagttt tttttttttt ttattgtg                                     28

<210> SEQ ID NO 208
<211> LENGTH: 27
<212> TYPE: DNA
<213> ORGANISM: Artificial Sequence
<220> FEATURE:
<223> OTHER INFORMATION: chemically-synthesized polynucleotide

<400> SEQUENCE: 208
tccagttttt tttttttttt aggtctc                                      27
```

<210> SEQ ID NO 209
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 209
tggaattctc gggtgccaag g                                             21

<210> SEQ ID NO 210
<211> LENGTH: 22
<212> TYPE: RNA
<213> ORGANISM: Artificial Sequence
<220> FEATURE:
<223> OTHER INFORMATION: chemically-synthesized polynucleotide

<400> SEQUENCE: 210
ucguaugccg ucuucugcuu gu                                            22

<210> SEQ ID NO 211
<211> LENGTH: 17
<212> TYPE: DNA
<213> ORGANISM: Artificial Sequence
<220> FEATURE:
<223> OTHER INFORMATION: chemically-synthesized polynucleotide

<400> SEQUENCE: 211
ctgtaggcac catcaat                                                  17

<210> SEQ ID NO 212
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 212
atctcgtatg ccgtcttctg cttg                                          24

<210> SEQ ID NO 213
<211> LENGTH: 22
<212> TYPE: RNA
<213> ORGANISM: Artificial Sequence
<220> FEATURE:
<223> OTHER INFORMATION: chemically-synthesized polynucleotide

<400> SEQUENCE: 213
ucguaugccg ucuucugcuu gu                                            22

<210> SEQ ID NO 214
<211> LENGTH: 24
<212> TYPE: DNA
<213> ORGANISM: Artificial Sequence
<220> FEATURE:
<223> OTHER INFORMATION: chemically-synthesized polynucleotide

<400> SEQUENCE: 214
atctcgtatg ccgtcttctg cttg                                          24

<210> SEQ ID NO 215
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 215
tggaattctc gggtgccaag g                                                   21

<210> SEQ ID NO 216
<211> LENGTH: 26
<212> TYPE: RNA
<213> ORGANISM: Artificial Sequence
<220> FEATURE:
<223> OTHER INFORMATION: chemically-synthesized polynucleotide

<400> SEQUENCE: 216
guucagaguu cuacaguccg acgauc                                              26

<210> SEQ ID NO 217
<211> LENGTH: 26
<212> TYPE: RNA
<213> ORGANISM: Artificial Sequence
<220> FEATURE:
<223> OTHER INFORMATION: chemically-synthesized polynucleotide

<400> SEQUENCE: 217
guucagaguu cuacaguccg acgauc                                              26

<210> SEQ ID NO 218
<211> LENGTH: 26
<212> TYPE: RNA
<213> ORGANISM: Artificial Sequence
<220> FEATURE:
<223> OTHER INFORMATION: chemically-synthesized polynucleotide

<400> SEQUENCE: 218
guucagaguu cuacaguccg acgauc                                              26

<210> SEQ ID NO 219
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 219
caagcagaag acggcatacg a                                                   21

<210> SEQ ID NO 220
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 220
caagcagaag acggcatacg a                                                   21

<210> SEQ ID NO 221
<211> LENGTH: 22
<212> TYPE: DNA
<213> ORGANISM: Artificial Sequence
<220> FEATURE:
<223> OTHER INFORMATION: chemically-synthesized polynucleotide

<400> SEQUENCE: 221
gccttggcac ccgagaattc ca                                                  22

<210> SEQ ID NO 222

-continued

```
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 222
caagcagaag acggcatacg a                                              21

<210> SEQ ID NO 223
<211> LENGTH: 21
<212> TYPE: DNA
<213> ORGANISM: Artificial Sequence
<220> FEATURE:
<223> OTHER INFORMATION: chemically-synthesized polynucleotide

<400> SEQUENCE: 223
caagcagaag acggcatacg a                                              21

<210> SEQ ID NO 224
<211> LENGTH: 63
<212> TYPE: DNA
<213> ORGANISM: Artificial Sequence
<220> FEATURE:
<223> OTHER INFORMATION: chemically-synthesized polynucleotide

<400> SEQUENCE: 224
caagcagaag acggcatacg agatcgtgat gtgactggag ttccttggca cccgagaatt    60
cca                                                                  63

<210> SEQ ID NO 225
<211> LENGTH: 44
<212> TYPE: DNA
<213> ORGANISM: Artificial Sequence
<220> FEATURE:
<223> OTHER INFORMATION: chemically-synthesized polynucleotide

<400> SEQUENCE: 225
aatgatacgg cgaccaccga caggttcaga gttctacagt ccga                     44

<210> SEQ ID NO 226
<211> LENGTH: 44
<212> TYPE: DNA
<213> ORGANISM: Artificial Sequence
<220> FEATURE:
<223> OTHER INFORMATION: chemically-synthesized polynucleotide

<400> SEQUENCE: 226
aatgatacgg cgaccaccga caggttcaga gttctacagt ccga                     44

<210> SEQ ID NO 227
<211> LENGTH: 50
<212> TYPE: DNA
<213> ORGANISM: Artificial Sequence
<220> FEATURE:
<223> OTHER INFORMATION: chemically-synthesized polynucleotide

<400> SEQUENCE: 227
aatgatacgg cgaccaccga gatctacacg ttcagagttc tacagtccga               50
```